US009951051B2

(12) United States Patent
Tadano et al.

(10) Patent No.: US 9,951,051 B2
(45) Date of Patent: Apr. 24, 2018

(54) PROCESS FOR PRODUCING ALKYNYLKETONE DERIVATIVE

(71) Applicant: Shionogi & Co., Ltd., Osaka (JP)

(72) Inventors: Genta Tadano, Osaka (JP); Fumiya Ikarashi, Hyogo (JP); Kazuya Okamoto, Osaka (JP); Toshikatsu Maki, Osaka (JP); Motoyuki Hagihara, Hyogo (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 15/314,181

(22) PCT Filed: May 28, 2015

(86) PCT No.: PCT/JP2015/065336
§ 371 (c)(1),
(2) Date: Nov. 28, 2016

(87) PCT Pub. No.: WO2015/182682
PCT Pub. Date: Dec. 3, 2015

(65) Prior Publication Data
US 2017/0197943 A1 Jul. 13, 2017

(30) Foreign Application Priority Data
May 29, 2014 (JP) ................................. 2014-111333

(51) Int. Cl.
| C07D 403/12 | (2006.01) |
| C07D 239/94 | (2006.01) |
| C07D 295/03 | (2006.01) |
| C07C 321/04 | (2006.01) |
| C07D 413/12 | (2006.01) |

(52) U.S. Cl.
CPC .......... C07D 403/12 (2013.01); C07C 321/04 (2013.01); C07D 239/94 (2013.01); C07D 295/03 (2013.01); C07D 413/12 (2013.01); C07B 2200/13 (2013.01)

(58) Field of Classification Search
CPC .................................................. C07D 471/04
See application file for complete search history.

(56) References Cited

U.S. PATENT DOCUMENTS

2014/0171447 A1  6/2014  Johnson

FOREIGN PATENT DOCUMENTS

| EP | 0 279 477 | 8/1988 |
| EP | 1 854 789 | 11/2007 |
| EP | 2 374 801 | 10/2011 |
| JP | 56-97250 | 8/1981 |
| JP | 60-169433 | 9/1985 |

OTHER PUBLICATIONS

International Search Report dated Aug. 11, 2015 in International (PCT) Application No. PCT/JP2015/065336.
Liang et al., "Pd-Catalyzed Copper-Free Carbonylative Sonogashira Reaction of Aryl Iodides with Alkynes for the Synthesis of Alkynyl Ketones and Flavones by Using Water as a Solvent", J. Org. Chem., vol. 70, 2005, pp. 6097-6100.
Ahmed et al., "Carbonylative Sonogashira Coupling of Terminal Alkynes with Aqueous Ammonia", Organic Letters, vol. 5, No. 17, 2003, pp. 3057-3060.
Sashida et al., "An Alternative Facile Preparation of Telluro- and Selenochromones from o-Bromophenyl Ethynyl Ketones", Synthesis, vol. 5, May 1998, pp. 745-748.
Yoneda et al., "The Antiproliferative Effects of Tyrosine Kinase Inhibitors Tyrphostins on a Human Squamous Cell Carcinoma in Vitro and in Nude Mice", Cancer Research, vol. 51, Aug. 15, 1991, pp. 4430-4435.
Reddy et al., "Inhibition of Breast Cancer Cell Growth in Vitro by a Tyrosine Kinase Inhibitor", Cancer Research, vol. 52, Jul. 1, 1992, pp. 3636-3641.
Brunton et al., "Cell-signaling targets for antitumour drug development", Cancer Chemother Pharmacol, vol. 32, 1993, pp. 1-19.
Kokai et al., "Synergistic Interaction of p185c-neu and the EGF Receptor Leads to Transformation of Rodent Fibroblasts", Cell, vol. 58, Jul. 28, 1989, pp. 287-292.
Arcadi et al., "The Palladium-Catalysed Carbonylative Coupling of 5-(Trimethylsilylethynyl)-3', 5'-di-O-acetyl-2'- deoxyuridine and 1-Alkynes with Aryl Iodides", Synlett, Aug. 1995, pp. 823-824.
Kobayashi et al., "Carbonylation of Organic Halides in the Presence of Terminal Acetylenes; Novel Acetylenic Ketone Synthesis", J.C.S. Chem. Comm., Jan. 1981, pp. 333-334.
Delaude et al., "Coupling and Carbonylation of Iodoaromatics and Terminal Alkynes or Alkynols Catalyzed by a Dimeric Palladium Hydroxide", Synthesis, Nov. 1994, pp. 1149-1151.
Pan et al., "CuI/N,N-Dimethylglycine-Catalyzed Coupling of Vinyl Halides with Amides or Carbamates", Organic Letters, vol. 6, No. 11, Apr. 2004, pp. 1809-1812.
Chinchilla et al., "The Sonogashira Reaction: A Booming Methodology in Synthetic Organic Chemistry", Chem. Rev., vol. 107, 2007, pp. 874-922.
Nihonkagakukaishi, Journal of the Chemical Society of Japan, No. 3, 1985, pp. 537-546.
Iizuka et al., "Palladium-Catalyzed Alkynylcarbonylation of Aryl Iodides with the Use of Mo(CO)$_6$ in the Presence of tBu$_3$P Ligand", Eur. J. Org. Chem., 2007, pp. 5180-5182.
Park et al., "Pd-Catalyzed Carbonylative Reactions of Aryl Iodides and Alkynyl Carboxylic Acids via Decarboxylative Couplings", Organic Letters, vol. 13, No. 5, 2011, pp. 944-947.
Wu et al., "Convenient and General Palladium-Catalyzed Carbonylative Sonogashira Coupling of Aryl Amines", Angew. Chem. Int. Ed., vol. 50, 2011, pp. 11142-11146.
European Search Report dated Oct. 10, 2017 in European Patent Application No. 15799305.5.

(Continued)

*Primary Examiner* — Paul V Ward
(74) *Attorney, Agent, or Firm* — Wenderoth, Lind & Ponack, L.L.P.

(57) ABSTRACT

The present invention relates to a Sonogashira-Carbonylation reaction using two types of gas, as well as novel crystals which can control a heat of the said reaction and the process of producing the same. In addition, the present invention relates to a ligand (additive) to prevent the deactivation of a palladium catalyst.

25 Claims, 7 Drawing Sheets

(56) References Cited

OTHER PUBLICATIONS

International Preliminary Report on Patentability and Written Opinion of the International Searching Authority dated Dec. 8, 2016 in corresponding International (PCT) Application No. PCT/JP2015/065336.
Extended European Search Report dated Jan. 18, 2018 in European Application No, 15799305.6.
Vincent Gembus et al., "Palladium Catalyzed One-Pot Sequential Suzuki Cross-Coupling-Direct C-H Functionalization of Imidazo[1,2-a]pyrazines", Organic Letters, 2012, vol. 14, No. 23, pp. 6012-6015.

[Figure 1]
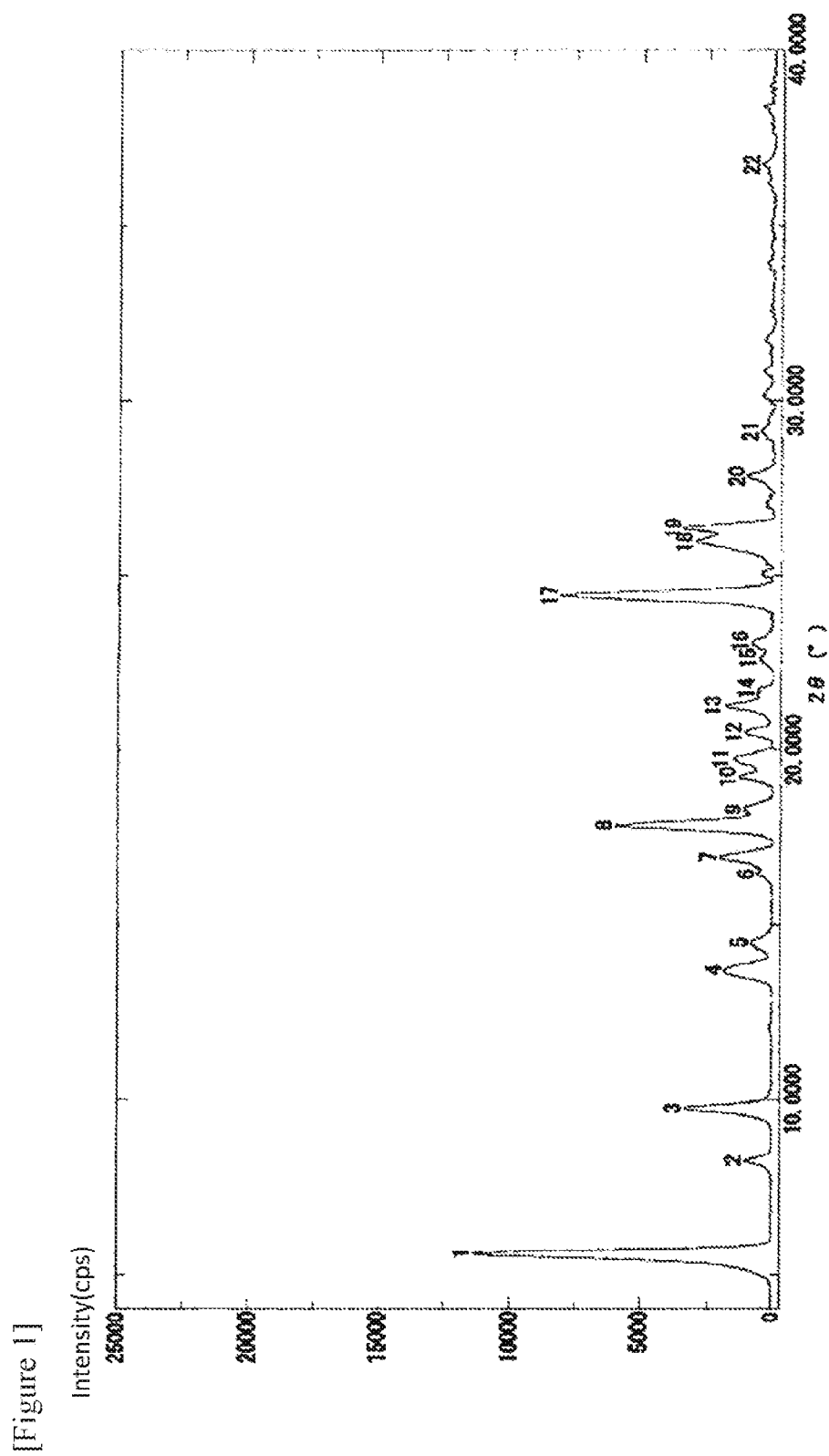

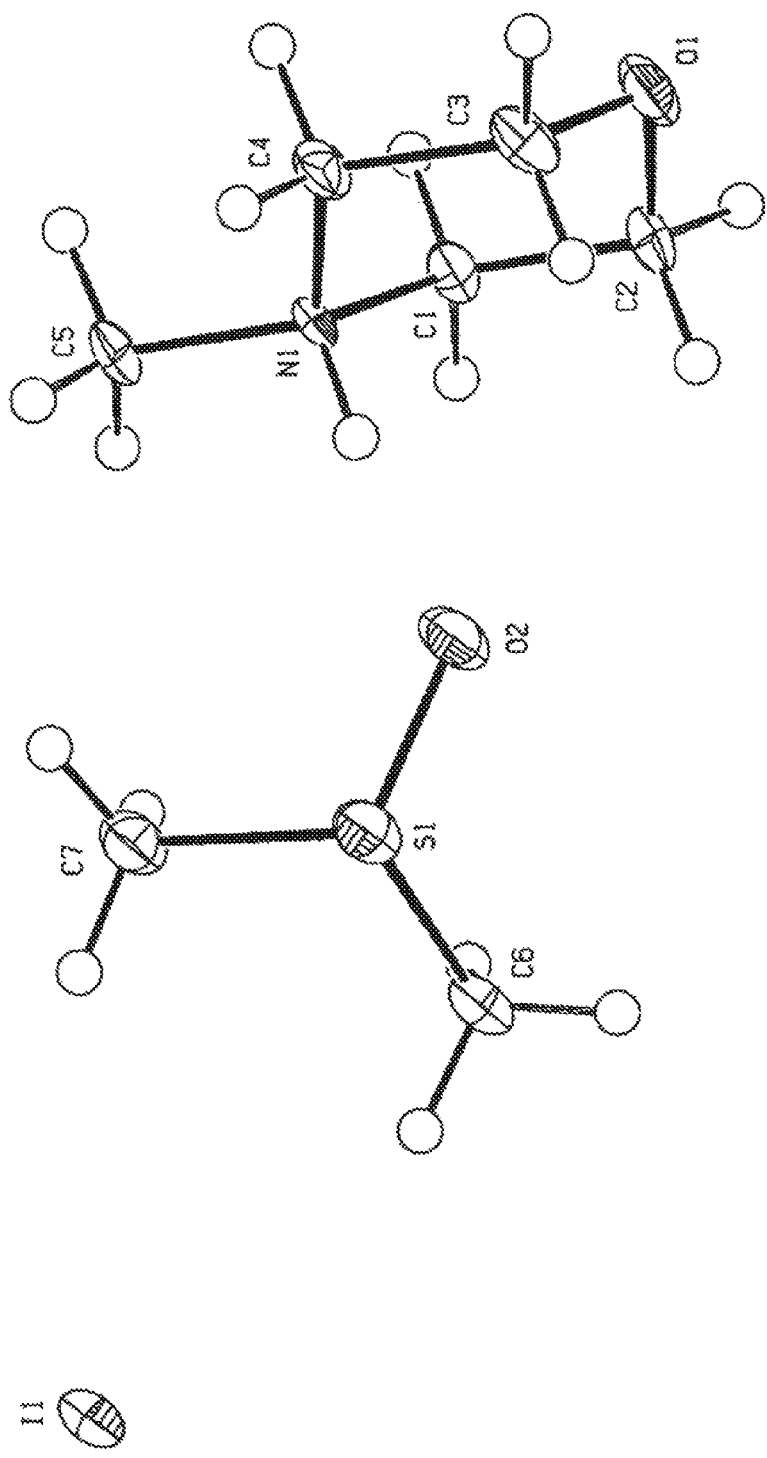
[Figure 2]

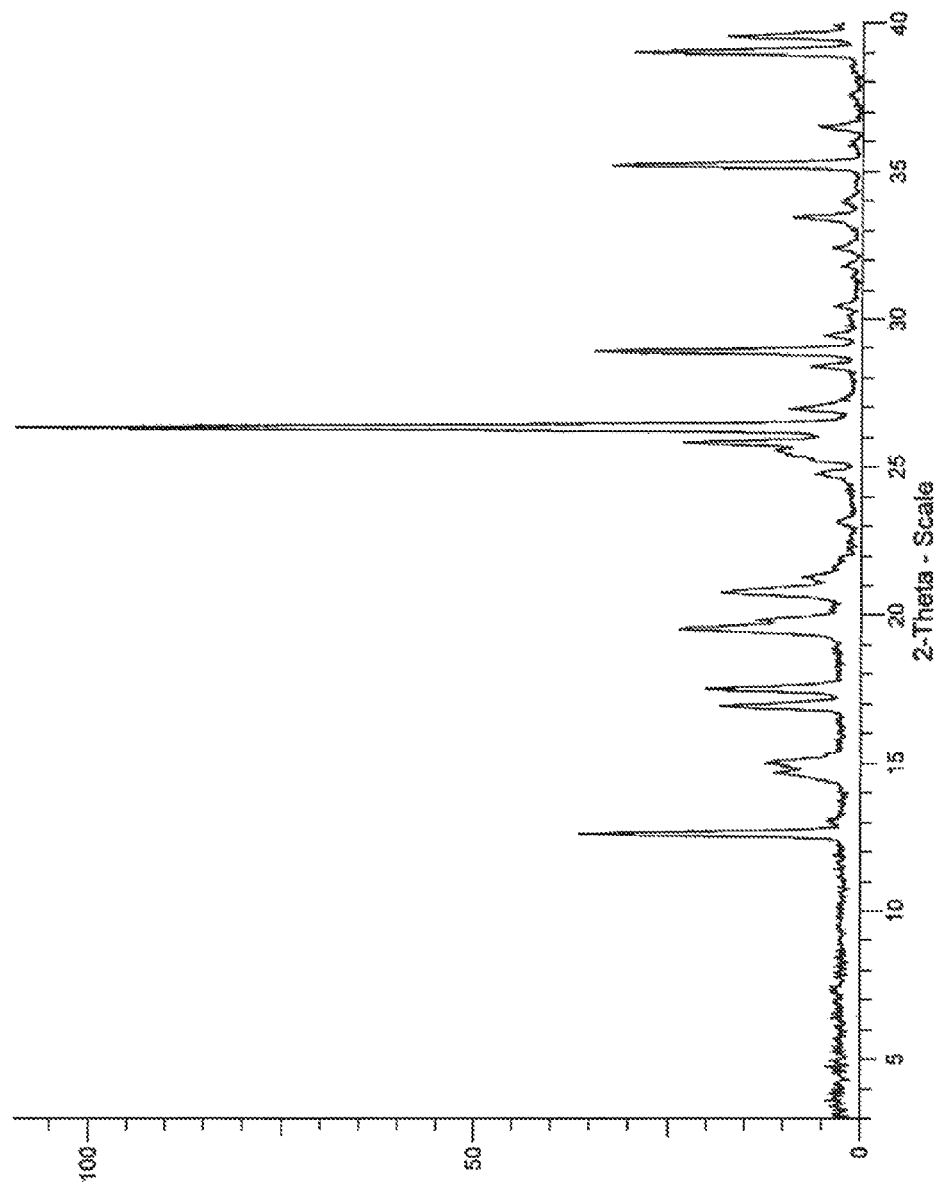
[Figure 3]

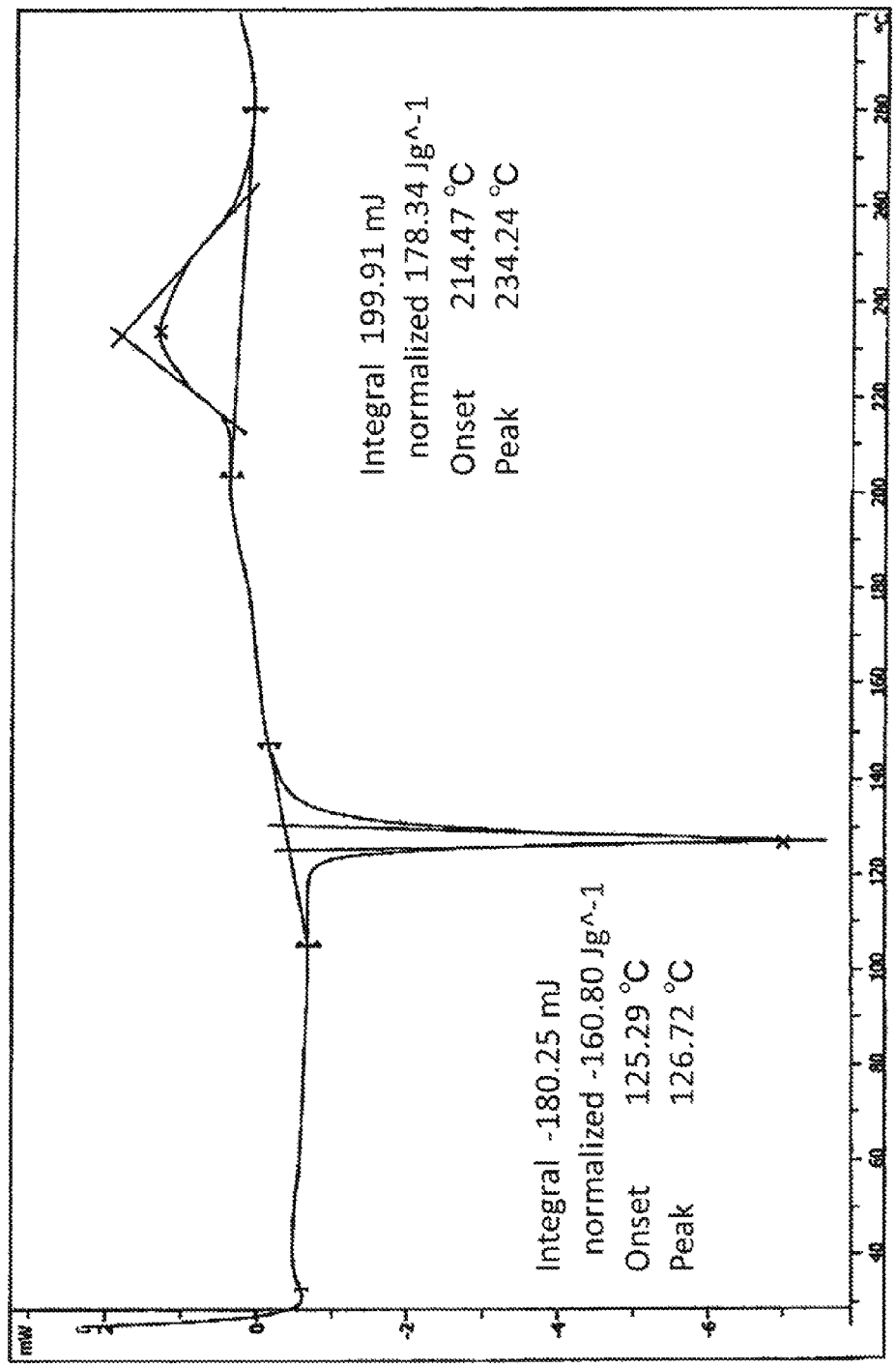
[Figure 4]

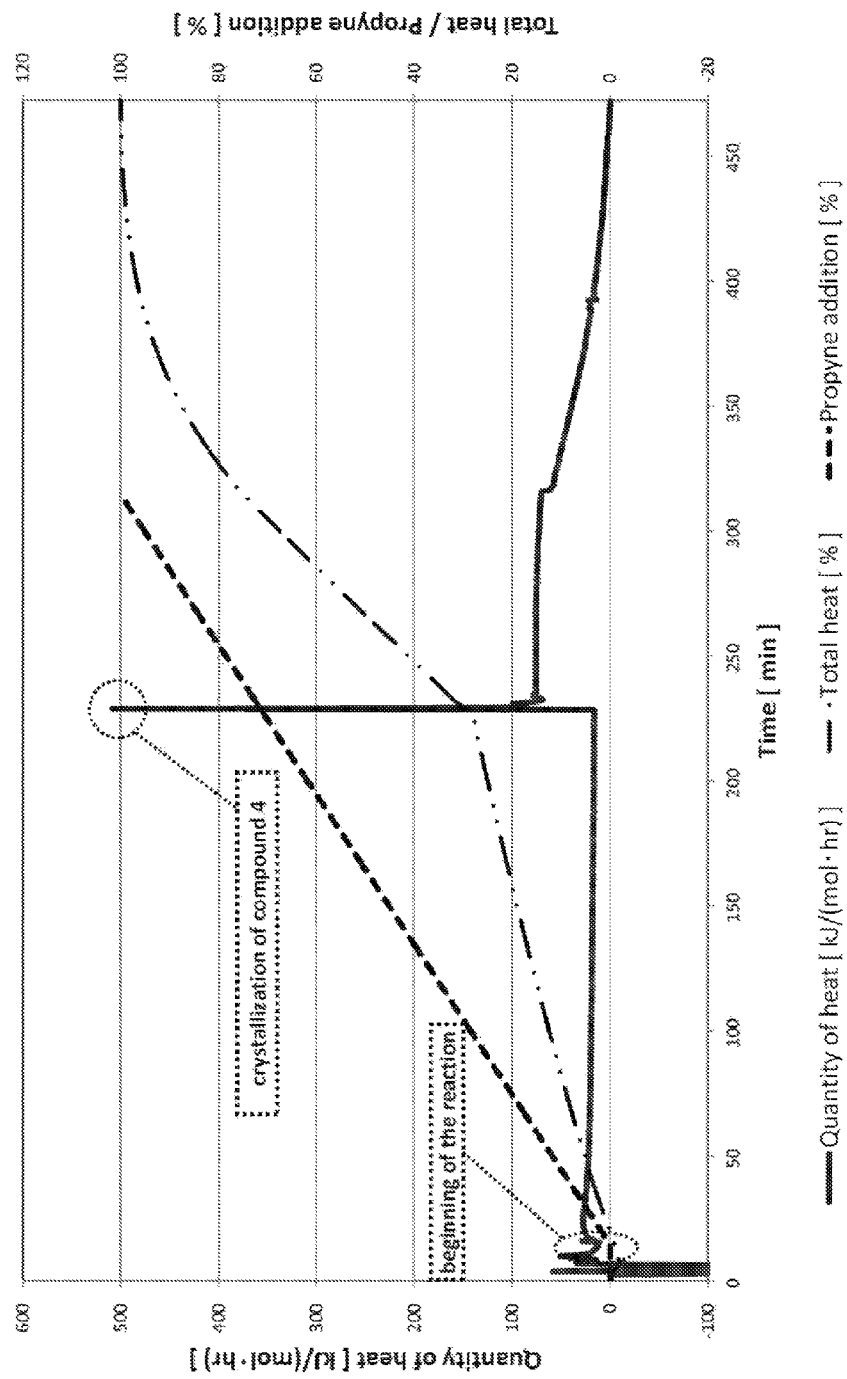
[Figure 5]

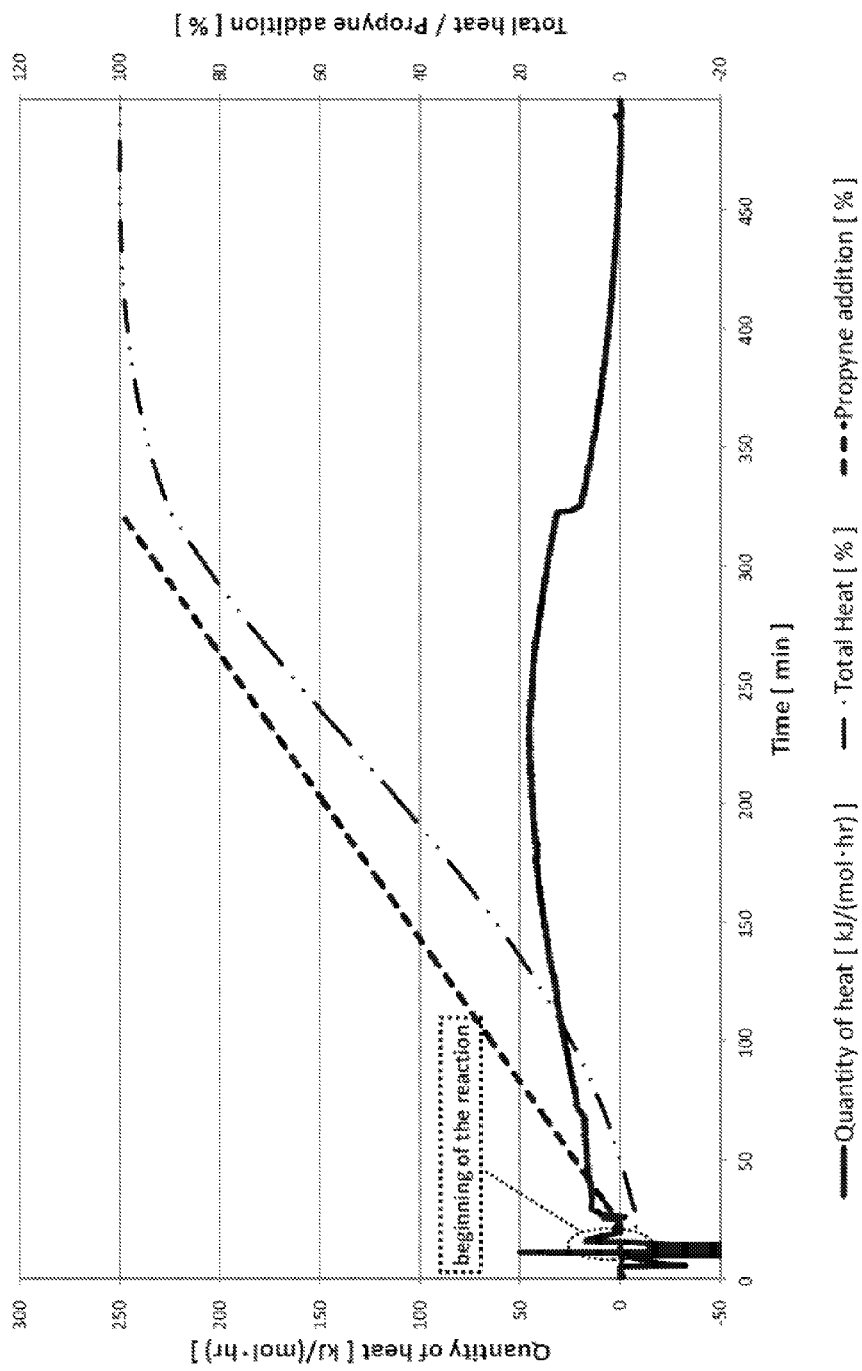
[Figure 6]

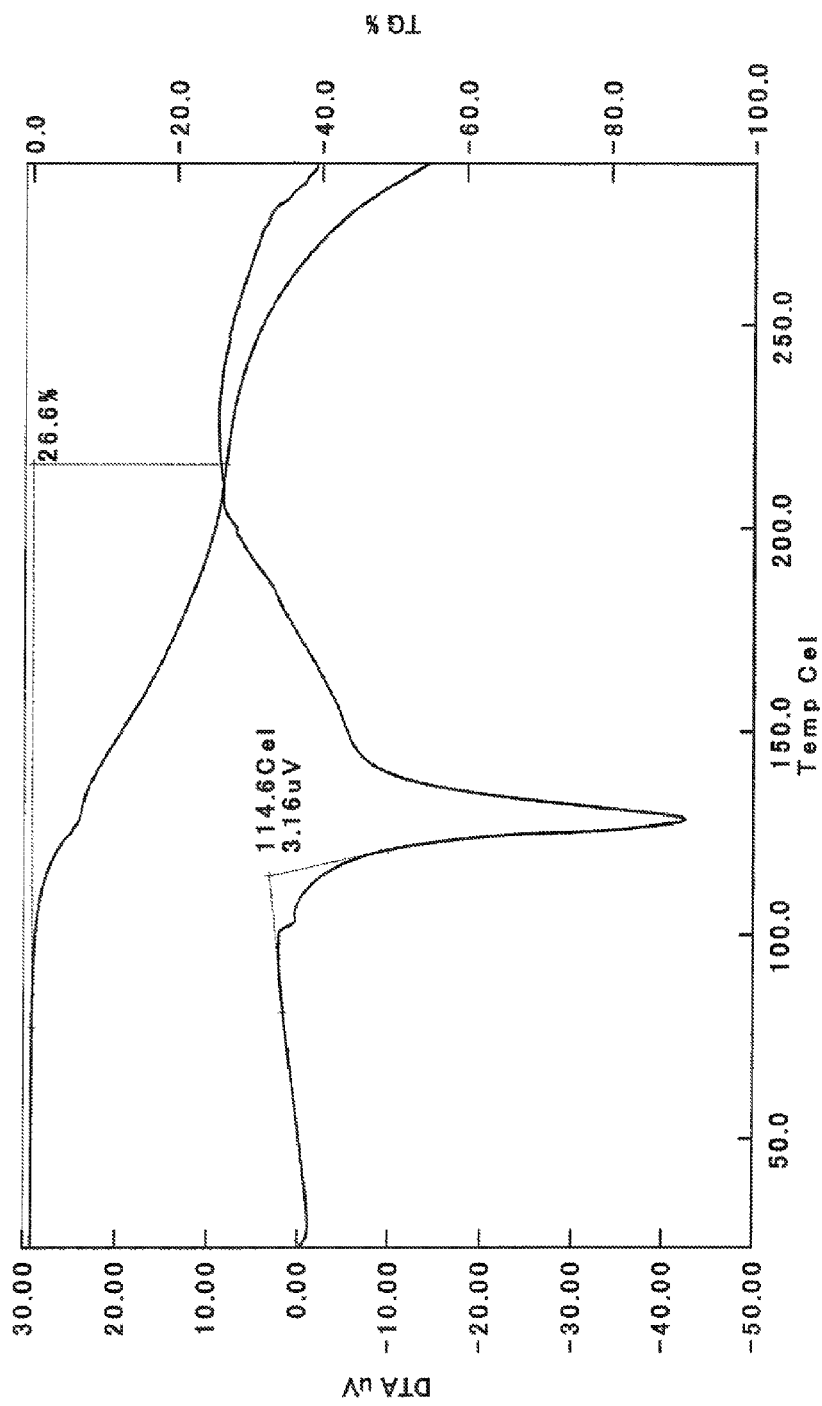
[Figure 7]

PROCESS FOR PRODUCING ALKYNYLKETONE DERIVATIVE

TECHNICAL FIELD

The present invention relates to a compound having a dual inhibitory activity of both EGF receptor tyrosine kinase and HER2 tyrosine kinase, a process for producing a compound having a 1-oxo-2-butyn-1-yl substituent which is useful for a synthetic intermediate, and crystal of the said intermediate compound. Furthermore, the present invention relates to a novel compound which can control the generation of the reaction heat during the production of the intermediate compound, and crystal thereof.

BACKGROUND ART

Tyrosine kinase is an enzyme which phosphorylates tyrosine residues in substrate proteins, and is known to play an important role in an intracellular signal transduction system concerning cellular differentiation and proliferation. Especially, it is known that a growth factor receptor tyrosine kinase (hereinafter receptor tyrosine kinase) such as HER2 (also called as ErbB2 or Neu) and EGF receptor etc. are considerably involved in cancer development, and their activities are increased in a variety of human cancers (Non-Patent Literature 1, Non-Patent Literature 2 and Non-Patent Literature 3).

Also it is known that co-expression of EGF receptor and HER2 further promotes canceration by EGF receptor alone (Non-Patent Literature 4) and a dual inhibitor that inhibits tyrosine kinase of both EGF receptor and HER2 is advantageous in having superior therapeutic effect in wider range of disease by synergistic effect of dual inhibition when compared with a EGF receptor or a HER2 selective inhibitor.

A quinazoline derivative (VI) having a substituent containing an alkoxyimino structure at 6-position:

[Chemical Formula 1]

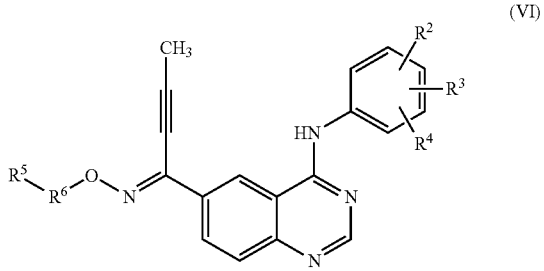

(VI)

wherein $R^2$ is a hydrogen atom, halogen, substituted or unsubstituted alkyloxy, substituted or unsubstituted alkenyloxy, substituted or unsubstituted alkynyloxy or formula: —Y—$R^y$ wherein Y is —O—, —S—, —$SO_2$— or alkylene which may be intervened with —O—, —S— or —N($R^z$)—; and $R^y$ is substituted or unsubstituted aryl or substituted or unsubstituted heteroaryl; $R^z$ is a hydrogen atom, substituted or unsubstituted alkyl, substituted or unsubstituted acyl, substituted or unsubstituted alkyloxycarbonyl, substituted or unsubstituted alkenyloxycarbonyl or substituted or unsubstituted aralkyloxycarbonyl;
$R^3$ and $R^4$ are each independently a hydrogen atom, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, halogen, hydroxy, mercapto, cyano or substituted or unsubstituted amino;
$R^5$ is substituted or unsubstituted aryl, substituted or unsubstituted heteroaryl or substituted or unsubstituted heterocyclyl or substituted or unsubstituted amino, and
$R^6$ is substituted or unsubstituted C1-3 alkylene,
is one of these dual inhibitors and is expected as a novel cancer agent (Patent Literature 1).

A compound (III) having a 1-oxo-2-butyn-1-yl substituent at 6-position:

[Chemical Formula 2]

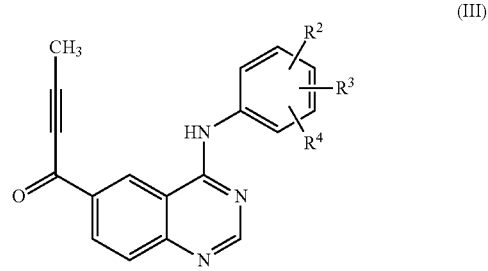

(III)

wherein $R^2$, $R^3$ and $R^4$ are as defined above,
is an important synthetic intermediate for preparing a quinazoline derivative (VI), since the above quinazoline derivative (VI) is prepared by reacting a compound (III) with an alkoxyamine derivative.

In addition, Patent Document 2 discloses that a process for producing a compound represented by Formula (III):

[Chemical Formula 3]

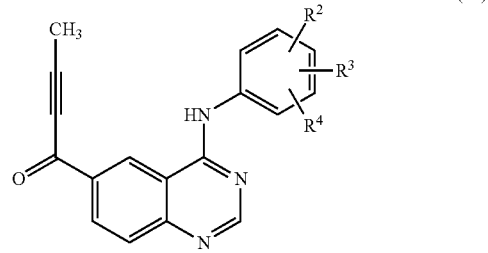

(III)

wherein $R^2$ is a hydrogen atom, halogen, substituted or unsubstituted alkyloxy, substituted or unsubstituted alkenyloxy, substituted or unsubstituted alkynyloxy or a group represented by the formula: —Y—$R^y$ wherein —Y— is —O—, —S—, —$SO_2$— or alkylene which may be intervened with —O—, —S— or —N($R^z$)—; and $R^y$ is substituted or unsubstituted aryl or substituted or unsubstituted heteroaryl; $R^z$ is a hydrogen atom, substituted or unsubstituted alkyl, substituted or unsubstituted acyl, etc.; $R^3$ and $R^4$ are each independently hydrogen atom, substituted or unsubstituted alkyl, substituted or unsubstituted alkenyl, etc.;
characterized in that
Reaction A, in which a compound represented by the formula (I):

[Chemical Formula 4]

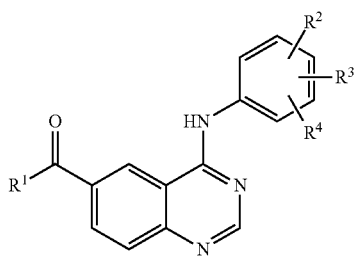

wherein $R^1$ is a group represented by the formula: —O—$R^X$ or —S—$R^X$ wherein $R^X$ is substituted or unsubstituted alkyl, substituted or unsubstituted alkenyl, substituted or unsubstituted alkynyl, substituted or unsubstituted aryl etc., $R^2$, $R^3$ and $R^4$ are as defined above,
is reacted with a compound represented by the formula: ($R^b$O—)N(—$R^a$)H
wherein $R^a$ and $R^b$ are each independently substituted or unsubstituted C1-C3 alkyl, and one or more metallic reagent(s) selected from the group consisting of Grignard reagent, sodium hydride, alkyllithium, alkenyllithium, alkynyllithium, phenyllithium, and lithium amide;
and Reaction B, in which the product of Reaction A is reacted with 1-propynyl metal acetylide;
are carried out substantially as one step by continuously conducting these two reactions.

Non-patent Documents 5-9 disclose Sonogashira-carbonylation reactions using liquid alkyne, but Sonogashira-carbonylation reaction using gaseous alkyne (example: acetylene, propyne) has not been known.

Non-patent Document 10 discloses that N,N-dimethylglycine is effective as ligand for copper, but it has not been reported that the ligand is involved in the precipitate of the palladium metal. Neither are there any examples of adding an effective ligand (additive) for copper to control the precipitate of palladium metal in various Sonogashira reactions in Non-patent Document 11.

Sonogashira-carbonylation reactions by using iodobenzene, carbon monoxide, phenylacetylene, triethylamine and palladium catalyst are described in Non-patent Document 12. Example of the reaction in which triethylamine hydroiodide salt is generated as by-product is disclosed, but new compound and the crystal thereof of the present invention are not disclosed.

PRIOR ART REFERENCES

Patent Document

[Patent Document 1] International Patent Publication No. 2006/090717 pamphlet
[Patent Document 2] International Patent Publication No. 2010/074150 pamphlet Non-Patent Document

[Non-patent Document 1] Cancer Research (Cancer Res.), 1991, vol. 51, p. 4430-4435
[Non-patent Document 2] Cancer Research (Cancer Res.), 1992, vol. 52, p. 3636-3641
[Non-patent Document 3] Cancer Chemotherapy and Pharmacology (Cancer Chemother. Pharmacol.), 1993, vol. 32, p. 1-19
[Non-patent Document 4] Cell, 1989, vol. 58, p. 287-292
[Non-patent Document 5] Synlett, 1995, p. 823-824
[Non-patent Document 6] Journal of the Chemical Society, Chemical Communications (J. C. S. Chem. Comm.), 1981, p. 333-334
[Non-patent Document 7] Synthesis, 1994, p. 1149-1151
[Non-patent Document 8] ORGANIC LETTERS, 2003, vol. 5, No. 17, p. 3057-3060
[Non-patent Document 9] The Journal of Organic Chemistry (J. Org. Chem.), 2005, vol. 70, p. 6097-6100
[Non-patent Document 10] ORGANIC LETTERS, 2004, vol. 6, No. 11, p. 1809-1812
[Non-patent Document 11] Chemical Reviews (Chem. Rev.), 2007, vol. 107, p. 874-922
[Non-patent Document 12] Journal of the Chemical Society of Japan, 1985, No. 3, p. 537-546

SUMMARY OF THE INVENTION

Problems to be Solved by the Invention

In the reference example 1 of Patent Document 1, a process for producing a compound represented by Formula (VII-4) is disclosed, in which the compound represented by Formula (VII-4) is prepared from a compound represented by Formula (III-1) via three steps.

[Chemical Formula 5]

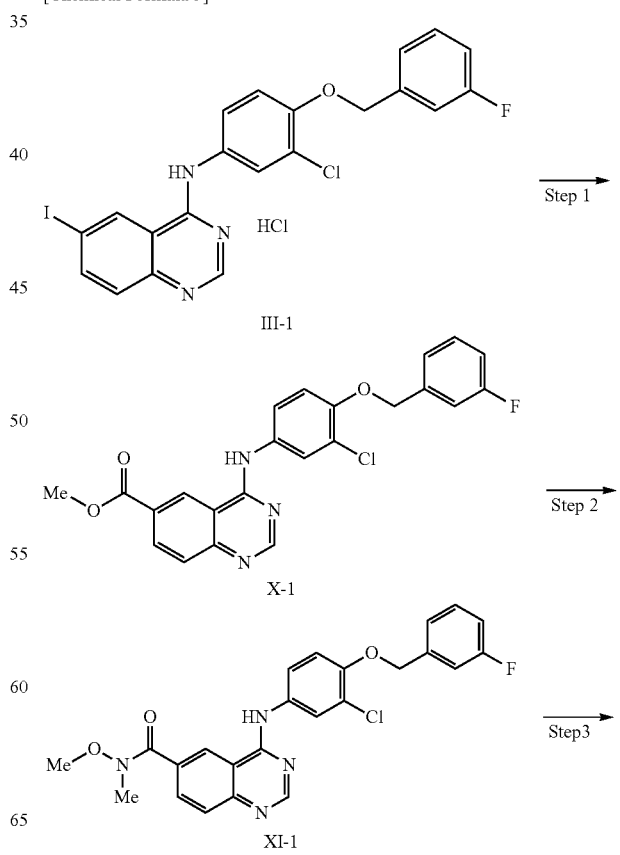

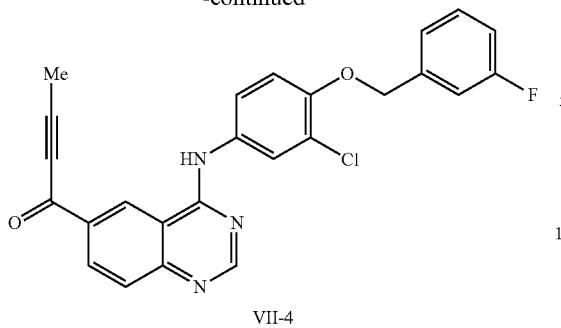

VII-4

Additionally, in Patent Document 2, a process for producing a compound represented by Formula (IV) is disclosed, in which the compound represented by Formula (IV) is prepared from a compound represented by Formula (I-1) through a methoxymethylamide (Reaction A) as one step without isolating (Reaction B).

In comparison with Patent Document 1, it turns out that the producing method described in Patent Document 2 can prepare the compound represented by Formula (IV), which is the compound represented by Formula (VII-4) in Patent Document 1, through one step less than that of described in Patent Document 1.

However, the producing methods described in Patent Document 1 and Patent Document 2 are not satisfactory and there was room for improvement in the methods.

The present invention relates to a process for producing a compound represented by Formula (II) by Sonogashira-carbonylation reaction of a compound represented by Formula (I) with a compound represented by Formula (III) as indicated below.

[Chemical Formula 7]

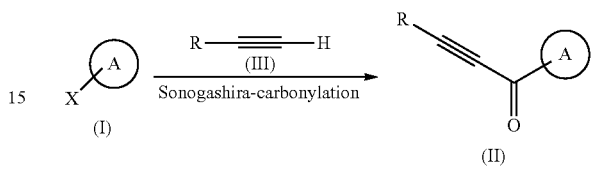

wherein ring A is a substituted or unsubstituted aromatic heterocycle or a substituted or unsubstituted aromatic carbocycle; X is a leaving group; R is hydrogen or methyl.

Means for Solving the Problem

It is detailed in Examples of the present invention that for example, a compound represented by Formula (II″) is pre-

[Chemical Formula 6]

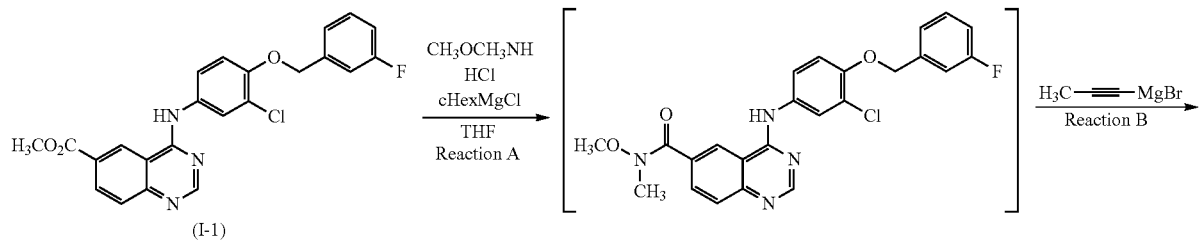

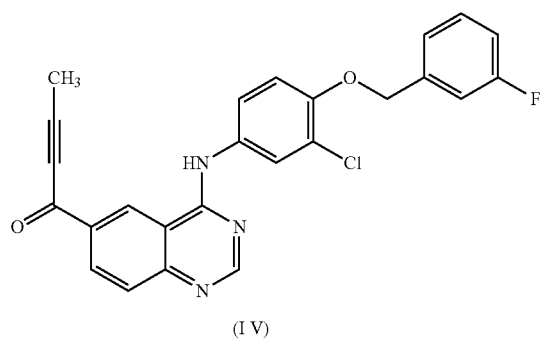

(IV)

pared from a compound represented by Formula (I''') with propyne gas by Sonogashira-carbonylation reaction as indicated below.

[Chemical Formula 8]

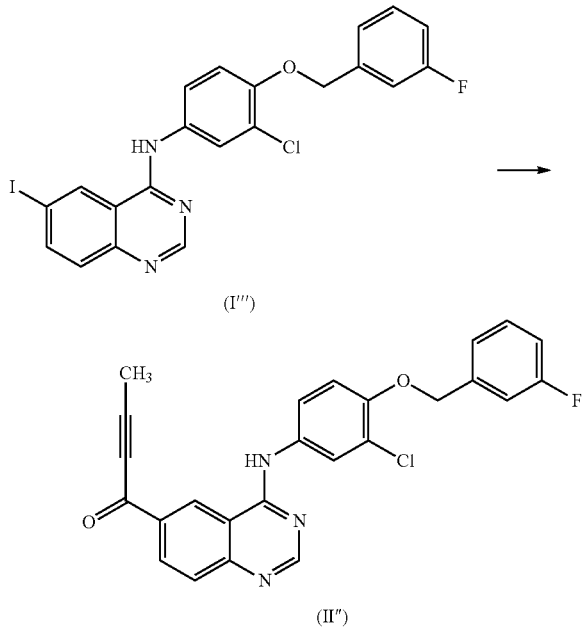

In other words, the compound represented by Formula (VII-4) (alkynylketone derivative) is prepared from the compound represented by Formula (III-1) (iodine derivative) via 3 steps by the producing method described in Patent Document 1. In contrast, the compound represented by Formula (II'') (alkynylketone derivative) is prepared from the compound represented by Formula (I''') (iodo derivative) via 1 step by the producing method described in the present invention. Therefore, the alkynylketone derivative can be prepared via fewer steps compared to the heretofore known producing method.

Additionally, with respect to ring A of Formula (I), the reaction of the present invention can be performed by using compounds which have an aromatic carbocycle (for example, a benzene ring) instead of the compounds which have an aromatic heterocycle (a quinazoline ring) as mentioned previously. The present invention can be applied to various substrates, and it may be said that the present invention is an industrially useful method since the alkynylketone derivative can be obtained via one step from iodo derivative.

The said Sonogashira-carbonylation reaction needs to handle two types of gaseous carbon monoxide and propyne gas, an aryacetylene which is not inserted carbon monoxide is generated as by-product since the solubility of propyne gas is higher than that of carbon monoxide, and it comes as a consequence of low yield and low quality of the product. The inventors of the present invention found the producing method in which the desired product can be obtained in high yield even in the Sonogashira-carbonylation reaction using two types of gases as mentioned previously.

Additionally, it is well known that in a reaction using palladium catalyst, the palladium catalyst is deactivated during the reaction to precipitate a palladium black, and it causes the loss of quality of the produced crystal and the loss of reaction rate. The inventors of the present invention found that the precipitate of the palladium black can be significantly reduced by adding ligands (additives) effective for copper.

Furthermore, in the said Sonogashira-carbonylation reaction, there was a possible risk of the increase of internal pressure in the reaction vessel or the loss of reaction control, etc. when the large scale synthesis is carried out. However, the inventors of the present invention found that the reaction heat can be easily controlled by adding crystal of the novel compound of the present invention in advance into the reaction system before starting the reaction.

The present invention relates to the following items 1) to 43).

1) A process for producing a compound represented by Formula (II);

[Chemical Formula 9]

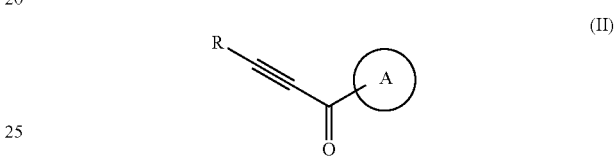

wherein ring A is a substituted or unsubstituted aromatic heterocycle or a substituted or unsubstituted aromatic carbocycle; R is a hydrogen atom or methyl, characterized by reacting a compound represented by Formula (I);

[Chemical Formula 10]

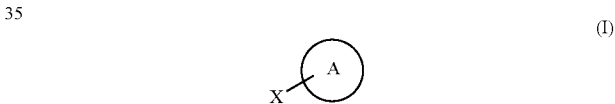

wherein ring A is as defined above, X is a leaving group, with carbon monoxide and a compound represented by Formula (III);

[Chemical Formula 11]

wherein R is as defined above,
in the presence of a palladium catalyst, a phosphine ligand, a catalyst comprising Group 11 element and a base.

2) The process according to the above item 1), wherein R is methyl.

3) The process according to the above items 1) or 2), wherein the palladium catalyst is $Pd_2(dba)_3$, $PdCl_2$ dppf, $PdCl_2(PPh_3)_2$, $Pd(OAc)_2$, $Pd(PPh_3)_4$, Pd/C, $PdCl_2$, Pd-PEPPSI™-IPr, Bis[cinnamyl palladium Cl], $PdCl_2$ (Xantphos) or $Pd(OH)_2$.

4) The process according to any one of the above items 1) to 3), wherein the phosphine ligand is Xantphos, $P(2-furyl)_3$, $PPh_3$, $P(o-tol)_3$, $P(OPh)_3$, $P(OMe)_3$, dppp, dppb, dppf, BINAP, X-Phos, $P(t-Bu)_3$, $P(Oi-Pr)_3$, $P(p-MeOPh)_3$ or DPEPhos.

5) The process according to any one of the above items 1) to 4), wherein the catalyst comprising Group 11 element is copper iodide(I), copper iodide(II), copper chloride(I), copper chloride(II), copper acetate(I), copper acetate(II), copper oxide(II), copper bromide(I), copper bromide(II) or silver acetate.

6) The process according to any one of the above items 1) to 5), wherein the base is N-methylmorpholine, triethylamine, diisopropylethylamine, pyridine, DABCO, N,N-dimethylbenzylamine, N,N-dimethylaniline, sodium acetate, potassium carbonate, sodium carbonate or potassium phosphate.

7) The process according to any one of the above items 2) to 6), wherein the compound represented by Formula(II) is a compound represented by Formula(II'):

[Chemical Formula 12]

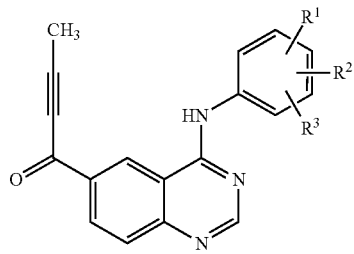

(II')

wherein $R^1$ is a hydrogen atom, halogen, substituted or unsubstituted alkyloxy, substituted or unsubstituted alkenyloxy, substituted or unsubstituted alkynyloxy or a group represented by formula: —Y—$R^y$, wherein —Y— is —O—, —S—, —SO$_2$—, or alkylene which may be intervened with —O—, —S— or —N($R^z$)—; $R^y$ is substituted or unsubstituted aromatic carbocyclyl or substituted or unsubstituted aromatic heterocyclyl; and $R^z$ is a hydrogen atom, substituted or unsubstituted alkyl, substituted or unsubstituted acyl, substituted or unsubstituted alkyloxycarbonyl, substituted or unsubstituted alkenyloxycarbonyl or substituted or unsubstituted aromatic carbocyclylalkyloxycarbonyl;

$R^2$ and $R^3$ are each independently a hydrogen atom, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, halogen, hydroxy, mercapto, cyano or substituted or unsubstituted amino.

8) The process according to the above item 7), wherein $R^1$ is a group represented by formula: —Y—$R^y$, wherein —Y— is alkylene which may be intervened with —O—; and $R^y$ is phenyl unsubstituted or substituted with a substituent selected from a substituent group p [substituent group p: halogen, carboxy, alkyl, haloalkyl, hydroxyalkyl, alkyloxy, alkyloxycarbonyl and substituted or unsubstituted amino], pyridyl unsubstituted or substituted with a substituent selected from a substituent group p, furyl unsubstituted or substituted with a substituent selected from a substituent group p, thienyl unsubstituted or substituted with a substituent selected from a substituent group p, thiazolyl unsubstituted or substituted with a substituent selected from a substituent group p, or oxazolyl unsubstituted or substituted with a substituent selected from a substituent group p;

$R^2$ is substituted or unsubstituted alkynyl, substituted or unsubstituted alkyloxy or halogen; and $R^3$ is a hydrogen atom.

9) The process according to the above items 7) or 8), wherein the compound represented by Formula (II') is a compound represented by Formula (II"):

[Chemical Formula 13]

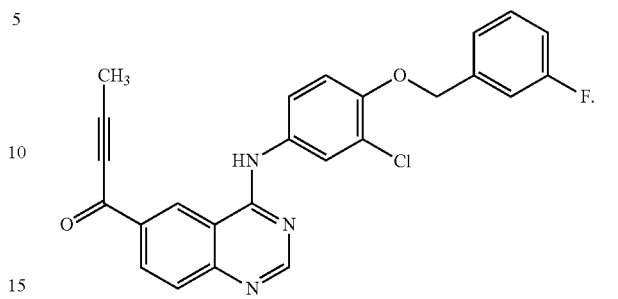

(II")

10) A methanesulfonate of the compound represented by Formula (II"):

[Chemical Formula 14]

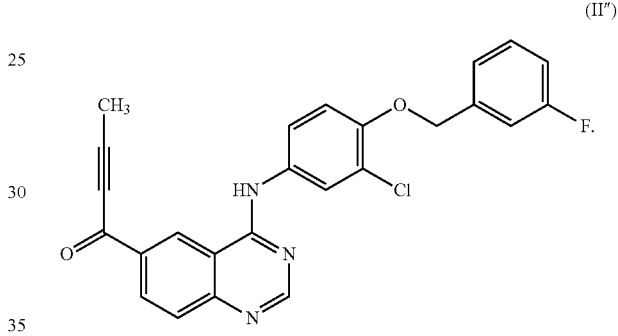

(II")

11) A crystalline form of methanesulfonate of the compound represented by Formula (II"):

[Chemical Formula 15]

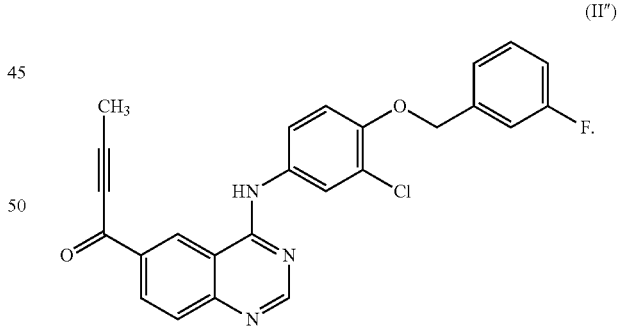

(II")

12) The crystalline form according to the above item 11), wherein diffraction angle 2θ of the powder X-Ray diffraction analysis are 5.6°±0.2°, 9.8°±0.2°, 17.9°±0.2°, 24.4°±0.2°, and 26.4°±0.2°.

13) The crystalline form according to the above item 11), wherein diffraction angle 2θ of the powder X-Ray diffraction analysis are 5.6°±0.2°, 8.3°±0.2°, 9.8°±0.2°, 13.7°±0.2°, 17.0°±0.2°, 17.9°±0.2°, 21.3°±0.2°, 24.4°±0.2°, 26.0°±0.2°, and 26.4°±0.2°.

14) A complex comprising N-methylmorpholine, hydroiodic acid and dimethylsulfoxide.

14') A complex represented by

[Chemical Formula 16]

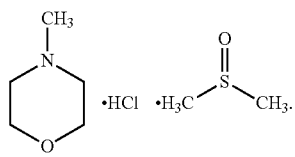

15) The complex according to the above items 14) or 14'), wherein the complex is a crystalline form.

16) The crystalline form of the complex according to the above item 15), wherein said crystalline form of the complex is characterized by the following crystal data:

TABLE 1

| Space Group | $P2_1/c$ |
| --- | --- |
| a (Å) | 7.3750(2) |
| b (Å) | 11.8395(3) |
| c (Å) | 14.2325(4) |
| α (°) | 90 |
| β (°) | 107.764(2) |
| γ (°) | 90 |
| V (Å$^3$) | 1183.47(5) |
| Z | 4 |
| Density(calculated value) (g/cm$^3$) | 1.724 |
| Measured temperature (° C.) | −173 |

17) The crystalline form of the complex according to the above item 15), wherein diffraction angle 2θ of the powder X-Ray diffraction analysis are 12.6°±0.2°, 16.9°±0.2°, 17.5°±0.2°, 26.3°±0.2°, and 28.9°±0.2°.

18) The crystalline form of the complex according to the above item 15), wherein diffraction angle 2θ of the powder X-Ray diffraction analysis are 12.6°±0.2°, 16.9°±0.2°, 17.5°±0.2°, 19.5°±0.2°, 20.8°±0.2°, 25.8°±0.2°, 26.3°±0.2°, 27.0°±0.2°, 28.4°±0.2°, and 28.9°±0.2°.

19) The process according to any one of the above items 1) to 5), wherein the compound represented by Formula(I) is a compound represented by Formula(I'):

[Chemical Formula 17]

wherein ring A is as defined in the above item 1), and the base is N-methylmorpholine, characterized in that the process is carried out in the presence of the crystalline form of the complex comprising N-methylmorpholine, hydroiodic acid and dimethylsulfoxide.

20) The process according to any one of the above items 2) to 5), wherein the compound represented by Formula (I) is a compound represented by Formula (I''):

[Chemical Formula 18]

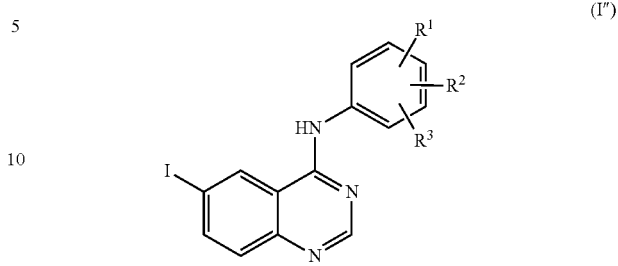

wherein, $R^1$, $R^2$ and $R^3$ are as defined in the above item 7), the base is N-methylmorpholine, and the compound represented by Formula (II) is the compound represented by Formula (II'):

[Chemical Formula 19]

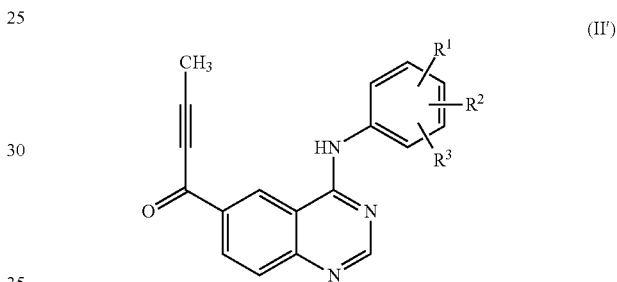

wherein $R^1$, $R^2$ and $R^3$ are as defined in the above item 7), characterized in that the process is carried out in the presence of the crystalline form of the complex comprising N-methylmorpholine, hydroiodic acid and dimethylsulfoxide.

21) The process according to any one of the above items 2) to 5), wherein the compound represented by Formula (I) is a compound represented by Formula (I'''):

[Chemical Formula 20]

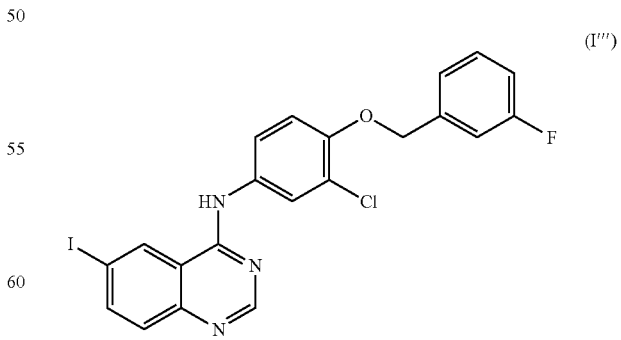

the base is N-methylmorpholine, and the compound represented by Formula (II) is the compound represented by Formula (II''):

[Chemical Formula 21]

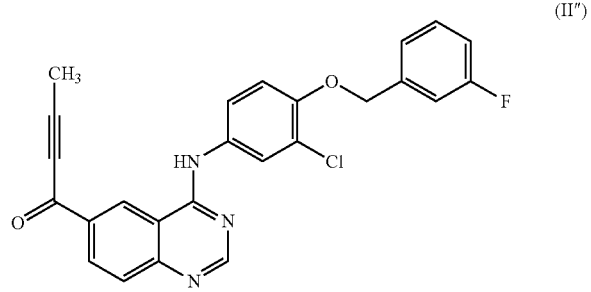

(II″)

characterized in that the process is carried out in the presence of the crystalline form of the complex comprising N-methylmorpholine, hydroiodic acid and dimethylsulfoxide.

22) The process according to any one of the above items 1) to 6) and 19), characterized in that the process is carried out in the presence of N,N-dimethylglycine, picolinic acid, L-proline, 2-hydroxy-N,N-diethyl-benzamide, ethylene glycol, ethyl 2-oxocyclohexanecarboxylate, 2-acetylcyclohexanone, 2-hydroxybenzoic acid, 2-furoic acid, diethyl malonate, N,N-dimethylethylenediamine, acetic acid, copper(I) 2-thiophenecarboxylate, glycine, N-methylglycine, D-proline, N-methylproline, imidazole-4-carboxylic acid, oxazole-4-carboxylic acid, thiazole-4-carboxylic acid, imidazole-2-carboxylic acid, oxazole-2-carboxylic acid, thiazole-2-carboxylic acid, pyrrole-2-carboxylic acid, isoxazole-5-carboxylic acid, isoxazole-3-carboxylic acid, alanine, valine, leucine, isoleucine, 2-dimethylaminobenzoic acid, glycolamide, formic acid, propionic acid, butyric acid, oxalic acid, maleic acid, trifluoroacetic acid, malonic ester, acetoacetic ester, ethylene glycol dimethyl ether, 2-methoxyethanol, glycolic acid, glycolic ester, 1,3-propanediol, 1,4-butanediol, 1,5-pentanediol, diethylene glycol, catechol, 2-hydroxymethyl-1,3-propanediol, N,N-dimethylurea, N,N-diphenylurea or N,N-dimethylglycinamide.

23) The process according to the above items 7), 8) or 20), characterized in that the process is carried out in the presence of N,N-dimethylglycine, picolinic acid, L-proline, 2-hydroxy-N,N-diethyl-benzamide, ethylene glycol, ethyl 2-oxocyclohexanecarboxylate, 2-acetylcyclohexanone, 2-hydroxybenzoic acid, 2-furoic acid, diethyl malonate, N,N-dimethylethylenediamine, acetic acid, copper(I) 2-thiophenecarboxylate, glycine, N-methylglycine, D-proline, N-methylproline, imidazole-4-carboxylic acid, oxazole-4-carboxylic acid, thiazole-4-carboxylic acid, imidazole-2-carboxylic acid, oxazole-2-carboxylic acid, thiazole-2-carboxylic acid, pyrrole-2-carboxylic acid, isoxazole-5-carboxylic acid, isoxazole-3-carboxylic acid, alanine, valine, leucine, isoleucine, 2-dimethylaminobenzoic acid, glycolamide, formic acid, propionic acid, butyric acid, oxalic acid, maleic acid, trifluoroacetic acid, malonic ester, acetoacetic ester, ethylene glycol dimethyl ether, 2-methoxyethanol, glycolic acid, glycolic ester, 1,3-propanediol, 1,4-butanediol, 1,5-pentanediol, diethylene glycol, catechol, 2-hydroxymethyl-1,3-propanediol, N,N-dimethylurea, N,N-diphenylurea or N,N-dimethylglycinamide.

24) The process according to the above item 9) or 21), characterized in that the process is carried out in the presence of N,N-dimethylglycine, picolinic acid, L-proline, 2-hydroxy-N,N-diethyl-benzamide, ethylene glycol, ethyl 2-oxocyclohexanecarboxylate, 2-acetylcyclohexanone, 2-hydroxybenzoic acid, 2-furoic acid, diethyl malonate, N,N-dimethylethylenediamine, acetic acid, copper(I) 2-thiophenecarboxylate, glycine, N-methylglycine, D-proline, N-methylproline, imidazole-4-carboxylic acid, oxazole-4-carboxylic acid, thiazole-4-carboxylic acid, imidazole-2-carboxylic acid, oxazole-2-carboxylic acid, thiazole-2-carboxylic acid, pyrrole-2-carboxylic acid, isoxazole-5-carboxylic acid, isoxazole-3-carboxylic acid, alanine, valine, leucine, isoleucine, 2-dimethylaminobenzoic acid, glycolamide, formic acid, propionic acid, butyric acid, oxalic acid, maleic acid, trifluoroacetic acid, malonic ester, acetoacetic ester, ethylene glycol dimethyl ether, 2-methoxyethanol, glycolic acid, glycolic ester, 1,3-propanediol, 1,4-butanediol, 1,5-pentanediol, diethylene glycol, catechol, 2-hydroxymethyl-1,3-propanediol, N,N-dimethylurea, N,N-diphenylurea or N,N-dimethylglycinamide.

25) A process for producing a compound represented by Formula (V):

[Chemical Formula 22]

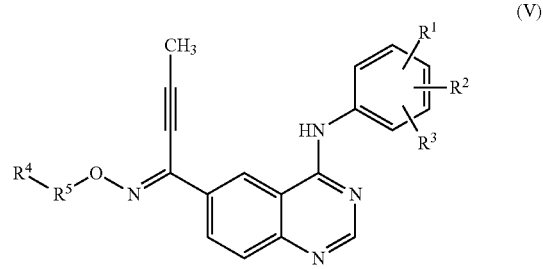

(V)

wherein $R^1$, $R^2$ and $R^3$ are as defined in the above item 7), $R^4$ is substituted or unsubstituted aromatic carbocyclyl, substituted or unsubstituted aromatic heterocyclyl, substituted or unsubstituted non-aromatic heterocyclyl or substituted or unsubstituted amino, and $R^5$ is substituted or unsubstituted C1 to 3 alkylene, characterized in that the compound represented by Formula (II') which is prepared by the process according to the above items 7), 8), 20) or 23),
is reacted with a compound represented by Formula(IV):
$R^4$—$R^5$—O—$NH_2$,
wherein $R^4$ and $R^5$ are as defined above.

26) A process for producing a compound represented by Formula(V'):

[Chemical Formula 23]

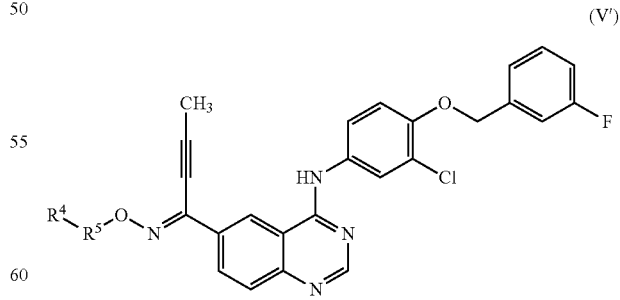

(V')

wherein $R^4$ is substituted or unsubstituted aromatic carbocyclyl, substituted or unsubstituted aromatic heterocyclyl, substituted or unsubstituted non-aromatic heterocyclyl or substituted or unsubstituted amino, and $R^5$ is substituted or unsubstituted C1 to 3 alkylene, characterized in that the compound represented by Formula (II″) which is prepared by the process according to the above items 9), 21) or 24),
is reacted with the compound represented by Formula(IV):
R⁴—R⁵—O—NH₂,
wherein R⁴ and R⁵ are as defined above.

27) The process according to any one of the above items 1) to 6), wherein ring A is a substituted or unsubstituted aromatic carbocycle.

28) The process according to any one of the above items 1) to 6) and 27), wherein ring A is substituted or unsubstituted benzene.

29) The process according to any one of the above items 1) to 6), wherein ring A is a substituted or unsubstituted aromatic heterocycle.

30) The process according to any one of the above items 1) to 6) and 29), wherein ring A is substituted or unsubstituted quinazoline, pyridine, thiazole, thiophene, imidazole, pyrazine, pyrimidine or furan.

31) The process according to the above item 19), wherein ring A is a substituted or unsubstituted aromatic carbocycle.

32) The process according to the above item 31), wherein ring A is substituted or unsubstituted benzene.

33) The process according to the above item 19), wherein ring A is a substituted or unsubstituted aromatic heterocycle.

34) The process according to the above item 33), wherein ring A is substituted or unsubstituted quinazoline, pyridine, thiazole, thiophene, imidazole, pyrazine, pyrimidine or furan.

35) The process according to the above item 22), wherein ring A is a substituted or unsubstituted aromatic carbocycle.

36) The process according to the above item 35), wherein ring A is substituted or unsubstituted benzene.

37) The process according to the above item 22), wherein ring A is a substituted or unsubstituted aromatic heterocycle.

38) The process according to the above item 37), wherein ring A is substituted or unsubstituted quinazoline, pyridine, thiazole, thiophene, imidazole, pyrazine, pyrimidine or furan.

39) Palladium cross coupling reaction characterized in that the reaction is carried out in the presence of N,N-dimethylglycine, picolinic acid, L-proline, 2-hydroxy-N,N-diethylbenzamide, ethylene glycol, ethyl 2-oxocyclohexanecarboxylate, 2-acetylcyclohexanone, 2-hydroxybenzoic acid, 2-furoic acid, diethyl malonate, N,N-dimethylethylenediamine, acetic acid, copper(I) 2-thiophenecarboxylate, glycine, N-methylglycine, D-proline, N-methylproline, imidazole-4-carboxylic acid, oxazole-4-carboxylic acid, thiazole-4-carboxylic acid, imidazole-2-carboxylic acid, oxazole-2-carboxylic acid, thiazole-2-carboxylic acid, pyrrole-2-carboxylic acid, isoxazole-5-carboxylic acid, isoxazole-3-carboxylic acid, alanine, valine, leucine, isoleucine, 2-dimethylaminobenzoic acid, glycolamide, formic acid, propionic acid, butyric acid, oxalic acid, maleic acid, trifluoroacetic acid, malonic ester, acetoacetic ester, ethylene glycol dimethyl ether, 2-methoxyethanol, glycolic acid, glycolic ester, 1,3-propanediol, 1,4-butanediol, 1,5-pentanediol, diethylene glycol, catechol, 2-hydroxymethyl-1,3-propanediol, N,N-dimethylurea, N,N-diphenylurea or N,N-dimethylglycinamide.

40) The reaction according to the above item 39), characterized in that the reaction is carried out in the presence of N,N-Dimethylglycine, Picolinic acid, L-Proline, 2-Hydroxy-N,N-diethyl-benzamide, Ethylene glycol, Ethyl 2-oxocyclohexanecarboxylate, 2-Acetylcyclohexanone, 2-Hydroxybenzoic acid, 2-Furoic acid, Diethyl malonate, N,N-Dimethylethylenediamine, Acetic acid or Copper(I) 2-thiophenecarboxylate.

41) The reaction according to the above items 39) or 40), characterized in that the reaction is carried out in the presence of N,N-Dimethylglycine, Picolinic acid or Ethylene glycol.

42) The reaction according to one of the above items 39) to 41), characterized in that the reaction is carried out in the presence of N,N-Dimethylglycine.

43) The reaction according to one of the above items 39) to 42), wherein palladium cross coupling reaction is Negishi, Heck, Suzuki, Sonogashira, Stille or Buchwald-Hartwig reaction.

Terms used in this description are explained below. Each term, unless otherwise indicated, has the same meaning when it is used alone or together with other terms.

As used herein, "leaving group" includes halogen, p-toluenesulfonyl, trifluoromethanesulfonyl and methanesulfonyl. Examples include halogen.

As used herein, "halogen" includes fluorine, chlorine, bromine and iodine.

As used herein, "alkyl" which is used alone or in combination with other term includes a straight or branched monovalent hydrocarbon group having 1 to 10 carbon atom(s). Examples include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl, n-nonanyl, n-decanyl and the like. Examples include C1-C10 alkyl. Examples include C1-C6 alkyl. Examples include C1-C4 alkyl.

As used herein, examples of "alkyloxy" include methyloxy, ethyloxy, n-propyloxy, isopropyloxy, n-butyloxy, isobutyloxy, sec-butyloxy, tert-butyloxy, n-pentyloxy, n-hexyloxy, n-heptyloxy, n-octyloxy, n-nonanyloxy, n-decanyloxy and the like. Examples include C1-C6 alkyloxy. Examples include C1-C3 alkyloxy.

As used herein, examples of "alkyloxycarbonyl" include methyloxycarbonyl, ethyloxycarbonyl, n-propyloxycarbonyl, isopropyloxycarbonyl, n-butyloxycarbonyl, t-butyloxycarbonyl, n-pentyloxycarbonyl and the like. Examples include C1-C6 alkyloxycarbonyl. Examples include C1-C3 alkyloxycarbonyl.

As used herein, the above "alkyl" which is substituted with the above "halogen" at 1 to 8 positions, or 1 to 5 positions for example is included. Examples include trifluoromethyl, trichloromethyl, difluoroethyl, trifluoroethyl, dichloroethyl, trichloroethyl and the like. Examples include C1-C6 alkyl which is substituted with above "halogen" at 1 to 5 positions.

As used herein, "alkenyl" includes a straight or branched monovalent hydrocarbon group having 2 to 8 carbon atoms and 1 or 2 or more double bond(s). The alkenyl may have a triple bond in a chain. Examples include vinyl, allyl, 1-propenyl, 2-propenyl, various butenyl isomers and the like. Examples include C2-C6 alkenyl. Examples include C2-C4 alkenyl.

As used herein, examples of "alkenyloxy" include vinyloxy, allyloxy, 1-propenyloxy, 2-propenyloxy, various butenyloxys and the like. Examples include C2-C6 alkenyloxy. Examples include C2-C4 alkenyloxy.

As used herein, examples of "alkenyloxycarbonyl" include vinyloxycarbonyl, allyloxycarbonyl, 1-propenyloxycarbonyl, 2-propenyloxycarbonyl, various butenyloxycarbonyls and the like. Examples include C2-C6 alkenyloxycarbonyl. Examples include C2-C4 alkenyloxycarbonyl.

As used herein, "alkynyl" includes a straight or branched monovalent hydrocarbon group having 2 to 8 carbon atoms and having 1 or 2 or more triple bond(s). Examples include ethynyl, 1-propynyl, 2-propynyl, 1-butynyl, 2-butynyl, 3-butynyl, 1-pentynyl, 2-pentynyl, various pentynyl isomers and the like. Examples include C2-C6 alkynyl. Examples include C2-C4 alkynyl.

As used herein, examples of "alkynyloxy" include ethynyloxy, propynyloxy, butynyloxy, pentynyloxy and the like. Examples include C2-C6 alkynyloxy. Examples include C2-C4 alkynyloxy.

As used herein, "alkylene" which is used alone or in combination with other term includes a straight or branched divalent hydrocarbon group having 1 to 4 carbon atom(s). Examples include methylene, ethylene, propylene, butylene and the like. Examples include C1-C3 alkylene. Examples include C1-C2 alkylene.

As used herein, "aromatic carbocyclyl" which is used alone or in combination with other term includes a monocyclic or fused cyclic aromatic hydrocarbon. Examples include phenyl, 1-naphthyl, 2-naphthyl, anthryl and the like. Examples include phenyl, 1-naphthyl and 2-naphthyl. Examples include phenyl.

As used herein, "aromatic carbocycle" includes a ring which is derived from the above "aromatic carbocyclyl" and which may have a bond at a substitutable arbitrary position. Examples include benzene, naphthalene and anthracene. Examples include benzene.

As used herein, "aralkyl" includes the above "alkyl" substituted with one or two or more of the above "aromatic carbocyclyl", and these can be substituted at all possible positions. Examples include benzyl, phenylethyl (e.g. 2-phenylethyl, and the like), phenylpropyl (e.g. 3-phenylpropyl, and the like), naphthylmethyl (e.g. 1-naphthylmethyl, 2-naphthylmethyl, and the like), anthrylmethyl (e.g. 9-anthrylmethyl, and the like) and the like. Examples include benzyl and phenylethyl.

As used herein, "aromatic heterocyclyl" which is used alone, or in combination with other term includes a 5- to 6-membered aromatic ring group containing one or more of arbitrarily selected oxygen atom, sulfur atom or nitrogen atom in a ring. This may be fused with the "aromatic carbocyclyl" or aromatic heterocyclyl at all possible positions. When an aromatic heterocycle is any of a monocycle and a fused cycle, it can bind at all possible positions. Examples include pyrrolyl (e.g. 1-pyrrolyl, 2-pyrrolyl, 3-pyrrolyl), furyl (e.g. 2-furyl, 3-furyl), thienyl (e.g. 2-thienyl, 3-thienyl), imidazolyl (e.g. 2-imidazolyl, 4-imidazolyl), pyrazolyl (e.g. 1-pyrazolyl, 3-pyrazolyl), isothiazolyl (e.g. 3-isothiazolyl), isoxazolyl (e.g. 3-isooxazolyl), oxazolyl (e.g. 2-oxazolyl), thiazolyl (e.g. 2-thiazolyl, 5-thiazolyl), pyridyl (e.g. 2-pyridyl, 3-pyridyl, 4-pyridyl), pyrazinyl (e.g. 2-pyrazinyl), pyrimidinyl (e.g. 2-pyrimidinyl, 4-pyrimidinyl), pyridazinyl (e.g. 3-pyridazinyl), triazolyl, tetrazolyl (e.g. 1H-tetrazolyl), oxadiazolyl (e.g. 1, 3, 4-oxadiazolyl), thiadiazolyl (e.g. 1, 3, 4-thiadiazolyl), indolizinyl (e.g. 2-indolizinyl, 6-indolizinyl), isoindolyl (e.g. 2-isoindolyl), indolyl (e.g. 1-indolyl, 2-indolyl, 3-indolyl), indazolyl (e.g. 3-indazolyl), purinyl (e.g. 8-purinyl), quinolizinyl (e.g. 2-quinolizinyl), isoquinolyl (e.g. 3-isoquinolyl), quinolyl (e.g. 2-quinolyl, 5-quinolyl), phthalazinyl (e.g. 1-phthalazinyl), naphthyridinyl (e.g. 2-naphthyridinyl), quinazolinyl (e.g. 2-quinazolinyl), cinnolinyl (e.g. 3-cinnolinyl), pteridinyl (e.g. 2-pteridinyl), carbazolyl (e.g. 2-carbazolyl, 4-carbazolyl), phenanthridinyl (e.g. 2-phenanthridinyl, 3-phenanthridinyl), acridinyl (e.g. 1-acridinyl, 2-acridinyl), dibenzofuranyl (e.g. 1-dibenzofuranyl, 2-dibenzofuranyl), benzoimidazolyl (e.g. 2-benzoimidazolyl), benzoisoxazolyl (e.g. 3-benzoisooxazolyl), benzoxazolyl (e.g. 2-benzooxazolyl), benzoxadiazolyl (e.g. 4-benzooxadiazolyl), benzoisothiazolyl (e.g. 3-benzoisothiazolyl), benzothiazolyl (e.g. 2-benzothiazolyl), benzofuryl (e.g. 3-benzofuryl), benzothienyl (e.g. 2-benzothienyl), 4, 5-dihydronaphtho[1, 2-d]thiazolyl, 4H-chromeno[4, 3-d]thiazolyl, 4H-thiochromeno[4, 3-d]thiazolyl, 4, 5-dihydrothiazolo[5, 4-c]quinolyl, 8H-indeno[1, 2-d]thiazolyl, 5, 6-dihydro-4H-3-thia-1-azabenzo[e]azulenyl and the like.

As used herein, "aromatic heterocycle" includes a ring which is derived from the above "aromatic heterocyclyl" and which may have a bond at a substitutable arbitrary position. Examples include pyrrole, furan, thiophene, imidazole, pyrazole, isothiazole, isoxazole, oxazole, thiazole, pyridine, pyrazine, pyrimidine, pyridazine, triazole, tetrazole, oxadiazole, thiadiazole, indolizine, isoindolizine, indole, indazole, purine, quinolizine, phthalazine, naphthyridine, quinazoline, cinnoline, pteridine, carbazole, phenanthridine, acridine, dibenzofuran, benzoimidazole, benzoisoxazole, benzoxazole, benzoxadiazole, benzoisothiazole, benzothiazole, benzofuran, benzothiophene, and the like. Examples include quinazoline.

As used herein, the term "non-aromatic heterocyclyl" which is used alone, or in combination with other term includes a non-aromatic 5- to 7-membered ring containing one or more arbitrary selected from an oxygen atom, a sulfur atom and a nitrogen atom in a ring, and a group derived from a ring in which other one or more "non-aromatic heterocycle" or "aromatic heterocycle" is fused thereto. Examples include pyrrolidinyl (e.g. 1-pyrrolidinyl, 2-pyrolidinyl), pyrrolinyl (e.g. 3-pyrrolinyl), imidazolidinyl (e.g. 2-imidazolidinyl), imidazolinyl (e.g. imidazolinyl), pyrazolidinyl (e.g. 1-pyrazolidinyl, 2-pyrazolidinyl), pyrazolinyl (e.g. pyrazolinyl), piperidyl (e.g. piperidino, 2-piperidyl), piperazinyl (e.g. 1-piperazinyl, 2-piperazinyl), indolinyl (e.g. 1-indolinyl), isoindolinyl (e.g. isoindolinyl), morpholinyl (e.g. morpholino, 2-morpholinyl, 3-morpholinyl), tetrahydrofuranyl, dihydropyranyl, tetrahydropyranyl, dioxolanyl, tetrahydrothienyl, dihydrothiopyranyl, tetrahydrothiofuranyl, decahydroisoquinolinyl, azepinyl, oxepinyl, dihydroxepinyl, tetrahydroxepinyl, oxepanyl, 4, 5, 6, 7-tetrahydrothieno[3, 2]pyridyl, 2-oxa-5-aza-bicyclo[2.2.1]hepta-5-yl, hexahydropyrazyl[2.1-b][1, 3]oxadin-8-yl and the like.

As used herein, "non-aromatic carbocyclyl" includes a cyclic saturated hydrocarbon group or a cyclic unsaturated non-aromatic hydrocarbon group, which is monocyclic or polycyclic having two or more rings. Examples of "non-aromatic carbocyclyl", which is polycyclic having two or more rings, include a fused ring group wherein a non-aromatic carbocyclyl, which is monocyclic or polycyclic having two or more rings, is fused with a ring of the above "aromatic carbocyclyl".

In addition, examples of "non-aromatic carbocyclyl" also include a group having a bridge or a group to form a Spiro ring as follows:

[Chemical Formula 24]

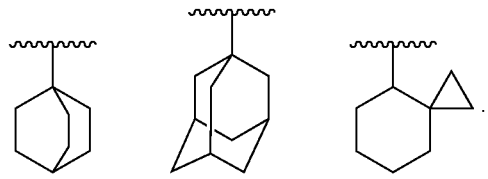

The non-aromatic carbocyclyl which is monocyclic is preferably C3 to C16, more preferably C3 to C12 and further preferably C4 to C8 carbocyclyl. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, cyclohexadienyl and the like.

Examples of non-aromatic carbocyclyl, which is polycyclic having two or more rings, include indanyl, indenyl, acenaphthyl, tetrahydronaphthyl, fluorenyl and the like.

As used herein, "acyl" include formyl, alkylcarbonyl in which the alkyl part is the above "alkyl", haloalkylcarbonyl in which the haloalkyl part is the above "haloalkyl", alkenylcarbonyl in which the alkenyl part is the above "alkenyl", aralkylcarbonyl in which the aralkyl part is the above "aralkyl", aromatic carbocyclylcarbonyl in which the aromatic carbocycle part is the above "aromatic carbocyclyl", aromatic heterocyclylcarbonyl in which the aromatic heterocycle part is the above "aromatic heterocyclyl", non-aromatic heterocyclylcarbonyl in which the non-aromatic heterocycle part is the above "non-aromatic heterocyclyl" and non-aromatic carbocyclylcarbonyl in which the non-aromatic carbocycle part is the "non-aromatic carbocyclyl". Examples include acetyl, propionyl, butyroyl, trifluoromethylcarbonyl, vinylcarbonyl, phenylacetyl, benzoyl and the like. The "alkyl", the "alkenyl", the "aralkyl", the "aromatic carbocyclyl", the "aromatic heterocyclyl", the "non-aromatic heterocyclyl" and the "non-aromatic carbocyclyl" may be substituted with each substituent described below.

As used herein, alkyl in "hydroxyalkyl", "alkylcarbonyl", "alkylthio", and "alkylsulfonyl" is the "alkyl" as defined above.

As used herein, alkyloxycarbonyl in "aromatic carbocyclylalkyloxycarbonyl" is the "alkyloxycarbonyl" as defined above.

As used herein, aromatic carbocycle part in "aromatic carbocyclylalkyloxycarbonyl", "aromatic carbocyclyloxycarbonyl", "aromatic carbocyclylcarbonyloxy", "aromatic carbocyclylcarbonyl", "aromatic carbocyclylthio", "aromatic carbocyclylsulfonyl" and "aromatic carbocyclyloxy" is the "aromatic carbocyclyl" as defined above.

As used herein, non-aromatic carbocycle part in "non-aromatic carbocyclyloxycarbonyl", "non-aromatic carbocyclylcarbonyloxy", "non-aromatic carbocyclylcarbonyl", "non-aromatic carbocyclylthio", "non-aromatic carbocyclylsulfonyl" and "non-aromatic carbocyclyloxy" is the "non-aromatic carbocyclyl" as defined above.

As used herein, aromatic heterocycle part in "aromatic heterocyclyloxycarbonyl", "aromatic heterocyclylcarbonyloxy", "aromatic heterocyclylcarbonyl", "aromatic heterocyclylthio", "aromatic heterocyclylsulfonyl", "aromatic heterocyclyloxy" is the "aromatic heterocyclyl" as defined above.

As used herein, non-aromatic heterocycle part in "non-aromatic heterocyclyloxycarbonyl", "non-aromatic heterocyclylcarbonyloxy", "non-aromatic heterocyclylcarbonyl", "non-aromatic heterocyclylthio", "non-aromatic heterocyclylsulfonyl" and "non-aromatic heterocyclyloxy" is the "non-aromatic heterocyclyl" as defined above.

A substituent in the "substituted aromatic heterocycle", "substituted aromatic carbocycle", "substituted alkyl", "substituted alkenyl", "substituted alkynyl", "substituted alkyloxy", "substituted alkyloxycarbonyl", "substituted alkenyloxy", "substituted alkenyloxycarbonyl", "substituted alkynyloxy", "substituted aromatic carbocyclylalkyloxycarbonyl", "substituted alkylene", "substituted aromatic carbocyclyl", "substituted non-aromatic carbocyclyl", "substituted aromatic heterocyclyl, "substituted non-aromatic heterocyclyl, "substituted acyl" and "substituted amino" is selected from the group consisting of hydroxy, carboxy, halogen, haloalkyl (e.g. $CF_3$, $CH_2CF_3$, $CH_2CCl_3$), alkyl (e.g. methyl, ethyl, isopropyl, tert-butyl), alkenyl (e.g. vinyl), alkynyl (e.g. ethynyl), non-aromatic carbocyclyl (e.g. cyclopropyl, cyclopropenyl), alkyloxy (e.g. methoxy, ethoxy, propoxy, butoxy), haloalkyloxy (e.g. $OCF_3$), alkenyloxy (e.g. vinyloxy, allyloxy), aromatic carbocyclyloxy (e.g. phenoxy), alkoxycarbonyl (e.g. methoxycarbonyl, ethoxycarbonyl, tert-butoxycarbonyl), nitro, nitroso, optionally substituted amino (e.g. alkylamino (e.g. methylamino, ethylamino, dimethylamino), acylamino (e.g. acetylamino, benzoylamino), aralkylamino (e.g. benzylamino, tritylamino), hydroxyamino, alkoxycarbonylamino, alkylsulfonylamino, carbamoylamino, non-aromatic heterocyclylcarbonylamino, aromatic carbocyclylsulfonylamino), azido, aromatic carbocyclyl(e.g. phenyl), aralkyl(e.g. benzyl), cyano, isocyano, isocyanato, thiocyanato, isothiocyanato, mercapto, alkylthio (e.g. methylthio), alkylsulfonyl (e.g. methanesulfonyl, ethanesulfonyl), alkylsulfonyloxy (e.g. methanesulfonyloxy, ethanesulfonyloxy), optionally substituted carbamoyl (e.g. alkylcarbamoyl (e.g. methylcarbamoyl, ethylcarbamoyl, dimethylcarbamoyl), alkylsulfonylcarbamoyl), sulfamoyl, acyl (e.g. formyl, acetyl), formyloxy, haloformyl, oxalo, thioformyl, thiocarboxy, dithiocarboxy, thiocarbamoyl, sulfino, sulfo, sulfonyl, sulfinyl, sulfoamino, hydrazino, azido, ureido, amidino, guanidino, phthalimide, oxo, non-aromatic carbocyclyl, aromatic carbocyclyl, aromatic heterocyclyl, non-aromatic heterocyclyl, alkylene, optionally substituted alkylene dioxy(—O—$CH_2$—O—, —O—$CH_2$—$CH_2$—O—, —O—$CH_2$—$CH_2$—$CH_2$—O— and the like), aromatic carbocyclyloxy, non-aromatic carbocyclyloxy, aromatic heterocyclyloxy, non-aromatic heterocyclyloxy, alkyloxycarbonyl, aromatic carbocyclyloxycarbonyl, non-aromatic carbocyclyloxycarbonyl, aromatic heterocyclyloxycarbonyl, non-aromatic heterocyclyloxycarbonyl, alkylcarbonyloxy, aromatic carbocyclylcarbonyloxy, non-aromatic carbocyclylcarbonyloxy, aromatic heterocyclylcarbonyloxy, non-aromatic heterocyclylcarbonyloxy, alkylcarbonyl, aromatic carbocyclylcarbonyl, non-aromatic carbocyclylcarbonyl, aromatic heterocyclylcarbonyl, non-aromatic heterocyclylcarbonyl, alkylthio, aromatic carbocyclylthio, non-aromatic carbocyclylthio, aromatic heterocyclylthio, non-aromatic heterocyclylthio, alkylsulfonyl, aromatic carbocyclylsulfonyl, non-aromatic carbocyclylsulfonyl, aromatic heterocyclylsulfonyl, non-aromatic heterocyclylsulfonyl, thiocarbamoyl, sulfamoyl and the like. These can be substituted with 1 to 4 substituent(s).

As used herein, "substituted or unsubstituted aromatic heterocycle" in ring A is exemplified by quinazoline, pyridine, thiazole, thiophene, imidazole, pyrazine, pyrimidine or furan. "Substituted or unsubstituted aromatic carbocycle" in ring A is exemplified by benzene.

As used herein, the leaving group in X is exemplified by iodine.

As used herein, R is exemplified by methyl.

As used herein, $R^1$ is exemplified by a group of the formula: —Y—$R^y$ wherein —Y— is alkylene which may be intervened with —O—; and $R^y$ is phenyl unsubstituted or substituted with a substituent selected from a group p [substituent group p: halogen, carboxy, alkyl, haloalkyl, hydroxyalkyl, alkyloxy, alkyloxycarbonyl and substituted or unsubstituted amino], pyridyl unsubstituted or substituted with a substituent selected from a group p, furyl unsubstituted or substituted with a substituent selected from a group p, thienyl unsubstituted or substituted with a substituent selected from a group p, thiazolyl unsubstituted or substituted with a substituent selected from a group p, and oxazolyl unsubstituted or substituted with a substituent selected from a group p.

As used herein, $R^1$ is exemplified by a group of the formula: —Y—$R^y$ wherein —Y— is alkylene which may be intervened with —O—; and $R^y$ is phenyl unsubstituted or substituted with a substituent selected from a group p consisting of [halogen, carboxy, alkyl, haloalkyl, hydroxyalkyl, alkyloxy, alkyloxycarbonyl and substituted or unsubstituted amino].

As used herein, $R^1$ is exemplified by a group of the formula: —Y—$R^y$ wherein —Y— is C1-C3 alkylene which may be intervened with —O—; and $R^y$ is phenyl unsubstituted or substituted with halogen.

As used herein, $R^2$ is exemplified by a hydrogen atom or halogen.

As used herein, $R^3$ is exemplified by a hydrogen atom or halogen.

As used herein, $R^4$ is exemplified by substituted or unsubstituted non-aromatic heterocyclyl or substituted or unsubstituted amino.

As used herein, $R^4$ is exemplified by substituted or unsubstituted non-aromatic heterocyclyl.

As used herein, "non-aromatic heterocyclyl" in $R^4$ is exemplified by morpholinyl, pyrrolidinyl, piperazinyl.

As used herein, a substituent of "substituted amino" in $R^4$ is exemplified by alkyl (hydroxyalkyl, alkyloxyalkyl), non-aromatic carbocyclyl and the like.

As used herein, a substituent of "substituted non-aromatic heterocyclyl" in $R^4$ is exemplified by hydroxyl and the like.

As used herein, $R^5$ is exemplified by substituted or unsubstituted C1 to C3 alkylene.

As used herein, $R^5$ is exemplified by unsubstituted C1 to C3 alkylene.

As used herein, $R^5$ is exemplified by substituted or unsubstituted C1 to C2 alkylene.

As used herein, $R^5$ is exemplified by unsubstituted C1 to C2 alkylene.

Herein, "the compound of Formula (I)", "the compound of Formula (I')", "the compound of Formula (I")", "the compound of Formula (I''')", "the compound of Formula (II)", "the compound of Formula (II')", "the compound of Formula (II")", "the compound of Formula (III)", "the compound of Formula (IV)", "the compound of Formula (V)" and "the compound of Formula (V')" may be converted to its salt form. Examples include salts of alkali metals (lithium, sodium, potassium and the like), salts of alkaline-earth metals (calcium, barium and the like), salts of magnesium, salts of transition metal (zinc, iron and the like), salts of ammonium, salts of organic bases (trimethylamine, triethylamine, dicycohexylamine, ethanolamine, diethanolamine, triethanolamine, meglumine, diethanolamine, ethylenediamine, pyridine, picoline, quinoline and the like), and salts of amino acid, or salts of inorganic acids (hydrochloric acid, sulfuric acid, nitric acid, carbonic acid, hydrobromic acid, phosphoric acid, hydroiodic acid and the like), and salts of organic acids (formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid and the like). Especially, examples include salts of hydrochloric acid, sulfuric acid, phosphoric acid, tartaric acid, methanesulfonic acid and the like. The compound is converted to its salt form by the conventional method.

Also, the said compound may form a solvate. A solvate herein includes, for example, a solvate (e.g. hydrates and the like) and/or crystal polymorphs, and the present invention encompasses those various solvates and crystal polymorphs. "Solvates" may be those wherein any numbers of solvent molecules (e.g. water molecules and the like) are coordinated with the said compounds. When the said compounds or the salt thereof are allowed to stand in the atmosphere, the compounds or the salt thereof may absorb water, resulting in attachment of adsorbed water or formation of hydrates. Recrystallization of the said compounds or the salt thereof may produce crystal polymorphs of them.

Effect of Invention

The compounds represented by Formula (II), (II') and (II") which are useful as synthetic intermediates can be prepared by Sonogashira-carbonylation reaction. Also, the compounds represented by Formula (II), (II') and (II") can be prepared via fewer steps compared to the heretofore known production process (Patent Document 1 and Patent Document 2), and it is an excellent method for industrial application.

Also, Sonogashira-carbonylation reaction in the presence of crystals of the new compound of the present invention can control the reaction heat, whereas the exponential increase of heat flow may constitute a potential danger in the large scale synthesis.

Furthermore, Sonogashira-carbonylation reaction in the presence of appropriate ligands (additives) can inhibit the precipitates of the palladium black in the reaction pot.

Moreover, the new crystal of the compound represented by Formula (II") can be used as an intermediate of useful medicines.

BRIEF DESCRIPTION OF DRAWINGS

FIG. 1 indicates data of powder X-Ray diffraction analysis pattern of the crystalline form of Compound 3 (methane sulfonate of the compound represented by Formula (II")).

FIG. 2 indicates a crystal configuration in the asymmetric unit of Compound 4 (the complex comprising N-methylmorpholine, hydroiodic acid and dimethylsulfoxide).

FIG. 3 indicates data of powder X-Ray diffraction analysis pattern of the crystalline form of Compound 4 (the complex comprising N-methylmorpholine, hydroiodic acid and dimethylsulfoxide).

FIG. 4 indicates data of DSC analysis of the crystalline form of Compound 4 (the complex comprising N-methylmorpholine, hydroiodic acid and dimethylsulfoxide).

FIG. 5 indicates the reaction heat flow of Sonogashira-carbonylation reaction in the absence of the crystalline form of the complex comprising N-methylmorpholine, hydroiodic acid and dimethylsulfoxide.

FIG. 6 indicates the reaction heat flow of Sonogashira-carbonylation reaction in the presence of the crystalline form of the complex comprising N-methylmorpholine, hydroiodic acid and dimethylsulfoxide.

FIG. 7 indicates data of TG/DTA analysis of the crystalline form of Compound 4 (the complex comprising N-methylmorpholine, hydroiodic acid and dimethylsulfoxide).

EMBODIMENTS FOR CARRYING OUT THE INVENTION

The present invention comprises the process for producing a compound represented by Formula (II):

[Chemical Formula 25]

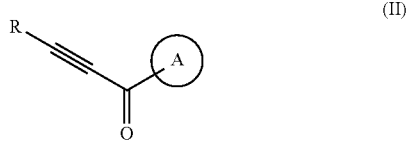

(II)

wherein, a ring A is a substituted or unsubstituted aromatic heterocycle or a substituted or unsubstituted aromatic carbocycle; R is a hydrogen atom or methyl; characterized by reacting a compound represented by Formula (I);

[Chemical Formula 26]

(I)

wherein ring A is as defined above, X is a leaving group, with carbon monoxide and a compound represented by Formula (III);

[Chemical Formula 27]

(III)

wherein, R is as defined above,
in the presence of a palladium catalyst, a phosphine ligand, a catalyst comprising Group 11 element and a base.

The compound represented by Formula (I) which is a starting material can be prepared in accordance with the method described in Patent Document 1. Also, it can be prepared in accordance with the conventional method from commercially available reagents or it is possible to use commercially available products.

Examples of a solvent, which is not limited as far as it does not inhibit the reaction, include dimethylacetamide (DMA), tetrahydrofuran (THF), dimethylsulfoxide (DMSO) and the mixed solvent thereof. For example, a mixed solvent of tetrahydrofuran and dimethylsulfoxide can be used.

The reaction temperature is usually in the range of room temperature to the reflux temperature of the solvent. For example, the reaction can be carried out in the range of −10° C. to 60° C. For example, the reaction can be carried out in the range of −20° C. to 30° C.

The amount of the compound represented by Formula (III) used is usually 1.0 to 5.0 equivalent(s), for example, 2.0 to 3.0 equivalents, for example, 2.2 to 2.5 equivalents, relative to the compound represented by Formula (I).

The method to apply the compound represented by Formula (III) into the reaction vessel can be carried out by bubbling. Alternatively, a solution can be applied to the reaction vessel in which the solution is prepared by dissolving the compound represented by Formula (III) into a solvent in advance.

The time to apply the compound represented by Formula (III) into the reaction vessel is usually over 0.2 to 10 hour(s), for example, 6 to 8 hours in the large scale synthesis.

The method to apply carbon monoxide into the reaction vessel can be carried out by replacing the atmosphere in the reaction vessel with carbon monoxide before starting the reaction. Alternatively, carbon monoxide can be applied by bubbling.

As for the pressure in the reaction vessel, the reaction can be carried out in both cases under atmospheric pressure and under increased pressure. When the reaction is carried out under increased pressure, the pressure in the reaction vessel is, for example, 0.01 to 0.5 MPa, for example, 0.1 to 0.3 MPa.

$Pd_2(dba)_3$, $PdCl_2$ dppf, $PdCl_2(PPh_3)_2$, $Pd(OAc)_2$, $Pd(PPh_3)_4$, Pd/C, $PdCl_2$, Pd-PEPPSI™-IPr, Bis[cinnamyl palladium Cl], $PdCl_2$ (Xantphos), $Pd(OH)_2$ and the like can be used as palladium catalyst. The commercially available palladium catalysts for various cross coupling reaction (Negishi, Heck, Suzuki, Sonogashira, Stille, Buchwald-Hartwig and the like) can be used. Also, a palladium catalyst can be prepared by the conventional method from a precursor of palladium catalyst. For example, the following palladium catalysts can be used.

$Pd_2(dba)_3$: Tris(dibenzylideneacetone)dipalladium(0),
$PdCl_2$ dppf: [1,1'-Bis(diphenylphosphino)ferrocene]palladium(II) dichloride dichloromethane adduct,
$PdCl_2$ $(PPh_3)_2$: Bis(triphenylphosphine)palladium(II) dichloride,
$Pd(OAc)_2$: Palladium(II) diacetate,
$Pd(PPh_3)_4$: Tetrakis(triphenylphosphine)palladium(0),
Pd/C: Palladium on carbon,
$PdCl_2$: Palladium(II) chloride,
Pd-PEPPSI™-IPr: [1,3-Bis(2,6-diisopropylphenyl)imidazol-2-ylidene](3-chloropyridyl)palladium(II) dichloride,
Bis[cinnamyl palladium Cl: Bis[cinnamyl palladium(II) chloride],
$PdCl_2$(Xantphos): Dichloro[9,9-dimethyl-4,5-bis(diphenylphosphino)xanthene]palladium(II),
$Pd(OH)_2$: Palladium hydroxide.

Examples include $PdCl_2$ dppf, $PdCl_2(PPh_3)_2$, $Pd_2(dba)_3$ and $Pd(OAc)_2$.

For example, $Pd_2(dba)_3$ is exemplified.

The amount of the palladium catalyst used is usually catalytic amount, relative to the compound represented by Formula (I), for example, 0.001 to 0.1 equivalent, for example, 0.001 to 0.01 equivalent.

Xantphos, $P(2-furyl)_3$, $PPh_3$, $P(o-tol)_3$, $P(OPh)_3$, $P(OMe)_3$, dppp, dppb, dppf, BINAP, X-Phos, $P(t-Bu)_3$, $P(Oi-Pr)_3$, $P(p-MeOPh)_3$, DPEPhos and the like can be used as phosphine ligand. The commercially available phosphine ligands for various cross coupling reaction (Negishi, Heck, Suzuki, Sonogashira, Stille, Buchwald-Hartwig and the like) can be used. Also, a phosphine ligand can be prepared by the conventional method from a precursor of phosphine ligand. For example, the following phosphine ligands can be used.

Xantphos: 4,5-Bis(diphenylphosphino)-9,9-dimethylxanthene,
$P(2-furyl)_3$: Tri(2-furyl)phosphine,
$PPh_3$: Triphenylphosphine,
$P(o-tol)_3$: Tri(o-tolyl)phosphine,
$P(OPh)_3$: Triphenyl phosphite,
$P(OMe)_3$: Trimethyl phosphite,
dppp: 1,3-Bis(diphenylphosphino)propane,
dppb: 1,4-Bis(diphenylphosphino)butane,
dppf: 1,1'-Bis(diphenylphosphino)ferrocene,
BINAP: 2,2'-Bis(diphenylphosphino)-1,1'-binaphthyl,
X-Phos: 2-Dicyclohexylphosphino-2',4',6'-triisopropylbiphenyl,
$P(t-Bu)_3$: Tri-tert-butylphosphine,
$P(Oi-Pr)_3$: Triisopropyl phosphite,
$P(p-MeOPh)_3$: Tris(4-methoxyphenyl)phosphine, DPEPhos: Bis[2-(diphenylphosphino)phenyl] Ether.

Examples include PPh$_3$, P(o-tol)$_3$, P(OPh)$_3$, P(2-furyl)$_3$ and Xantphos.

For example, Xantphos is exemplified.

The amount of the phosphine ligand used is usually catalytic amount, relative to the compound represented by Formula (I), for example, 0.001 to 0.1 equivalent, for example, 0.01 to 0.03 equivalent.

Copper, silver and gold are exemplified as Group 11 element.

Examples include copper iodide(I), copper iodide(II), copper chloride(I), copper chloride(II), copper acetate(I), copper acetate(II), copper oxide(II), copper bromide(I), copper bromide(II) or silver acetate as the catalyst comprising Group 11 element.

For example, copper chloride(I), copper acetate(I) and copper bromide(I) are exemplified.

For example, copper chloride(I) is exemplified.

The amount of the catalyst comprising Group 11 element used is usually catalytic amount, relative to the compound represented by Formula (I), for example, 0.001 to 0.5 equivalent, for example, 0.01 to 0.1 equivalent.

Examples include N-methylmorpholine, triethylamine, diisopropylethylamine, pyridine, DABCO(1,4-Diazabicyclo [2.2.2]octane), N,N-dimethylbenzylamine, N,N-dimethylaniline, sodium acetate, potassium carbonate, sodium carbonate or potassium phosphate, metal hydride (e.g. sodium hydride and the like), metal alkoxide (e.g. sodium methoxide, sodium ethoxide, potassium t-butoxide and the like), metallic sodium, alkyllithium(n-BuLi, sec-BuLi, tert-BuLi) and the like as the base.

Examples include N-methylmorpholine, triethylamine, diisopropylethylamine, pyridine, DABCO(1,4-Diazabicyclo [2.2.2]octane), N,N-dimethylbenzylamine, N,N-dimethylaniline, sodium acetate, potassium carbonate, sodium carbonate or potassium phosphate as the base.

For example, N-methylmorpholine, triethylamine, diisopropylethylamine and pyridine are exemplified.

For example, N-methylmorpholine is exemplified.

The amount of the base used is usually 2 to 10 equivalents, relative to the compound represented by Formula (I), for example, 2 to 8 equivalents, for example, 3 to 5 equivalents.

The above process can be carried out in the presence of N,N-dimethylglycine, picolinic acid, L-proline, 2-hydroxy-N,N-diethyl-benzamide, ethylene glycol, ethyl 2-oxocyclohexanecarboxylate, 2-acetylcyclohexanone, 2-hydroxybenzoic acid, 2-furoic acid, diethyl malonate, N,N-dimethylethylenediamine, acetic acid, copper(I) 2-thiophenecarboxylate, glycine, N-methylglycine, D-proline, N-methylproline, imidazole-4-carboxylic acid, oxazole-4-carboxylic acid, thiazole-4-carboxylic acid, imidazole-2-carboxylic acid, oxazole-2-carboxylic acid, thiazole-2-carboxylic acid, pyrrole-2-carboxylic acid, isoxazole-5-carboxylic acid, isoxazole-3-carboxylic acid, alanine, valine, leucine, isoleucine, 2-dimethylaminobenzoic acid, glycolamide, formic acid, propionic acid, butyric acid, oxalic acid, maleic acid, trifluoroacetic acid, malonic ester, acetoacetic ester, ethylene glycol dimethyl ether, 2-methoxyethanol, glycolic acid, glycolic ester, 1,3-propanediol, 1,4-butanediol, 1,5-pentanediol, diethylene glycol, catechol, 2-hydroxymethyl-1,3-propanediol, N,N-dimethylurea, N,N-diphenylurea or N,N-dimethylglycinamide.

For example, the process can be carried out in the presence of N,N-dimethylglycine, picolinic acid, L-proline, 2-hydroxy-N,N-diethyl-benzamide, ethylene glycol, ethyl 2-oxocyclohexanecarboxylate, 2-acetylcyclohexanone, 2-hydroxybenzoic acid, 2-furoic acid, diethyl malonate, N,N-dimethylethylenediamine, acetic acid, copper(I) 2-thiophenecarboxylate.

For example, the process can be carried out in the presence of N,N-dimethylglycine, picolinic acid or ethylene glycol.

For example, the process can be carried out in the presence of N,N-dimethylglycine.

The above process can be carried out in both cases in the presence and in the absence of the said compounds.

The amount of the said compound used is usually catalytic amount, relative to the compound represented by Formula (I), for example, 0.01 to 0.5 equivalent, for example, 0.02 to 0.1 equivalent in which the process is carried out in the presence of the said compound.

As hereinafter referred to Example 3, the said compound can control the deactivation of palladium catalyst when the process is carried out in the presence of the said compound.

Additionally, the said compound can be used for other reactions (e.g. Negishi Heck, Suzuki, Sonogashira, Stille, Buchwald-Hartwigh and the like) by using palladium catalyst other than Sonogashira-carbonylation reaction of the present invention.

In the above process, when the compound represented by Formula (I) is the compound represented by Formula (I'):

[Chemical Formula 28]

wherein, ring A is as defined above, the compound represented by Formula (I"):

[Chemcial Formula 29]

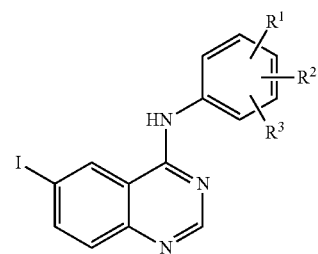

wherein, $R^1$, $R^2$ and $R^3$ are as defined above, or the compound represented by Formula (I'''):

[Chemical Formula 30]

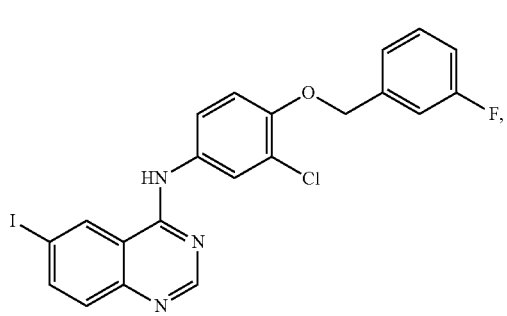

(I''')

and the base is N-methylmorpholine, the process can be carried out even in the presence of the crystalline form of the complex comprising N-methylmorpholine, hydroiodic acid and dimethylsulfoxide.

The above process can be carried out in both cases in the presence and in the absence of the crystalline form of the complex comprising N-methylmorpholine, hydroiodic acid and dimethylsulfoxide.

When the above process is carried out in the presence of the crystalline form of the complex comprising N-methylmorpholine, hydroiodic acid and dimethylsulfoxide, the crystalline form of the said complex used is usually 0.1 to 61%, for example, 1 to 10%, for example 2 to 4%, relative to the compound represented by Formula (I'), Formula (I'') or Formula (I''').

As hereinafter referred to Example 1, when the above process is carried out in the presence of the crystalline form of the complex comprising N-methylmorpholine, hydroiodic acid and dimethylsulfoxide, it can prevent the exponential increase of reaction heat.

As used herein, the complex includes crystalline form and amorphous form.

As used herein, "the crystalline form of the complex comprising N-methylmorpholine, hydroiodic acid and dimethylsulfoxide" includes the crystalline form of the complex comprising N-methylmorpholine hydroiodide and dimethylsulfoxide solvate.

Additionally, as used herein, "the crystalline form of the complex comprising N-methylmorpholine, hydroiodic acid and dimethylsulfoxide" includes the co-crystal comprising N-methylmorpholine hydroiodide and dimethylsulfoxide solvate.

When the compound represented by Formula (II) is the following compound:

[Chemical Formual 31]

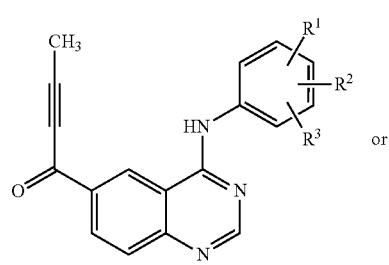

(II')

or

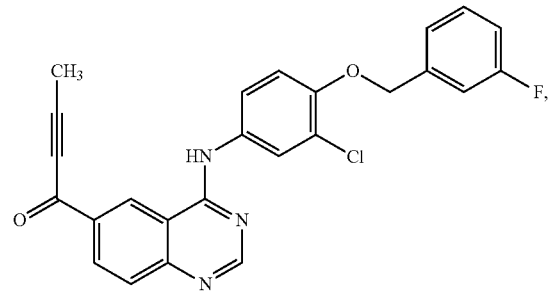

(II'')

the process can be carried out in the same manner as the above reaction condition. When ring A of the compound represented by Formula (II) is a substituted or unsubstituted aromatic heterocycle (e.g, benzene or the like) or a substituted or unsubstituted aromatic carbocycle (e.g, quinazoline, pyridine, thiazole, thiophene, imidazole, pyrazine, pyrimidine, furan or the like), the process can be carried out in the same manner as the above reaction condition.

Also, the present invention includes methanesulfonate of the compound represented by Formula (II'') or a step to obtain the crystalline form of it.

Methanesulfonate of the compound represented by Formula (II'') or the crystalline form of it can be prepared by adding methanesulfonic acid to the reaction solution after completion of the reaction of the above process.

Examples of a solvent include the solvent which is used in the above process. Also, another solvent can be added after completion of the reaction of the above process. Examples include acetonitrile and tetrahydrofuran. For example, acetonitrile can be used.

The reaction temperature is in the range of −10° C. to 40° C. For example, the reaction temperature is in the range of −5° C. to 25° C.

The amount of methanesulfonic acid used is usually 2 to 10 equivalents, for example, 3 to 8 equivalents, for example 4.0 to 5.5 equivalents, relative to the compound represented by Formula (I''').

The present invention includes a step that methanesulfonate of the compound represented by Formula (II'') or the crystalline form of it is converted to a free form of the compound represented by Formula (II''). The free form of the compound represented by Formula (II'') can be prepared by treating methanesulfonate of the compound represented by Formula (II'') or the crystalline form of it with a base.

Examples of the solvent, which is not limited as far as it does not inhibit the reaction, include methanol, ethanol, isopropanol and the like. For example, methanol is exemplified.

The reaction temperature is in the range of −20° C. to 40° C. For example, the reaction temperature is in the range of −5° C. to 10° C.

Examples of the base include the base which is used in the above process. For example, N-methylmorpholine can be used.

The amount of the base used is usually 1 to 5 equivalent(s), for example, 1 to 3 equivalent(s), for example 1 to 1.5 equivalent(s), relative to methanesulfonate of the compound represented by Formula (II'') or the crystalline form of it.

Moreover, the present invention includes a step to prepare the crystalline form of the complex comprising N-methylmorpholine, hydroiodic acid and dimethylsulfoxide.

The commercially available N-methylmorpholine, hydroiodic acid (aqueous solution is preferred) and dimethylsulfoxide (DMSO) can be used as the starting materials.

Examples of the solvent, which is not limited as far as it does not inhibit the reaction, include tetrahydrofuran (THF), dimethylsulfoxide (DMSO) and a mixed solvent of them.

The reaction temperature is usually in the range of −20° C. to 70° C., for example, in the range of 0° C. to 30° C., for example, in the range of 5° C. to 25° C.

The amount of hydroiodic acid (aqueous solution) used is usually 1.0 to 2 equivalent(s), for example, 1.0 to 1.5 equivalent(s), for example, 1.0 to 1.1 equivalent, relative to N-methylmorpholine.

The amount of dimethylsulfoxide (DMSO) used is usually the amount of solvent, relative to N-methylmorpholine. For example, the amount of 80% to 3000%, for example, 80% to 800% can be used.

As an alternative method, the crystalline form of the complex comprising N-methylmorpholine, hydroiodic acid and dimethylsulfoxide can be obtained as by-product by Sonogashira-carbonylation reaction described above using the compound represented by Formula (I'), Formula (I") or Formula (I''') as the starting material, N-methylmorpholine as the base, dimethylsulfoxide or a mixed solvent [for example, a mixed solvent with tetrahydrofuran (THF)], and it can be used in the above process.

Hereinafter, methods for identifying the crystalline form of the present invention are explained.

Unless otherwise noted, the numerical values described and claimed herein are approximate. Variation within the values may be attributed to equipment calibration, equipment errors, purity of the materials, crystal size, and sample size, among other factors.

As used herein, "crystalline" or "crystal" means a substance having an ordered atom, ion, molecule and the like that consists a solid, thereby the substance has periodism and anisotropism. The degree of crystallinity of crystalline form can be determined by many techniques including, for example, powder X-ray diffraction, moisture sorption, differential scanning calorimetry, solution calorimetry, and dissolution properties.

In general, crystalline organic compounds consist of a large number of atoms that are arranged in a periodic array in three-dimensional space. The structural periodicity normally manifests physical properties, which can be explicitly distinguished by most spectroscopic probes (e.g., X-ray diffraction, an infrared spectrum, a Raman spectrum and solid state NMR).

The X-ray powder diffraction (XRPD) is acknowledged to be one of the most sensitive analytical methods for measuring solid crystallinity. X-rays which are irradiated to crystals are reflected by the crystal lattice planes and mutually interfere. Then, only the diffraction lines in the direction which fulfill the conditions predicted by Bragg's law are intensified and the ordered diffraction lines corresponding to the periodicity of the structure are observed. On the other hand, in the case of amorphous solids, the well-ordered diffraction lines over a long-range are not observed. Amorphous solids usually show broad XRPD patterns called halo patterns, because they do not have the ordered iteration periodicity in the structure, so that the diffraction phenomenon does not occur.

The crystalline form of methanesulfonate of the compound represented by Formula (II") and the crystalline form of complex comprising N-methylmorpholine, hydroiodic acid and dimethylsulfoxide, which are disclosed in this description, have X-ray powder diffraction profiles.

For example, the crystalline form can be specified by the presence of characteristic diffraction peaks. The characteristic diffraction peaks used in this description are the ones selected from the observed diffraction peaks. The characteristic diffraction peaks are selected from preferably about 20, more preferably about 10, and most preferably about 5 peaks in a diffraction pattern.

Since an error in the range of ±0.2° may occur in diffraction angles (2θ) in X-ray powder diffraction, in general, the value of the above diffraction angle should be understood as the one including values in a range of around ±0.2°. Therefore, the present invention includes not only crystalline forms whose diffraction angles of the peaks in X ray powder diffraction perfectly match, but also crystalline forms whose diffraction angles of the peaks match within an error of around ±0.2°.

In general, it is known that the relative intensities of the peaks shown in the Tables and Figures below may vary due to a number of factors such as selected orientation effects of crystals in the X-ray beam, effect of coarse particle, purity of the material being analyzed or degree of crystallinity of the sample, for example. The peak positions may also shift for variations in sample height. Furthermore, measurements using a different wavelength will result in different shifts according to the Bragg equation ($n\lambda = 2d \sin \theta$). Such another XPRD patterns obtained by using a different wavelength are also within the scope of the present invention.

Single crystal X-ray analysis is one of the most popular analytical method to identify the crystalline form, as described in Manual of X-ray structural analysis (1983), Sakurai Toshio: Shokabo Press, Stout & Jensen, X-Ray Structure Determination: A Practical Guide, Macmillan Co., New York (1968). The method can provide crystal parameters and atomic coordinates (the positions of individual atoms in a crystal) which can be graphically represented. Therefore, the method is useful to identify the crystalline form of this invention.

The crystalline form of methanesulfonate of the compound represented by Formula (II") and the crystalline form of complex comprising N-methylmorpholine, hydroiodic acid and dimethylsulfoxide, which are prepared in the above process, are stable and easy to handle for conducting the above process, so that both crystalline forms are useful crystals as intermediate for producing the pharmaceutical composition.

The crystalline form of the present invention can be specified by thermal analysis methods.

Hereinafter, DSC (differential scanning calorimetry), one of the main measuring methods for thermal analysis, is a method of measuring the thermal properties of the substance as an aggregate of an atom(s) and a molecule(s).

A differential scanning calorimetry curve can be obtained by measuring temperatures or change of heat capacity over time of a pharmaceutical active ingredient by DSC, and plotting the obtained data to temperatures or times. From a differential scanning calorimetry curve, the information about the onset temperature, melting endothermic maximum and enthalpy of a pharmaceutical active ingredient can be obtained.

As to DSC, it is known that the observed temperature can depend on rate of temperature change, the sample preparations techniques or the specific devices. Therefore, in DSC, "the melting point" means the onset temperature which is unaffected by technique for preparing the sample. The error span in the onset temperature obtained from a differential scanning calorimetry curve is approximately ±2° C. In specifying the identity of a crystal, overall pattern is important and may change somewhat depending on a measurement condition.

Hereinafter, TG/DTA (Themogravimeter Differential Thermal Analyzer) is one of the major measuring methods of thermal analysis. It is a method of measuring the weight and the thermal property of a substance as an aggregate of atoms and molecules.

TG/DTA is the method of measuring the changes in weight and quantity of heat of an active pharmaceutical ingredient concerning the temperature or the time. TG (thermo gravity) and DTA (Differential Thermal Analysis) curve are obtained by plotting the obtained data against temperature or time. TG/DTA curve provides the information about the changes in weight and quantity of heat related to decomposition, dehydration, oxidation, reduction, sublimation and evaporation of an active pharmaceutical ingredient.

It is known that the temperature and the weight changes observed in TG/DTA may depend on a heating rate, a sample preparation technique and a specific device. Therefore, in TG/DTA, a "melting point" means onset temperature which is unaffected by technique for preparing the sample. In specifying the identity of a crystal, overall pattern is important and may change somewhat depending on a measurement condition.

The present invention is explained in more detail by the following Examples, but these Examples do not limit the present invention. Although an effort to guarantee accuracy about numerical values (for example, quantity, temperature, etc.) is paid, some errors and deviations should be taken into consideration. If not shown in particular, % is weight % of a component, and weight % is weight % of the full weight of a composition. A pressure is an atmospheric pressure or a pressure near it.

Terms used in the present description are explained below:
g: gram
L: liter
mg: milligram
mL: milliliter
MeCN: acetonitrile
DMSO: dimethylsulfoxide
THF: tetrahydrofuran
DMA: dimethylacetamide
MsOH: methanesulfonic acid
NMM: N-methylmorpholine
CO: carbon monoxide
rt: room temperature
HPLC: High Performance Liquid Chromatography
(Powder X-Ray Diffraction Measurement)

Data of powder X-ray diffraction measurement of the obtained crystalline form in each Example is obtained according to powder X-ray diffraction analysis method in General tests in Japanese Pharmacopoeia as following conditions.
(Method A)
(Device)
RINT-TTRIII by Rigaku
(Operation Method)
Samples were measured under the following conditions.
Measuring method: Reflection method
Light source: Cu tube
Used Wavelength: CuKα ray
Tube current: 300 mA
Tube voltage: 50 kV
Sampling plate: Aluminum
X-ray incident angle (θ): 2-40°
Sampling range: 0.020°
(Method B)
(Device)
D-8 Discover by Bruker
(Operation Method)
Samples were measured under the following conditions.
Measuring method: Reflection method
Light source: Cu tube
Used Wavelength: CuKα ray
Tube current: 40 mA
Tube voltage: 40 kV
Sampling plate: glass
X-ray incident angle (θ): 3-40°
(The Single Crystal X-Ray Analysis)

All measurements were made on a Rigaku R-AXIS RAPID diffractometer using graphite monochromated Cu—Kα radiation (λ=1.54187 Å). During the measurements, the crystals were kept in dark environment and kept frozen in nitrogen gas stream (−173° C.). Data integration was carried out using the RAPID AUTO software package (Rigaku, 2006). The data were corrected for the Lorentz, polarization and absorption effects.

The structure was solved by direct methods using the program SHELXS-97 (Sheldrick, 2008), and the structural refinement was carried out by fullmatrix least-squares of F2 using the program SHELXL-97 (Sheldrick, 2008). All non-hydrogen atoms were refined with anisotropic displacement parameters. All other hydrogen atoms were placed in the idealized positions using the riding mode in SHELXL-97. The hydrogen bonded to nitrogen (N1) was located using the difference Fourier maps. The final refinement converged to R1 (I>2.00 s(I))=0.0532. It was confirmed that no atom was misplaced or missing in the final difference Fourier map.

FIG. 2 shows the displacement ellipsoid plot (50% probability level) using the PLUTON (Spek, 1991)/ORTEP (Johnson, 1976).
(DSC Measurement)

About 1 mg of the crystalline form obtained in each Example was weighted, stuffed in a high pressure pan made of gold-plated steal and measured under sealed system. The measurement conditions were as follows.
(Measurement Condition)
Device: DSC822e by Mettler Toledo
Measurement temperature range: 25° C.-300° C.
Rate of temperature increase: 10° C./min
(TG/DTA Measurement)

About 10 mg of the crystalline form obtained in each Example was weighted, stuffed in aluminum pan and measured under open system. The measurement conditions were as follows.
(Measurement Condition)
Device: TG/DTA 7200 by Hitachi High-Tech Science
Measurement temperature range: 30° C.-300° C.
Rate of temperature increase: 10° C./min
(NMR Measurement)

In NMR data shown in Examples and Reference Examples, not all measured peaks may be described.
(HPLC Measurement)
(Method A)
Column: Unison UK-C18, φ4.6×150 mm, 3 μm (Imtakt)
Flow rate: 1.0 mL/min
UV detection wavelength: 246 nm Mobile phase A: Aqueous solution of 0.01 mol/L ammonium acetate (pH5.0)

Mobile phase B: Acetonitrile for HPLC

Gradient program is shown in Table 2.

TABLE 2

| Time after injection(min) | Mobile phase A (vol %) | Mobile phase B (vol %) |
|---|---|---|
| 0 to 10 | 40 | 60 |
| 10 to 20 | 40→10 | 60→90 |
| 20 to 25 | 10 | 90 |
| 25 to 25.1 | 10→40 | 90→60 |
| 25.1 to 30 | 40 | 60 |

(Method B)

Column: Unison UK-C18, φ4.6×150 mm, 3 μm (Imtakt)

Flow rate: 1.0 mL/min

UV detection wavelength: 246 nm

Mobile phase A: Aqueous solution of 0.01 mol/L ammonium acetate (pH5.0)

Mobile phase B: Acetonitrile for HPLC

Gradient program for purity measurement is shown in Table 3.

TABLE 3

| Time after injection(min) | Mobile phase A (vol %) | Mobile phase B (vol %) |
|---|---|---|
| 0 to 10 | 40 | 60 |
| 10 to 20 | 40→10 | 60→90 |
| 20 to 25 | 10 | 90 |
| 25 to 25.1 | 10→5 | 90→95 |
| 25.1 to 35 | 5 | 95 |
| 35 to 35.1 | 5→40 | 95→60 |
| 35.1 to 45 | 40 | 60 |

In the meantime, a retention time of HPLC should be construed as including some error.

Example 1

Synthesis of Compound 2

[Chemical Formula 32]

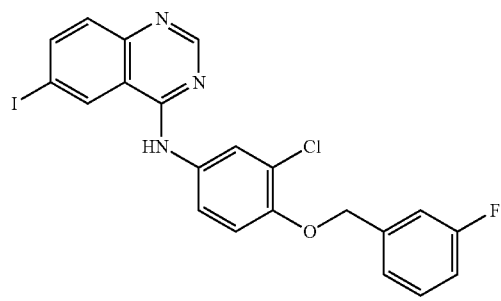

1

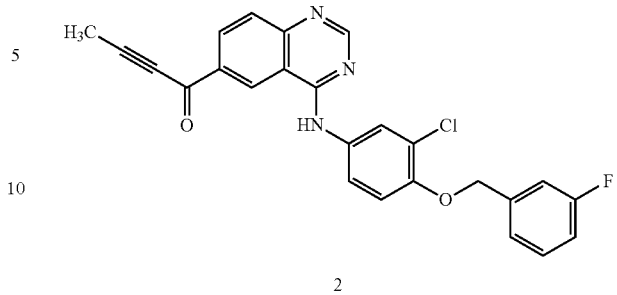

2

To aryl iodine compound (1) (4.04 g), $Pd_2(dba)_3$ (36.6 mg, 0.005 equivalent), Xantphos (92.6 mg, 0.02 equivalent) and CuCl (15.8 mg, 0.02 equivalent) were added tetrahydrofuran (6 mL), N-methylmorpholine (4.04 g, 5 equivalents) and dimethylsulfoxide (2 mL), successively. The slurry was stirred at 25° C. under carbon monoxide atmosphere, and about 2 mol/L of the solution in which propyne gas (2.2 equivalents) was preliminarily dissolved in tetrahydrofuran was added to the slurry over about 0.5 hours and the resulting slurry was stirred for about 19 hours. After completion of the reaction, the atmosphere in the vessel was replaced with nitrogen gas and acetonitrile (40.4 mL) was added to the slurry. The slurry was stirred at 0° C. for about 1 hour, filtered through and the obtained crystalline form was washed with cold acetonitrile (12.1 mL) to give Compound (2) (3.38 g, Yield 95%, Purity 81% (HPLC Method B)).

$^1$H-NMR (300 MHz, DMSO-$D_6$) δ: 10.33 (1.0H, s), 9.22 (1.1H, d, J=1.7 Hz), 8.65 (0.8H, s), 8.43 (1.1H, dd, J=8.6, 1.7 Hz), 7.98 (0.9H, d, J=2.4 Hz), 7.87 (0.9H, d, J=8.6 Hz), 7.71 (1.0H, dd, J=9.0, 2.4 Hz), 7.47 (1.0H, ddd, J=8.0, 8.0, 5.8 Hz), 7.34-7.30 (2.0H, m), 7.28 (1.0H, d, J=9.0), 7.21-7.14 (0.9H, m), 5.27 (2.0H, s), 2.28 (2.9H, s).

Elemental Analysis:

calculated value: C, 67.34; H, 3.84; N, 9.42; Cl, 7.95; F, 4.26 measured value: C, 67.24; H, 3.92; N, 9.39; Cl, 7.81; F, 4.26

Example 2

Synthesis of Compound 2

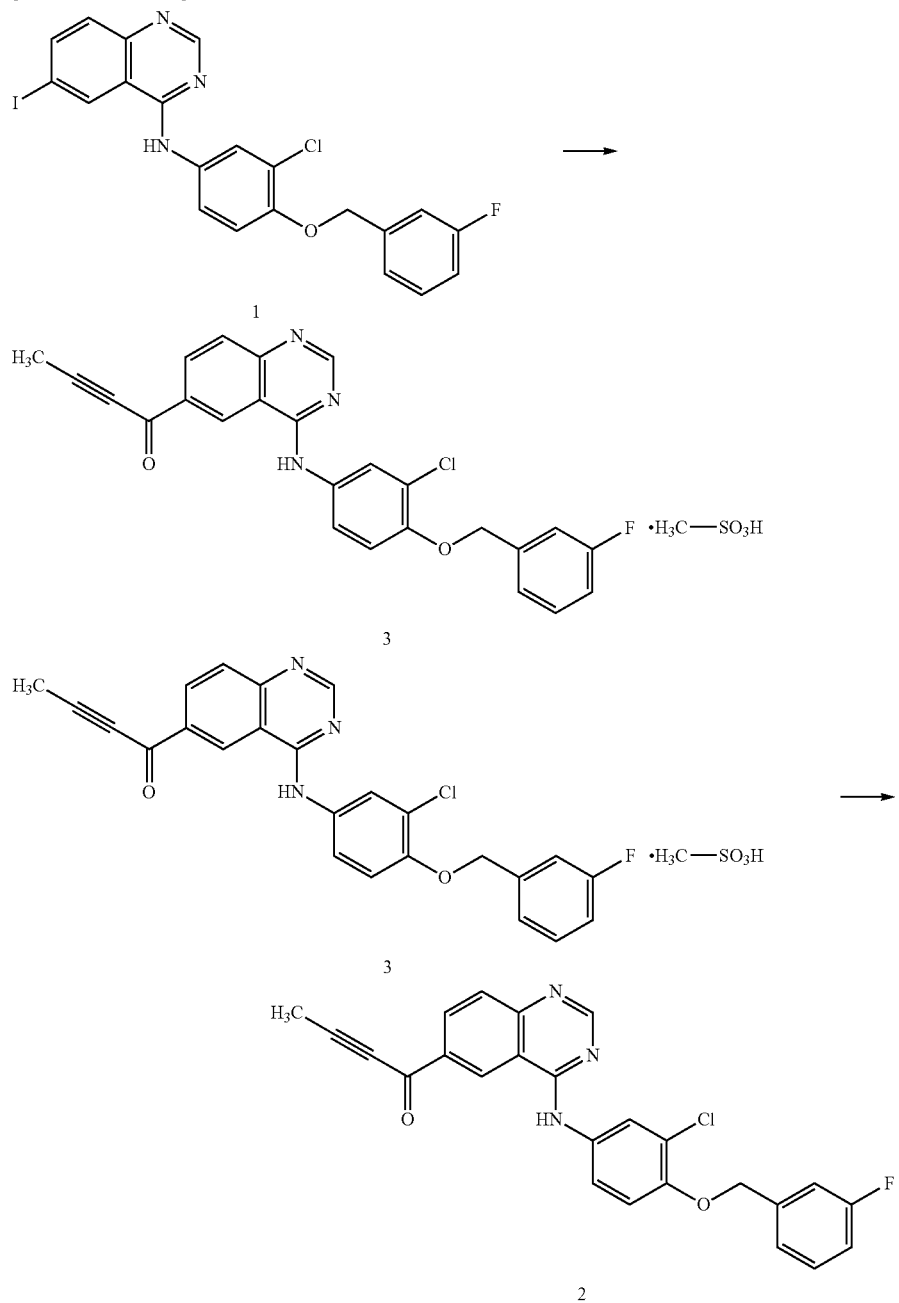

Step 1 Synthesis of Compound 3

To aryl iodine compound (1) (50.0 kg), Pd$_2$(dba)$_3$ (0.68 kg, 0.0075 equivalent), Xantphos (1.72 kg, 0.03 equivalent), CuCl (0.59 kg, 0.06 equivalent), Compound (4) (1.5 kg) obtained in Example 4 hereinafter described and N,N-dimethylglycine (0.41 kg, 0.04 equivalent) were added tetrahydrofuran (110 L), N-methylmorpholine (40 kg, 4 equivalents) and dimethylsulfoxide (25 L), successively under nitrogen atmosphere. The slurry was stirred at 25° C. under carbon monoxide atmosphere and propyne gas (9.1 kg, 2.3 equivalents) was applied for the vessel over about 7 hours, and stirred further for about 5 hours. After completion of the reaction, the vessel was replaced with nitrogen gas, and to the slurry were added acetonitrile (500 L) at 20° C., then methanesulfonic acid (47.5 kg, 5 equivalents) at 5° C. After the slurry was stirred for 1 hour, the resulting crystalline form was filtered and washed with acetonitrile (250 L) to give Compound (3).

$^1$H-NMR (DMSO-D$_6$) δ: 11.62 (0.7H, brs), 9.33 (1.2H, s), 8.94 (1.1H, s), 8.63 (1.1H, d, J=8.6 Hz), 7.96 (2.0H, d, J=8.6

Hz), 7.90 (2.0H, d, J=2.3 Hz), 7.63 (1.1H, dd, J=8.9, 2.3 Hz), 7.48 (0.9H, ddd, J=7.8, 7.8, 6.3 Hz), 7.36 (1.0H, d, J=8.9 Hz), 7.34-7.30 (2.0H, m), 7.22-7.16 (0.8H, m), 5.31 (2.0H, s), 2.32 (2.4H, s), 2.29 (3.0H, s)

The results of the powder X-ray diffraction were indicated in FIG. 1 and Table 4 (XRPD Method A).

TABLE 4

| 2θ |
|---|
| 5.620 |
| 8.280 |
| 9.760 |
| 13.740 |
| 14.520 |
| 16.460 |
| 16.960 |
| 17.860 |
| 18.320 |
| 19.240 |
| 19.760 |

TABLE 4-continued

| 2θ |
|---|
| 20.500 |
| 21.260 |
| 21.760 |
| 22.600 |
| 23.080 |
| 24.420 |
| 25.960 |
| 26.360 |
| 27.840 |
| 29.120 |
| 36.720 |

Diffraction angles of major peaks (2θ): 5.6°±0.2°, 9.8°±0.2°, 17.9°±0.2°, 24.4°±0.2°, 26.4°±0.2°.

Step 2 Synthesis of Compound 2

To Compound (3) obtained in the step 1 was added methanol (475 L), and N-methylmorpholine (11.0 kg, 1.1 equivalent) was added dropwise to the slurry at 0° C. After the slurry was stirred for about 1 hour, the resulting crystalline form was filtered and washed with cold methanol to give Compound (2) (41.4 kg, Yield 94%, Purity 93% (HPLC Method B)).

Example 3

Synthesis of Compound 3

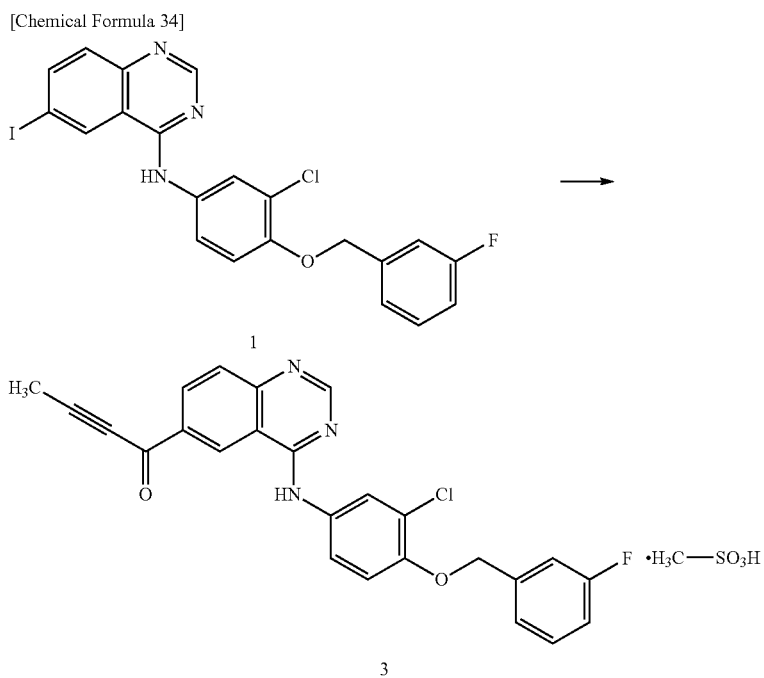

To aryl iodine compound (1) (27.5 g), Pd$_2$(dba)$_3$ (374 mg, 0.0075 equivalent), Xantphos (943 mg, 0.03 equivalent), CuCl (323 mg, 0.06 equivalent) and N,N-dimethylglycine (224 mg, 0.04 equivalent) were added tetrahydrofuran (60.5 mL), N-methylmorpholine (22.0 g, 4 equivalents) and dimethylsulfoxide (13.8 mL), successively. The slurry was stirred at 25° C. under carbon monoxide atmosphere and propyne gas (2.2 equivalents) was applied for the vessel over about 7 hours, and stirred further for about 1 hour. After completion of the reaction, the vessel was replaced with nitrogen gas, and to the slurry were added acetonitrile (303 mL) at 20° C., then methanesulfonic acid (26.1 g, 5 equivalents) at 5° C. After stood overnight, the slurry was stirred at −5° C. for 1 hour, and the resulting crystalline form was filtered and washed with cold acetonitrile (138 mL) to give Compound 3 (26.65 g, Yield 90%, Purity 88% (HPLC method B)).

Example 4

Synthesis of Compound 4

[Chemical Formula 35]

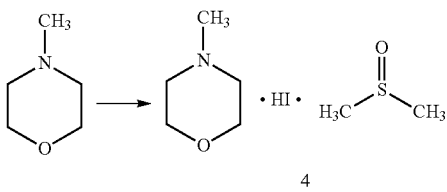

4

To N-methylmorpholine (1.12 kg) were added tetrahydrofuran (4.98 kg) and dimethylsulfoxide (7.40 kg), and 57% solution of hydroiodic acid (2.48 kg, 1.0 equivalent) was added dropwise to the solution between 10° C. and 20° C. After the slurry was stirred for about 15 minutes, tetrahydrofuran (9.96 kg) was added. The slurry was stirred for about 40 minutes, the resulting crystalline form was filtered and washed with tetrahydrofuran (4.48 kg) to give Compound 4 (3.00 kg, Yield 88%).

$^1$H-NMR (CD$_3$OD) δ: 3.92 (4H, brs), 3.48 (4H, brs), 2.94 (3H, s), 2.67 (6H, s)

Elemental Analysis:

calculated value: C, 27.37; H, 5.91; N, 4.56; S, 10.44; I, 41.31 measured value: C, 26.83; H, 5.76; N, 4.76; S, 10.41; I, 40.76

The crystal data was indicated in Table 5.

TABLE 5

| Space Group | P2$_1$/c |
|---|---|
| a (Å) | 7.3750(2) |
| b (Å) | 11.8395(3) |
| c (Å) | 14.2325(4) |
| α (°) | 90 |
| β (°) | 107.764(2) |
| γ (°) | 90 |
| V (Å$^3$) | 1183.47(5) |
| Z | 4 |
| Density(calculated value) (g/cm$^3$) | 1.724 |
| Measured temperature (° C.) | −173 | wherein, V indicates the unit lattice volume, Z indicates chemical unit number per unit cell.

In addition, the atomic coordinates of non-hydrogen atoms were indicated in Table 6 and that of hydrogen atoms were indicated in Table 7.

TABLE 6

| atom | x | y | z | B$_{eq}$ |
|---|---|---|---|---|
| I1 | −0.11884(4) | 0.73719(3) | 1.08563(2) | 1.54(2) |
| S1 | 0.2359(2) | 0.6634(1) | 0.88739(9) | 1.77(3) |
| O1 | 0.6214(4) | 0.4722(4) | 0.6416(3) | 2.06(7) |
| O2 | 0.3496(5) | 0.6078(4) | 0.8276(3) | 2.07(7) |
| N1 | 0.2607(5) | 0.4596(4) | 0.6767(3) | 1.14(7) |
| C1 | 0.4030(6) | 0.3653(5) | 0.7046(4) | 1.57(9) |
| C2 | 0.6012(6) | 0.4126(5) | 0.7257(4) | 1.91(9) |
| C3 | 0.4925(7) | 0.5653(5) | 0.6172(4) | 1.88(9) |
| C4 | 0.2900(6) | 0.5252(5) | 0.5922(4) | 1.52(9) |
| C5 | 0.0614(6) | 0.4174(5) | 0.6537(4) | 1.77(9) |

TABLE 6-continued

| atom | x | y | z | B$_{eq}$ |
|---|---|---|---|---|
| C6 | 0.3224(7) | 0.6047(6) | 1.0077(4) | 2.6(1) |
| C7 | 0.0065(7) | 0.6004(5) | 0.8514(4) | 1.86(9) | wherein, Beq indicates equivalent isotropic atomic displacement factor.

$Beq=8/3\pi^2$ $(U_{11}(aa^*)^2+U_{22}(bb^*)^2+U_{33}(cc^*)^2+2U_{12}(aebb^*)\cos\gamma+2U_{13}(aa^*cc^*)\cos\beta+2U_{23}(b\,b^*cc^*)\cos\alpha)$

TABLE 7

| atom | x | y | z | B$_{iso}$ |
|---|---|---|---|---|
| H1 | 0.2029 | 0.5910 | 0.5775 | 1.82 |
| H2 | 0.2596 | 0.4768 | 0.5327 | 1.82 |
| H3 | 0.5106 | 0.6065 | 0.5602 | 2.26 |
| H4 | 0.5200 | 0.6181 | 0.6738 | 2.26 |
| H5 | 0.6280 | 0.4646 | 0.7828 | 2.29 |
| H6 | 0.6949 | 0.3502 | 0.7431 | 2.29 |
| H7 | 0.3782 | 0.3099 | 0.6501 | 1.89 |
| H8 | 0.3909 | 0.3260 | 0.7638 | 1.89 |
| H9 | 0.2834 | 0.5081 | 0.7304 | 1.37 |
| H10 | 0.0496 | 0.3712 | 0.7087 | 2.12 |
| H11 | 0.0297 | 0.3716 | 0.5935 | 2.12 |
| H12 | −0.0262 | 0.4817 | 0.6438 | 2.12 |
| H13 | −0.0613 | 0.6213 | 0.7831 | 2.23 |
| H14 | −0.0653 | 0.6271 | 0.8948 | 2.23 |
| H15 | 0.0195 | 0.5181 | 0.8565 | 2.23 |
| H16 | 0.3162 | 0.5221 | 1.0033 | 3.11 |
| H17 | 0.2441 | 0.6313 | 1.0478 | 3.11 |
| H18 | 0.4547 | 0.6282 | 1.0383 | 3.11 | wherein, Biso indicates isotropic atomic displacement factor.

Moreover, the structure in asymmetric unit was shown in FIG. 2.

As is apparent from the coordinate shown in FIG. 2, Table 6 and Table 7, the asymmetric unit was found to be consisted with the ratio of N-methylmorpholine, hydroiodic acid and dimethylsulfoxide being 1:1:1.

In addition, proton donating/accepting between N-methylmorpholine and hydroiodic acid was found, and it was confirmed that the salt of N-methylmorpholine and hydroiodic acid was formed.

Meanwhile, the number of non-hydrogen atom and hydrogen atom in Table 6 and Table 7 corresponds to that of FIG. 2, successively.

The results of the powder X-ray diffraction were shown in FIG. 3 and Table 8 (XRPD Method B).

TABLE 8

| 2θ |
|---|
| 12.613 |
| 16.929 |
| 17.506 |
| 19.539 |
| 20.780 |
| 25.814 |
| 26.335 |
| 26.970 |
| 28.393 |
| 28.905 |

Diffraction angles of major peaks (2θ): 12.6°±0.2°, 16.9°±0.2°, 17.5°±0.2°, 26.3°±0.2°, 28.9°±0.2°.

DSC measurement was shown in FIG. 4. The observed onset temperature was 125° C.

TG/DTA measurement was shown in FIG. 7. The observed onset temperature was 115° C. The weight loss of about 27% was observed on TG.

Example 5

Synthesis of Compound 6

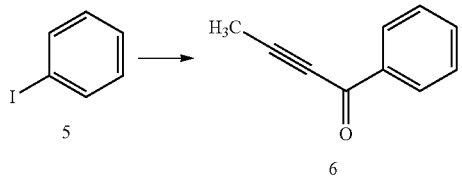

To iodobenzene (5)(2.04 g), Pd$_2$(dba)$_3$ (69.8 mg, 0.0075 equivalent), Xantphos (174.0 g, 0.03 equivalent), CuCl (60.5 mg, 0.06 equivalent), Compound (4)(154.2 mg) obtained in the Example 4 and N,N-dimethylglycine (40.0 mg, 0.04 equivalent) were added tetrahydrofuran (2 mL), N-methylmorpholine (4.06 g, 4 equivalents) and dimethylsulfoxide (1 mL), successively under nitrogen atmosphere. The slurry was stirred at about 25° C. under carbon monoxide atmosphere, and about 0.64 mol/L of the solution in which propyne gas (2.3 equivalents) was preliminarily dissolved in tetrahydrofuran was added to the slurry over about 0.5 hours and the resulting slurry was stirred for about 22 hours. After completion of the reaction, the atmosphere in the vessel was replaced with nitrogen gas and the precipitated solids were collected by filtration and the filtrate was concentrated. The residue was purified by silicagel column chromatography (hexane:ethylacetate=80:20 and 95:5) to give 1.13 g of Compound 6 as yellow oil, yield 78%.

$^1$H-NMR (CDCl$_3$) δ: 8.14 (2H, d, J=6 Hz), 7.60 (1H, t, J=6 Hz), 7.48 (2H, t, J=6 Hz), 2.16 (3H, s)

$^{13}$C-NMR (CDCl$_3$) δ: 178.22, 136.85, 133.91, 129.58, 128.48, 92.46, 4.32

Example 6

Synthesis of 4-(3-chloro-4-(3-fluorobenzyloxy)phenylamino)-6-(1-((S)-morpholine-2-yl-methoxyimino)-2-butyn-1-yl)quinazoline•2HCl (V'-1)

[Chemical Formula 37]

(II″) ⟶

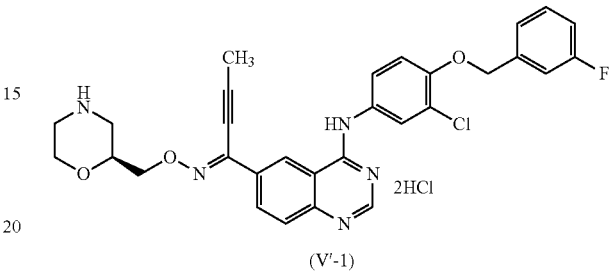

The compound represented by Formula (II″) was prepared according to the above Example 2.

(2) Synthesis of 4-(3-chloro-4-(3-fluorobenzyloxy)phenylamino)-6-(1-((S)-morpholine-2-yl-methoxyimino)-2-butyn-1-yl)quinazoline•2HCl To a suspension of 4-(3-chloro-4-(3-fluorobenzyloxy)phenylamino)-6-(1-oxo-2-butyn-1-yl)quinazoline (II″) (786 mg) and tert-butyl (S)-2-aminoxymethyl-morpholine-4-carboxylate (614 mg) in 1,4-dioxane (31 mL) was added 2 mol/L methanesulfonic acid aq. solution (2.21 mL) and stirred for 22 hr at 80° C. 2 mol/L methanesulfonic acid aq. solution (1.32 mL) was added and stirred for additional 5.5 hr. After the reaction was completed, the mixture was poured into ice-sodium hydrogen carbonate aq. solution and extracted with ethyl acetate. After the aqueous layer was extracted again with ethylacetate, all the organic layers were combined, washed with water and dried over anhydrous magnesium sulfate. The filtrate was concentrated and the residue was purified by silicagel column chromatography (eluted with chloroform:methanol=9:1) to give yellow oil. A solution of this oil in ethyl acetate (50 mL) was filtered and 4 mol/L hydrochloric acid-ethyl acetate (0.95 mL) was added under stirring and stirred for 1 hr at room temperature. The precipitate was filtered and washed with ethyl acetate and then hexane. The precipitate was recrystallized from methanol-ethyl acetate to give 4-(3-chloro-4-(3-fluorobenzyloxy)phenylamino)-6-(1-((S)-morpholine-2-yl-methoxyimino)-2-butyn-1-yl)quinazoline•2HCl (V'-1) (839 mg) as yellow crystalline form.

$^1$H-NMR (d$_6$-DMSO, δ): 11.69 (1H, bs), 9.49-9.37 (2H, m), 9.05 (1H, s), 8.88 (1H, s), 8.38 (1H, dd, J=1.5 Hz, J=8.7 Hz), 7.96 (1H, d, J=8.7 Hz), 7.89 (1H, d, J=2.7 Hz), 7.64 (1H, dd, J=2.4 Hz, J=9.0 Hz), 7.52-7.45 (1H, m), 7.36-7.30 (3H, m), 7.23-7.16 (1H, m), 5.31 (2H, s), 4.36-4.34 (1H, m), 4.25-4.22 (1H, m), 4.04-3.98 (1H, m), 3.84-3.77 (1H, m), 3.04-2.85 (3H, m), 2.28 (3H, s).

Example 7

Synthesis of 4-(3-chloro-4-(3-fluorobenzyloxy)phenylamino)-6-(1-(2-ethylaminoethoxyimino)-2-butyn-1-yl)quinazoline (V'-2)

[Chemical Formula 38]

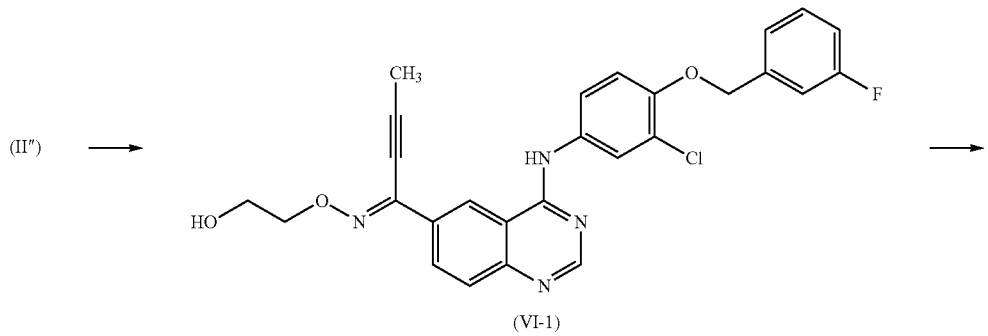

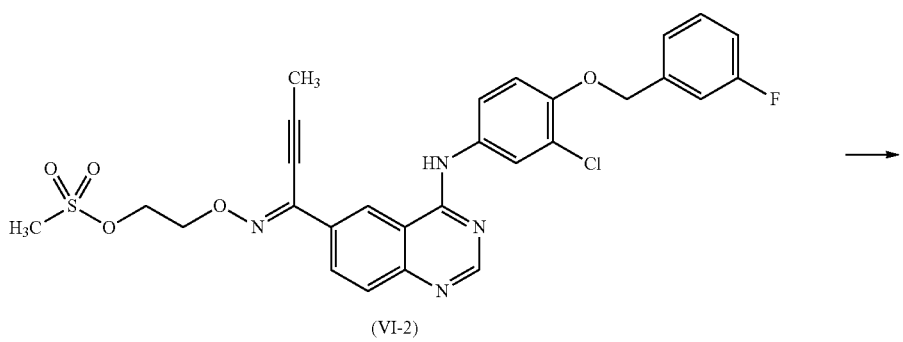

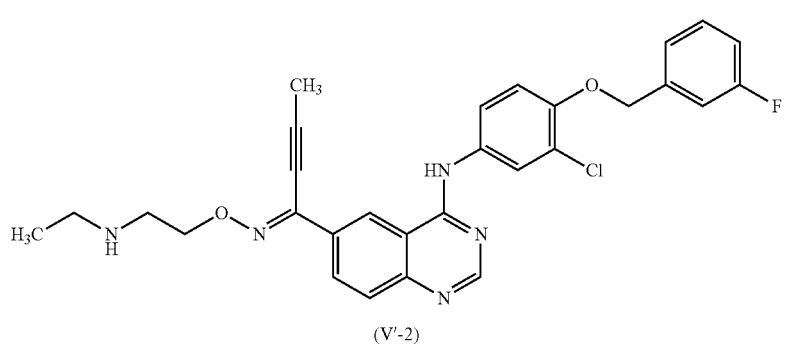

The compound represented by Formula (II″) was prepared according to the above Example 2.

(2) Synthesis of 4-(3-chloro-4-(3-fluorobenzyloxy)phenylamino)-6-(1-(2-hydroxyethoxyimino)-2-butyn-1-yl)quinazoline (VI-1)

To a solution of 4-(3-chloro-4-(3-fluorobenzyloxy)phenylamino)-6-(1-oxo-2-butyn-1-yl)quinazoline (II″)(10 g) in 1,4-dioxane (300 mL) was added 2-(acetoxy)ethoxyamine (1.5 equiv) and then 2 mol/L methane sulfonic acid aq.

solution (28 mL) and stirred for 17 hr at 60° C. The reaction mixture was poured into saturated sodium hydrogen carbonate aq. solution and extracted with ethyl acetate. The organic layer was washed with water and dried over sodium sulfate. The filtrate was concentrated and the residue was recrystallized from hydrous ethanol-water, filtered and dried to give 4-(3-chloro-4-(3-fluorobenzyloxy)phenylamino)-6-(1-(2-hydroxyethoxyimino)-2-butyn-1-yl)quinazoline (VI-1) (7.6 g) as a colorless solid.

$1^H$ NMR ($d_6$-DMSO, δ): 10.07 (1H, s), 8.74 (1H, s), 8.58 (1H, s), 8.22 (1H, d, J=8.8 Hz), 7.96 (1H, d, J=2.4 Hz), 7.80 (1H, d, J=8.8 Hz), 7.69 (1H, dd, J=2.4 Hz, J=8.8 Hz), 7.50-7.45 (1H, m), 7.35-7.24 (3H, m), 7.20-7.16 (1H, m), 5.27 (2H, s), 4.79 (1H, t, J=5.6 Hz), 4.29 (2H, t, J=5.6 Hz), 3.75 (2H, dd, J=5.2 Hz, J=10.4 Hz), 2.26 (3H, s).

(3) Synthesis of 4-(3-chloro-4-(3-fluorobenzyloxy)phenylamino)-6-(1-(2-sulfonyloxyethoxyimino)-2-butyn-1-yl) quinazoline (VI-2)

To a solution of 4-(3-chloro-4-(3-fluorobenzyloxy)phenylamino)-6-(1-(2-hydroxyethoxyimino)-2-butyn-1-yl)quinazoline (VI-1) (7.6 g) in tetrahydrofuran (150 mL) was added triethylamine (4.19 mL) and methanesulfonyl chloride (2.33 mL) and stirred for 3.5 hr. After the reaction was completed, the reaction mixture was poured into water and sodium hydrogen carbonate aq. solution was added to it. The mixture was extracted with ethyl acetate and the organic layer was dried over sodium sulfate and the filtrate was concentrated. Ethyl acetate was added to the residue and stood still at room temperature to give crystalline form, and then diluted with hexane. The formed crystalline form was filtered to give 4-(3-chloro-4-(3-fluorobenzyloxy)phenylamino)-6-(1-(2-sulfonyloxyethoxyimino)-2-butyn-1-yl)quinazoline (VI-2) (7.66 g) as pale yellow crystalline form.

$1^H$ NMR ($d_6$-DMSO, δ): 10.07 (1H, s), 8.77 (1H, s), 8.60 (1H, s), 8.24 (1H, d, J=8.8 Hz), 7.97 (1H, d, J=2.4 Hz), 7.81 (1H, d, J=8.8 Hz), 7.69 (1H, dd, J=2.4 Hz, J=8.8 Hz), 7.51-7.45 (1H, m), 7.35-7.27 (3H, m), 7.21-7.17 (1H, m), 5.27 (2H, s), 4.58 (2H, t, J=4.8 Hz), 4.54 (2H, t, J=4.8 Hz), 3.24 (3H, s), 2.27 (3H, s).

(4) Synthesis of 4-(3-chloro-4-(3-fluorobenzyloxy)phenylamino)-6-(1-(2-ethylaminoethoxyimino)-2-butyn-1-yl)quinazoline (V'-1)

To a solution of 4-(3-chloro-4-(3-fluorobenzyloxy)phenylamino)-6-(1-(2-sulfonyloxyethoxyimino)-2-butyn-1-yl)quinazoline (VI-2) (100 mg) in N,N-dimethylformamide (3 mL) was added 70% ethylamine aq. solution (160 μl) and stirred for 14 hr at 60° C. Water was added to the reaction mixture and extracted with ethyl acetate. The organic layer was dried over magnesium sulfate, the filtrate was concentrated and the residue was purified by an amino column chromatography (eluting with ethyl acetate) to give 4-(3-chloro-4-(3-fluorobenzyloxy)phenylamino)-6-(1-(2-ethylaminoethoxyimino)-2-butyn-1-yl)quinazoline (V'-2) (53 mg) as a colorless solid.

$1^H$ NMR ($d_6$-DMSO, δ): 10.08 (1H, s), 8.74 (1H, s), 8.59 (1H, s), 8.21 (1H, d, J=8.4 Hz), 7.96 (1H, s), 7.80 (1H, d, J=8.8 Hz), 7.69 (1H, d, J=8.0 Hz), 7.51-7.45 (1H, m), 7.35-7.27 (3H, m), 7.21-7.16 (1H, m), 5.27 (2H, s), 4.31 (2H, t, J=5.6 Hz), 2.89 (2H, t, J=6.0 Hz), 2.61 (2H, q, J=7.2 Hz), 2.26 (3H, s), 1.02 (3H, t, J=7.6 Hz).

For above amination, commercially available amines, or amines or a salt thereof prepared according to the methods described in J. Syn. Org. Chem., Jpn., 2001, 59: 779-789, Tetrahedron Lett., 1995, 36: 6373-6374, Synlett, 1999: 1301-1303, or Tetrahedron, 2002, 58: 6267-6276 can be used.

Example 8

[Chemical Formula 39]

(II″) ⟶

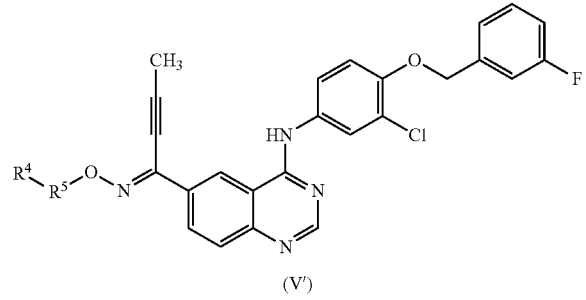

(V′)

Compound (V'-3)-(V'-17) were prepared according to the same manner as those of the above Examples 6 or 7.

[Chemical Formula 40]

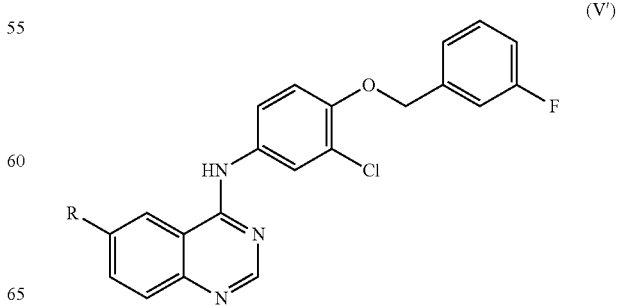

(V′)

TABLE 9

| Compound No. | R | ¹H-NMR(d₆-DMSO) |
|---|---|---|
| (V'-3) | HO-CH₂-CH(CH₃)-CH₂-NH-CH₂-CH₂-O-N=C(CH₃)-C≡C-CH₃ (structure with (S)-2-methyl-3-hydroxypropylamino group) | 10.08(1H, s), 8.75(1H, s), 8.68(1H; s), 8.22(1H, d, J = 8.8 Hz), 7.79(1H, s), 7.80(1H, d, J = 7.2 Hz), 7.70 (1H, d, J = 8.8 Hz), 7.50-7.45(1H, m), 7.35-7.27(3H, m), 7.18(1H, t, J = 8.8 Hz), 5.27(2H, s), 4.34(2H, t, J = 5.6 Hz), 3.35-3.32(2H, m), 2.92(2H, t, J = 5.6 Hz), 2.65-2.61(1H, m), 2.26(3H, s), 1.75-1.70(1H, bs), 0.84(3H, d, J = 5.6 Hz). |
| (V'-4) | H₃C-O-CH₂-CH₂-N(CH₃)-CH₂-CH₂-O-N=C(CH₃)-C≡C-CH₃ | 10.09(1H, s), 8.58(1H, s), 8.22(1H, dd, J = 8.7 Hz, 1.8 Hz), 7.95(1H, d, J = 2.7 Hz), 7.80(1H, d, J = 9.0 Hz), 7.68(1H, dd, J = 8.7 Hz, 2.7 Hz), 7.51-7.44 (1H, m), 7.35-7.16(4H, m), 3.22(3H, s), 2.77(2H, t, J = 5.7 Hz), 2.60(2H, t, J = 5.7 Hz), 2.29(3H, s), 2.24(3H, s). |
| (V'-5) | H₃C-O-CH₂-CH₂-N(CH₂CH₃)-CH₂-CH₂-O-N=C(CH₃)-C≡C-CH₃ | 10.09(1H, bs), 8.74(1H, s), 8.58(1H, s), 7.96(1H, d, J = 2.1 Hz), 7.80(1H, d, J = 8.7 Hz), 7.68(1H, d, J = 9.0 Hz), 7.48(1H, dd, J = 8.1 Hz), 7.35-7.26(3H, m), 7.19(1H, t, J = 8.1 Hz), 5.27(2H, s), 4.32(2H, t, J = 6.0 Hz), 3.23(3H, s), 2.85(2H, t, J = 6.0 Hz), 2.87-2.59 (4H, m), 2.24(3H, s), 0.98(3H, t, J = 7.2 Hz). |
| (V'-6) | HO-CH₂-CH₂-N(CH₃)-CH₂-CH₂-O-N=C(CH₃)-C≡C-CH₃ | (2 HCl salt) 10.70(1H, brs), 9.92(1H, brs), 8.94(1H, s), 8.69(1H, s), 8.30(1H, d, J = 12), 7.95-7.94(1H, m), 786(1H, d, J = 12), 7.71-7.68(1H, m), 7.52-7.44(1H, m), 7.35-7.28(3H, m), 7.22-7.15(1H, m), 5.40(1H, br), 5.30(2H, s), 4.74-4.60(2H, m), 3.83-3.75(2H, m), 3.70-3.55(2H, m), 2.92(3H, s), 2.28(3H, s) |
| (V'-7) | H₃C-NH-CH₂-CH₂-CH₂-O-N=C(CH₃)-C≡C-CH₃ | 10.09(1H, s), 8,75(1H, s), 8,59(1H, s), 8,22(1H, d, J = 8.7 Hz), 7.95(1H, d, J = 2.1 Hz), 7.81 (1H, d, J = 9.0 Hz), 7.69(1H, d, J = 8.7 Hz), 7.51-7.34(1H, m), 7.34-7.26(2H, m), 7.21-7.16(1H, m), 5.27(2H, s), 4.34(2H, t, J = 6.3 Hz), 2.96(2H, t,, J = 6.9 Hz), 2.56(3H, s), 2.26(3H, s). |

TABLE 10

| Compound No. | R | ¹H-NMR(d₆-DMSO) |
|---|---|---|
| (V'-8) | pyrrolidin-2-yl-methyl-O-N=C(CH₃)-C≡C-CH₃ | 10.08(1H, bs), 8.74(1H, s), 8.56(1H, s), 8.21(1H, d, J = 8.0 Hz), 7.93(1H, s), 7.79(1H, d, J = 8.8 Hz), 7.67-7.65(1H, m), 7.50-7.40(1H, m), 7.33-7.24(2H, m), 7.20-7.12(1H, m), 5.25(2H, s), 4.36-4.30(1H, m), 4.22-4.17(1H, m), 4.08-3.92(2H, m), 2.98(2H, bs), 2.24(3H, s), 2.00-1.90(1H, m), 1.80-1.70(2H, m), 1.62-1.52(1H, m) |

TABLE 10-continued

| Compound No. | R | $^1$H-NMR($d_6$-DMSO) |
|---|---|---|
| (V'-9) | [pyrrolidine with 4-hydroxy, CH₂-O-N=C(CH₃)-C≡C- substituent] | 10.45(1H, s), 8.92(1H, s), 8.65(1H, s), 8.31(1H, d, J = 8.4 Hz), 7.97(1H, s), 7.77(1H, d, J = 8.8 Hz), 7.71(1H, d, J = 9.2 Hz), 7.51-7.45(1H, m), 7.35-7.28(2H, m), 7.19(1H, t, J = 8.4 Hz), 5.28(2H, s), 4.56-4.47(3H, m), 4.15(1H, bs), 3.60(1H, bs), 3.12(1H, bs), 2.28(3H, s), 2.09(1H, dd, J = 13.2 Hz, J = 6.0 Hz), 1.862-1.81(1H, m). |
| (V'-10) | [pyrrolidine with 4-hydroxy, CH₂-O-N=C(CH₃)-C≡C- substituent] | 10.08(1H, s), 8.75(1H, s), 8.59(1H, s), 8.22(1H, d, J = 8.8 Hz), 7.97(1H, s), 7.80(1H, d, J = 8.8 Hz), 7.69(1H, d, J = 8.0 Hz), 7.51-7.45(1H, m), 7.35-7.27(m, 3H), 7.20-7.17(1H, m), 5.27(2H, s), 4.67(1H, bs), 4.29-4.19(3H, m), 3.45-4.40(1H, m), 2.88(1H, dd, J = 11.2 Hz, J = 5.6 Hz), 2.70(1H, dd, J = 11.0, J = 3.6 Hz), 2.27(3H, s), 2.10-2.02(1H, m), 1.46-1.39(1H, m). |
| (V'-11) | [morpholine with CH₂-O-N=C(CH₃)-C≡C- substituent] | 10.09(1H, bs), 8.75(1H, s), 8.58(1H, s), 8.20(1H, d, J = 8.7 Hz), 7.95(1H, d, J = 2.1 Hz), 7.80(1H, d, J = 8.7 Hz), 7.68(1H, d, J = 9.0 Hz), 7.51-7.44(1H, m), 7.35-7.26(3H, m), 7.21-7.16(1H, m), 5.27(2H, s), 4.20-4.09(2H, m), 3.79(1H, dd, J = 2.7 Hz, J = 10.8 Hz), 3.68-3.64(1H, m), 3.13-3.08(1H, m), 2.82-2.71(3H, m), 2.26(3H, s). |
| (V'-12) | [morpholine with CH₂-O-N=C(CH₃)-C≡C- substituent] | 10.11(1H, bs), 8.74(1H, s), 8.57(1H, s), 8.22-8.19(1H, m), 7.96(1H, m), 7.80(1H, d, J = 9.0 Hz), 7.69-7.66(1H, m), 7.51-7.44(1H, m), 7.35-7.26(3H, m), 7.21-7.16(1H, m), 5.27(2H, s), 4.20-4.09(2H, m), 3.79(1H, dd, J = 3.0 Hz, J = 10.8 Hz), 3.68-3.64(1H, m), 3.25-3.18(1H, m), 3.13-3.05(1H, m), 2.82-2.71(2H, m), 2.26(3H, s). |
| (V'-13) | [piperazine with CH₂-O-N=C(CH₃)-C≡C- substituent] | 10.09(1H, brs), 8.74(1H, s), 8.59(1H, s), 8.21(1H, d, 9.0 Hz), 7.96(1H, s), 7.79(1H, d, J = 9.0 Hz) 7.68(1H, d, J = 9.0 Hz), 7.49-7.44(1H, m), 7.34-7.22(3H, m), 7.19-7.15(1H, m), 5.27(2H, s), 4.11(2H, d, J = 4.8 Hz), 2.95-2.50(6H, m), 2.34-2.26(4H, m) |

TABLE 11

| Compound No. | R | $^1$H-NMR($d_6$-DMSO) |
|---|---|---|
| (V'-14) | [morpholine-N-CH₂CH₂-O-N=C(CH₃)-C≡C- substituent] | (E/Z mixture) 10.09(1H, s, major), 10.00(1H, s, minor), 8.74(1H, s, major), 8.59(1H, s), 8.22(1H, d, J = 9 Hz, major), 7.94-8.02(1H, m), 7.64-7.82(2H, m), 7.44-7.52(1H, m), 7.16-7.36(4H, m), 5.27(2H, s), 4.32-4.43(2H, m), 3.56-3.62(4H, m), 2.66-2.74(2H, m), 2.34(3H, s, minor), 2.25(3H, s, major) |

TABLE 11-continued

| Compound No. | R | $^1$H-NMR($d_6$-DMSO) |
|---|---|---|
| (V'-15) | 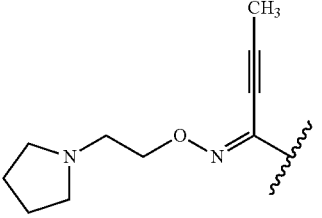 [SMILES: */C(C#CC)=N/OCCN1CCCC1] | 10.08(1H, s), 8.74(1H, s), 8.58(1H, s), 8.22(1H, d, J = 8.4 Hz), 7.96(1H, brs), 7.80(1H, d, J = 8.4 Hz), 7.68(1H, d, J = 9.6 Hz), 7.43-7.52(1H, m), 7.14-7.36(4H, m), 5.27(2H, s), 4.37(2H, t, J = 6.0 Hz), 2.80(2H, t, J = 6.0 Hz), 2.25(3H, s), 1.69(4H, brs), 1.24(4H, brs) |
| (V'-16) | 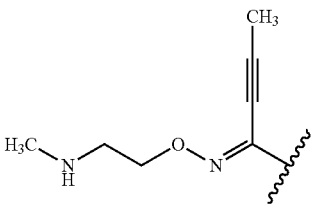 [SMILES: */C(C#CC)=N/OCCNC] | 10.10(1H, s), 8.76(1H, s), 8.60(1H, s), 8.25(1H, d, J = 8.7 Hz), 7.96(1H, brs), 7.82(1H, d, J = 9.0 Hz), 7.69(1H, d, J = 9.0 Hz), 7.43-7.52(1H, m), 7.14-7.36(4H, m), 5.28(2H, s), 4.43(2H, brs), 2.98(2H, brs), 2.54(3H, s), 2.27(3H, brs), 1.60(1H, s) |
| (V'-17) | 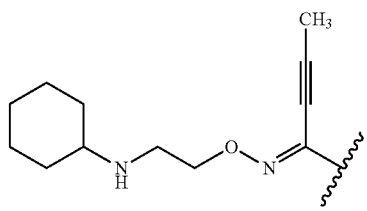 [SMILES: */C(C#CC)=N/OCCNC1CCCCC1] | 10.10(1H, s), 8.77(1H, s), 8.60(1H, s), 8.25(1H, d, J = 8.7 Hz), 7.95(1H, brs), 7.82(1H, d, J = 9.6 Hz), 7.69(1H, d, J = 9.3 Hz), 7.43-7.52(1H, m), 7.14-7.36(4H, m), 5.28(2H, s), 4.45(2H, brs), 2.91(2H, brs), 2.27(3H, s), 2.00(2H, brs), 1.73(2H, brs), 1.60(1H, brs), 1.23(7H, brs) |

Example 9

Synthesis of Compound 8

[Chemical Formula 41]

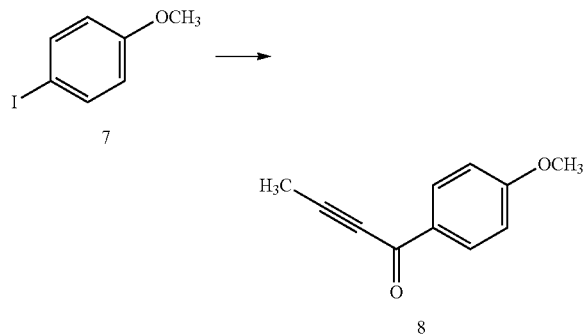

To 4-iodoanisle (7)(2.36 g), Pd$_2$(dba)$_3$ (69.9 mg, 0.0075 equivalent), Xantphos (173.0 mg, 0.03 equivalent), CuCl (61.2 mg, 0.06 equivalent), Compound (4)(152.0 mg) obtained in Example 4, and N,N-dimethylglycine (42.3 mg, 0.04 equivalent) were added tetrahydrofuran (2.3 mL), N-methylmorpholine (4.05 g, 4 equivalents) and dimethylsulfoxide (1.2 mL) successively under nitrogen atmosphere. The slurry was stirred at about 25° C. under carbon monoxide atmosphere, and about 0.50 mol/L of the solution in which propyne gas (2.3 equivalents) was preliminarily dissolved in tetrahydrofuran was added to the slurry over about 2 hours and the resulting slurry was stirred for about 2 hours at the same temperature. Then the slurry was warmed up to about 40° C. and stirred for additional 5 hours. After completion of the reaction, the atmosphere in the vessel was replaced with nitrogen gas and the precipitated solids were collected by filtration and the filtrate was concentrated. The residue was purified by silicagel column chromatography (hexane:ethylacetate=80:20 and 90:10) to give 1.22 g of Compound 8 as colorless solids, isolated yield 70%.

$^1$H-NMR (CDCl$_3$) δ: 8.11 (2H, d, J=8.9 Hz), 6.94 (2H, d, J=8.9 Hz), 3.88 (3H, s), 2.14 (3H, s)

$^{13}$C-NMR (CDCl$_3$) δ: 176.91, 164.33, 131.94, 130.28, 113.73, 91.49, 79.00, 55.55, 4.27

Example 10

Synthesis of Compound 10

[Chemical Formula 42]

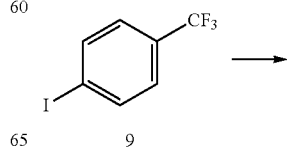

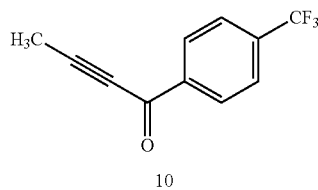

To 4-iodobenzotrifluoride (9)(2.73 g), $Pd_2(dba)_3$ (71.7 mg, 0.0075 equivalent), Xantphos (175.0 mg, 0.03 equivalent), CuCl (59.5 mg, 0.06 equivalent), Compound (4)(152.0 mg) obtained in Example 4, and N,N-dimethylglycine (43.1 mg, 0.04 equivalent) were added tetrahydrofuran (2.7 mL), N-methylmorpholine (4.05 g, 4 equivalents) and dimethylsulfoxide (1.4 mL) successively under nitrogen atmosphere. The slurry was stirred at about 25° C. under carbon monoxide atmosphere, and about 0.50 mol/L of the solution in which propyne gas (2.3 equivalents) was preliminarily dissolved in tetrahydrofuran was added to the slurry over about 2 hours and the resulting slurry was stirred for about 2 hours at the same temperature. Then the slurry was warmed up to about 40° C. and stirred for additional 5 hours. After completion of the reaction, the atmosphere in the vessel was replaced with nitrogen gas and the precipitated solids were collected by filtration and the filtrate was concentrated. The residue was purified by silicagel column chromatography (hexane:ethylacetate=80:20 and 90:10) to give 1.30 g of Compound 10 as brown solids, isolated yield 61%.

$^1$H-NMR (CDCl$_3$) δ: 8.25 (2H, d, J=8.1 Hz), 7.75 (2H, d, J=8.1 Hz), 2.20 (3H, s)

$^{13}$C-NMR (CDCl$_3$) δ: 176.85, 139.32, 135.54, 135.22, 134.89, 134.57, 129.80, 127.62, 125.62, 125.58, 125.54, 125.51, 124.91, 122.20, 119.48, 93.95, 78.76, 4.35

Example 11

Synthesis of Compound 12

[Chemical Formula 43]

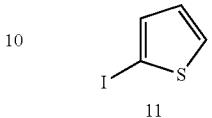 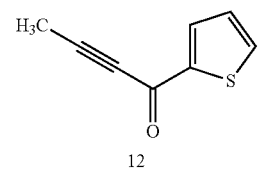

To 2-iodothiophene (11)(2.10 g), $Pd_2(dba)_3$ (138.0 mg, 0.015 equivalent), Xantphos (347.0 mg, 0.06 equivalent), CuCl (120.0 mg, 0.12 equivalent), Compound (4)(155.0 mg) obtained in Example 4, and N,N-dimethylglycine (83.5 mg, 0.08 equivalent) were added tetrahydrofuran (2.1 mL), N-methylmorpholine (4.05 g, 4 equivalents) and dimethylsulfoxide (1.1 mL) successively under nitrogen atmosphere. The slurry was stirred at about 25° C. under carbon monoxide atmosphere, and about 0.98 mol/L of the solution in which propyne gas (2.3 equivalents) was preliminarily dissolved in tetrahydrofuran was added to the slurry over about 1 hour and the resulting slurry was stirred for about 3 hours at the same temperature. Then the slurry was warmed up to about 40° C. and stirred for additional three and a half hours. After completion of the reaction, the atmosphere in the vessel was replaced with nitrogen gas and the precipitated solids were collected by filtration and the filtrate was concentrated. The residue was purified by silicagel column chromatography (n-hexane:ethylacetate=90:10) to give 1.31 g of Compound 12 as yellow oil, isolated yield 87%.

$^1$H-NMR (CDCl$_3$) δ: 7.90 (1H, dd, J=3.8, 1.2 Hz), 7.68 (1H, dd, J=4.9, 1.2 Hz), 7.14 (1H, dd, 4.9, 1.2 Hz). 2.13 (3H, s)

$^{13}$C-NMR (CDCl$_3$) δ: 170.02, 144.93, 135.01, 134.88, 128.18, 90.98, 78.60, 4.22

Test Example 1 Reaction Heat Flow in Sonogashira-Carbonylation Reaction

[Chemical Formula 44]

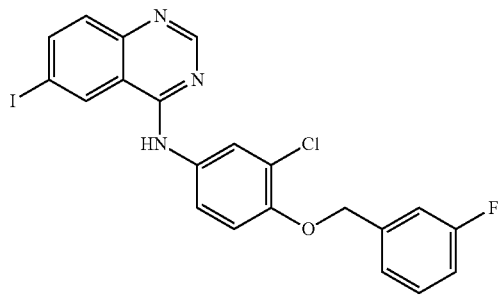

Pd$_2$(dba)$_3$ (0.75 mol %)
Xantphos (3 mol %), CuCl (6 mol %)
N,N-dimethylglycine (4 mol %)
NMM (4 eq.), CO (1.5 atm)
Propyne (2.35 eq.)
─────────────────
DMSO(0.5 V), THF(2.2 V), rt

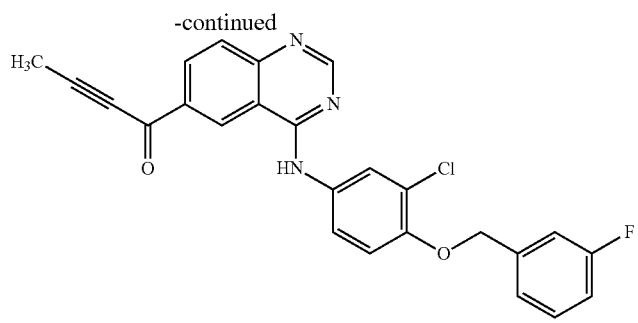

In the process described in the above scheme, the reaction heat flow of Sonogashira-carbonylation reaction in the absence of the crystalline form of the complex comprising N-methylmorpholine, hydroiodic acid and dimethylsulfoxide is described as FIG. 5.

In the process described in the above scheme, the reaction heat flow of Sonogashira-carbonylation reaction in the presence of the crystalline form of the complex comprising N-methylmorpholine, hydroiodic acid and dimethylsulfoxide is described as FIG. 6.

From FIG. 5, in the absence of the said crystalline form, it was found that the reaction heat flow was exponentially increased as the complex comprising N-methylmorpholine, hydroiodic acid and dimethylsulfoxide was generated as by-product. Also, it was found that the ratio (%) to total heat was not pursued propyne addition. Therefore, the large scale synthesis is dangerous because the heat flow is not able to be controlled.

In contrast, as is apparent from FIG. 6, in the reaction system in which small amount of the said crystalline form was added before the reaction was started; (in the presence of the said crystalline form), it was found that the phenomenon that the heat flow was exponentially increased was not observed. Also, it was found that the ratio (%) to total heat was nearly pursued propyne addition. Even in the large scale synthesis, the heat flow is able to be controlled, so that the industrial production can be carried out.

Therefore, the desired product is able to be obtained more safely in the presence of the said crystalline form by Sonogashira-carbonylation reaction of the present invention, and it may be said that the present invention is industrially excellent process.

Test Example 2 Solubility Test of Methanesulfonate of Compound Represented by Formula (II")

Crystalline form of methanesulfonate of Compound represented by Formula (II") and crystalline form of free form of Compound represented by Formula (II") were suspended in tetrahydrofuran or acetonitrile, respectively. The slurries were stirred at 20° C. to 25° C. for over two hours, and then the concentration in each supernatant solution was measured (HPLC method A). The HPLC results of the concentration in each supernatant solution are indicated as Table 12.

TABLE 12

| Solvent | Temperature (° C.) | MsOH salt of Formula (II") | Free form of Formula (II") |
|---|---|---|---|
| Tetrahydrofuran | 20 to 25 | 0.05% | 3.6% |
| Acetonitrile | 20 to 25 | 0.05% | 0.3% |

TABLE 12-continued

| Solvent | Temperature (° C.) | MsOH salt of Formula (II") | Free form of Formula (II") |
|---|---|---|---|
| Conditions in Example 2 (DMSO/ NMM/THF/MeCN) | 0 | 3.1% | 15.7% |

As indicated in Table 12, it was found that the solubility of the crystalline form of methanesulfonate of Compound represented by Formula (II") in each solvent was low compared to that of the crystalline form of free form of Compound represented by Formula (II"). Here, it means that the crystalline form that has low solubility is not easily dissolved into a solvent which is used to wash the crystalline form.

Moreover, the concentration of each crystalline form being dissolved into the solution at 0° C. in Step 1 (Step to obtain the crystalline form of methanesulfonate) and Step 2 (Step to obtain the crystalline form of free form) in Example 2 was measured by HPLC method A and compared (Table 12). It was found that only 3.1% of the crystalline form of methanesulfonate of Compound represented by (II") was dissolved into the solution, whereas 15.7% of the crystalline form of free form of Compound represented by (II") was dissolved into the solution.

Therefore, the crystalline form of methanesulfonate of Compound represented by Formula (II") is not easy dissolved into the solvent, because it has low solubility to the solvent, and it may be said that it is industrially excellent crystalline form, because the amount of loss becomes small in industrial process.

Test Example 3 Palladium Black Precipitate Inhibition Test

In Sonogashira-carbonylation reaction as shown in the following scheme, the result of yield of the desired product and the result of precipitate of palladium black are indicated in Table 13.

[Chemical Formula 45]

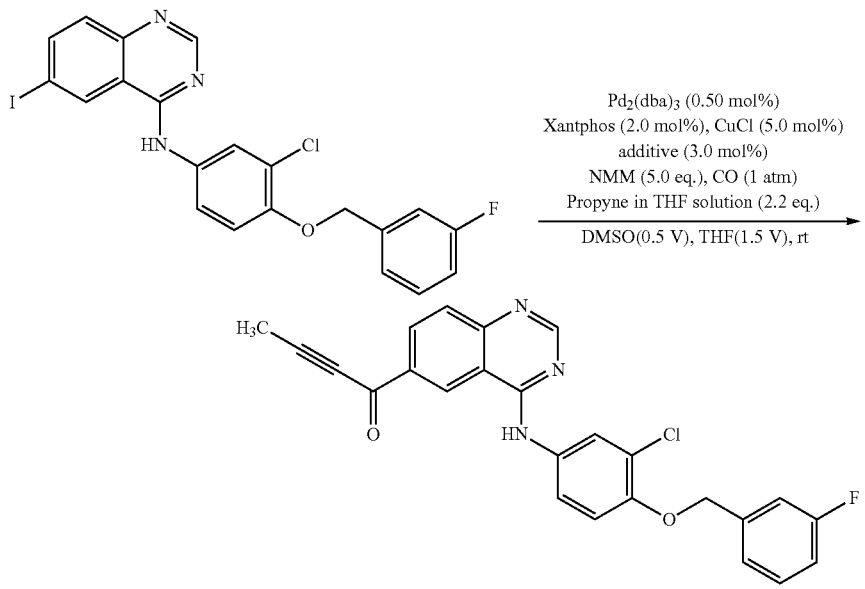

TABLE 13

| Additive | Yield of the desired product after 22 hours* | Precipitate of palladium black** | |
|---|---|---|---|
| | | After 8 hours | After 22 hours |
| None | 94% | – | +++ |
| N,N-Dimethylglycine | 93% | – | – |
| Picolinic acid | 91% | – | – |
| L-Proline | 93% | – | ++ |
| 2-Hydroxy-N,N-diethyl-benzamide | 95% | + | ++ |
| Ethylene glycol | 93% | – | – |
| Ethyl 2-oxocyclohexanecarboxylate | 93% | – | ++ |
| 2-Acetylcyclohexanone | 92% | – | ++ |
| 2-Hydroxybenzoic acid | 91% | – | ++ |
| 2-Furoic acid | 93% | – | ++ |
| Diethyl malonate | 92% | – | ++ |
| N,N-Dimethylethylenediamine | 94% | – | + |
| Acetic acid | 94% | – | ++ |
| Copper(I) 2-thiophenecarboxylate (Reference Example) | 88% | – | + |
| 1H-Pyrrole-2-carboxylic acid | 94% | + | +++ |
| N,N-Dimethylethanolamine | 94% | + | +++ |
| Dipivaloylmethane | 92% | + | +++ |

(*Area percentage of HPLC;
**Evaluated by visual judgment
"–" non-precipitate,
"+" minimal precipitate,
"++" thinly precipitated on the whole inner wall of flask,
"+++": thickly precipitated on the whole inner wall of flask;
Additives judged as "++" after 22 hours can be considered within practical use.

As indicated in Table 13, it was found that N,N-Dimethylglycine, Picolinic acid, L-Proline, 2-Hydroxy-N,N-diethyl-benzamide, Ethylene glycol, Ethyl 2-oxocyclohexanecarboxylate, 2-Acetylcyclohexanone, 2-Hydroxybenzoic acid, 2-Furoic acid, Diethyl malonate, N,N-Dimethylethylenediamine, Acetic acid and Copper(I) 2-thiophenecarboxylate can inhibit the precipitate of palladium black.

INDUSTRIAL APPLICABILITY

The present invention is useful as process for producing the compound having a dual inhibitory activity of both EGF receptor tyrosine kinase and HER2 tyrosine kinase, and the intermediate thereof.

The invention claimed is:

1. A process for producing a compound represented by Formula (II):

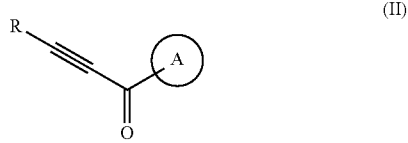

(II)

wherein ring A is a substituted or unsubstituted aromatic heterocycle or a substituted or unsubstituted aromatic carbocycle, R is a hydrogen atom or methyl, characterized by reacting a compound represented by Formula (I):

(I)

wherein ring A is as defined above, X is a leaving group, with carbon monoxide and a compound represented by Formula (III):

(III)

wherein R is as defined above, in the presence of a palladium catalyst, a phosphine ligand, a catalyst comprising Group 11 element and a base.

2. The process according to claim 1, wherein R is methyl.

3. The process according to claim 1, wherein the palladium catalyst is Pd$_2$ (dba)$_3$, PdCl$_2$ dppf, PdCl$_2$ (PPh$_3$)$_2$, Pd(OAc)$_2$, Pd(PPh$_3$)$_4$, Pd/C, PdCl$_2$, Pd-PEPPSI™-IPr, Bis[cinnamyl palladium Cl], PdCl$_2$ (Xantphos) or Pd(OH)$_2$.

4. The process according to claim 1, wherein the phosphine ligand is Xantphos, P(2-furyl)$_3$, PPh$_3$, P(o-tol)$_3$, P(OPh)$_3$, P(OMe)$_3$, dppp, dppb, dppf, BINAP, X-Phos, P(t-Bu)$_3$, P(Oi-Pr)$_3$, P(p-MeOPh)$_3$ or DPEPhos.

5. The process according to claim 1, wherein the catalyst comprising Group 11 element is copper iodide(I), copper iodide(II), copper chloride(I), copper chloride(II), copper acetate(I), copper acetate(II), copper oxide(II), copper bromide(I), copper bromide(II) or silver acetate.

6. The process according to claim 1, wherein the base is N-methylmorpholine, triethylamine, diisopropylethylamine, pyridine, DABCO, N,N-dimethylbenzylamine, N,N-dimethylaniline, sodium acetate, potassium carbonate, sodium carbonate or potassium phosphate.

7. The process according to claim 2, wherein the compound represented by Formula (II) is a compound represented by Formula (II'):

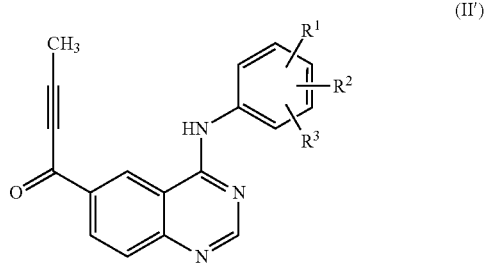

wherein R$^1$ is a hydrogen atom, halogen, substituted or unsubstituted alkyloxy, substituted or unsubstituted alkenyloxy, substituted or unsubstituted alkynyloxy or a group represented by formula: —Y—R$^y$, wherein —Y— is —O—, —S—, —SO$_2$—, or alkylene which may be intervened with —O—, —S— or —N(R$^z$)—; R$^y$ is substituted or unsubstituted aromatic carbocyclyl or substituted or unsubstituted aromatic heterocyclyl; and R$^z$ is a hydrogen atom, substituted or unsubstituted alkyl, substituted or unsubstituted acyl, substituted or unsubstituted alkyloxycarbonyl, substituted or unsubstituted alkenyloxycarbonyl or substituted or unsubstituted aromatic carbocyclyl alkyloxycarbonyl;

R$^2$ and R$^3$ are each independently a hydrogen atom, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, halogen, hydroxy, mercapto, cyano or substituted or unsubstituted amino.

8. The process according to claim 7, wherein R$^1$ is a group represented by formula: —Y—R$^y$, wherein —Y— is alkylene which may be intervened with —O—; and R$^y$ is phenyl unsubstituted or substituted with a substituent selected from a substituent group p [substituent group p: halogen, carboxy, alkyl, haloalkyl, hydroxyalkyl, alkyloxy, alkyloxycarbonyl and substituted or unsubstituted amino], pyridyl unsubstituted or substituted with a substituent selected from a substituent group p, furyl unsubstituted or substituted with a substituent selected from a substituent group p, thienyl unsubstituted or substituted with a substituent selected from a substituent group p, thiazolyl unsubstituted or substituted with a substituent selected from a substituent group p, or oxazolyl unsubstituted or substituted with a substituent selected from a substituent group p;

R$^2$ is substituted or unsubstituted alkynyl, substituted or unsubstituted alkyloxy or halogen; and R$^3$ is a hydrogen atom.

9. The process according to claim 7, wherein the compound represented by Formula (II') is a compound represented by Formula (II"):

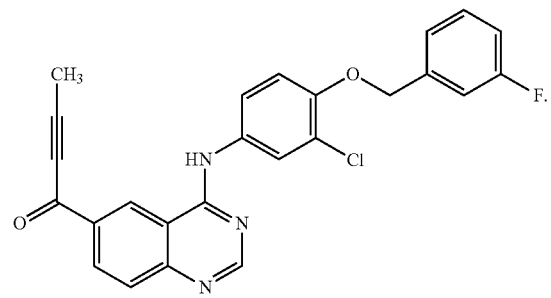

10. A crystalline form of methanesulfonate of the compound represented by Formula (II"):

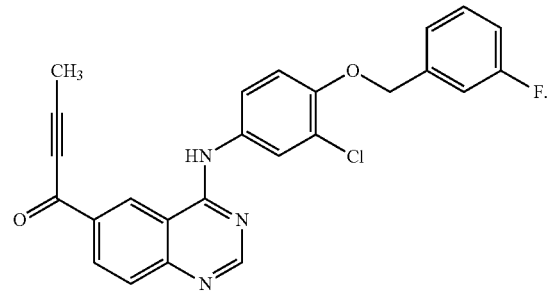

11. The crystalline form according to claim 10, wherein diffraction angle 2θ of the powder X-Ray diffraction analysis are 5.6°±0.2°, 9.8°±0.2°, 17.9°±0.2°, 24.4°±0.2°, and 26.4°±0.2°.

12. The crystalline form according to claim 10, wherein diffraction angle 2θ of the powder X-Ray diffraction analysis are 5.6°±0.2°, 8.3°±0.2°, 9.8°±0.2°, 13.7°±0.2°, 17.0°±0.2°, 17.9°±0.2°, 21.3°±0.2°, 24.4°±0.2°, 26.0°±0.2°, and 26.4°±0.2°.

13. A complex comprising N-methylmorpholine, hydroiodic acid and dimethylsulfoxide.

14. The complex according to claim 13, wherein the complex is a crystalline form.

15. The crystalline form of the complex according to claim 14, wherein said crystalline form of the complex is characterized by the following crystal data:

TABLE 1

| Space Group | P2$_1$/c |
|---|---|
| a (Å) | 7.3750(2) |
| b (Å) | 11.8395(3) |
| c (Å) | 14.2325(4) |
| α (°) | 90 |
| β (°) | 107.764(2) |
| γ (°) | 90 |
| V (Å$^3$) | 1183.47(5) |
| Z | 4 |
| Density(calculated value) (g/cm$^3$) | 1.724 |
| Measured temperature (° C.) | −173. |

16. The crystalline form of the complex according to claim 14, wherein diffraction angle 2θ of the powder X-Ray diffraction analysis are 12.6°±0.2°, 16.9°±0.2°, 17.5°±0.2°, 26.3°±0.2°, and 28.9°±0.2°.

17. The crystalline form of the complex according to claim 14, wherein diffraction angle 2θ of the powder X-Ray diffraction analysis are 12.6°±0.2°, 16.9°±0.2°, 17.5°±0.2°, 19.5°±0.2°, 20.8°±0.2°, 25.8°±0.2°, 26.3°±0.2°, 27.0°±0.2°, 28.4°±0.2°, and 28.9°±0.2°.

18. The process according to claim 1, wherein the compound represented by Formula (I) is a compound represented by Formula (I'):

(I')

wherein ring A is as defined in claim 1, and
the base is N-methylmorphiline,
characterized in that the process is carried out in the presence of the crystalline form of the complex comprising N-methylmorpholine, hydroiodic acid and dimethylsulfoxide.

19. The process according to claim 2, wherein the compound represented by Formula (I) is a compound represented by Formula (I"):

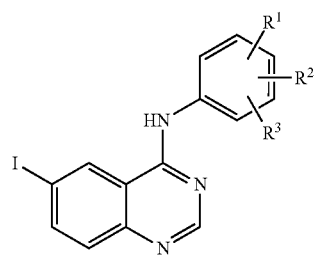

(I")

wherein R$^1$ is a hydrogen atom, halogen, substituted or unsubstituted alkyloxy, substituted or unsubstituted alkenyloxy, substituted or unsubstituted alkynyloxy or a group represented by formula: —Y—R$^y$, wherein —Y— is —O—, —S—, —SO$_2$—, or alkylene which may be intervened with —O—, —S— or —N(R$^z$)—; R$^y$ is substituted or unsubstituted aromatic carbocyclyl or substituted or unsubstituted aromatic heterocyclyl, and R$^z$ is a hydrogen atom, substituted or unsubstituted alkyl, substituted or unsubstituted acyl, substituted or unsubstituted alkyloxycarbonyl, substituted or unsubstituted alkenyloxycarbonyl or substituted or unsubstituted aromatic carbocyclyl alkyloxycarbonyl;

R$^2$ and R$^3$ are each independently a hydrogen atom, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, halogen, hydroxy, mercapto, cyano or substituted or unsubstituted amino, the base is N-methylmorphiline, and
the compound represented by Formula (II) is the compound represented by Formula (II'):

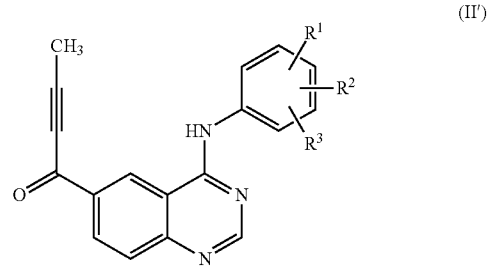

(II')

wherein R$^1$, R$^2$ and R$^3$ are as defined above,
characterized in that the process is carried out in the presence of the crystalline form of the complex comprising N-methylmorpholine, hydroiodic acid and dimethylsulfoxide.

20. The process according to claim 2, wherein the compound represented by Formula (I) is a compound represented by Formula (I'''):

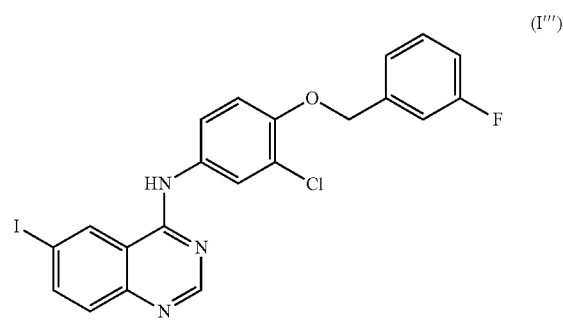 [SMILES: Fc1cccc(COc2ccc(Nc3ncnc4ccc(I)cc34)cc2Cl)c1]

(I''')

the base is N-methylmorphiline, and
the compound represented by Formula(II) is the compound represented by Formula(II"):

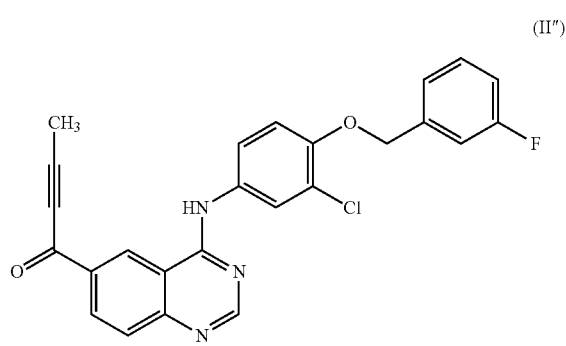 [SMILES: CC#CC(=O)c1ccc2ncnc(Nc3ccc(OCc4cccc(F)c4)c(Cl)c3)c2c1]

(II")

characterized in that the process is carried out in the presence of the crystalline form of the complex comprising N-methylmorpholine, hydroiodic acid and dimethylsulfoxide.

21. The process according to claim 1, characterized in that the process is carried out in the presence of N,N-dimethylglycine, picolinic acid, L-proline, 2-hydroxy-N,N-diethylbenzamide, ethylene glycol, ethyl 2-oxocyclohexanecarboxylate, 2-acetylcyclohexanone, 2-hydroxybenzoic acid, 2-furoic acid, diethyl malonate, N,N-dimethylethylenediamine, acetic acid, copper(I) 2-thiophenecarboxylate, glycine, N-methylglycine, D-proline, N-methylproline, imidazole-4-carboxylic acid, oxazole-4-carboxylic acid, thiazole-4-carboxylic acid, imidazole-2-carboxylic acid, oxazole-2-carboxylic acid, thiazole-2-carboxylic acid, pyrrole-2-carboxylic acid, isoxazole-5-carboxylic acid, isoxazole-3-carboxylic acid, alanine, valine, leucine, isoleucine, 2-dimethylaminobenzoic acid, glycolamide, formic acid, propionic acid, butyric acid, oxalic acid, maleic acid, trifluoroacetic acid, malonic ester, acetoacetic ester, ethylene glycol dimethyl ether, 2-methoxyethanol, glycolic acid, glycolic ester, 1,3-propanediol, 1,4-butanediol, 1,5-pentanediol, diethylene glycol, catechol, 2-hydroxymethyl-1,3-propanediol, N,N-dimethylurea, N,N-diphenylurea or N,N-dimethylglycinamide.

22. The process according to claim 7, characterized in that the process is carried out in the presence of N,N-dimethylglycine, picolinic acid, L-proline, 2-hydroxy-N,N-diethylbenzamide, ethylene glycol, ethyl 2-oxocyclohexanecarboxylate, 2-acetylcyclohexanone, 2-hydroxybenzoic acid, 2-furoic acid, diethyl malonate, N,N-dimethylethylenediamine, acetic acid, copper(I) 2-thiophenecarboxylate, glycine, N-methylglycine, D-proline, N-methylproline, imidazole-4-carboxylic acid, oxazole-4-carboxylic acid, thiazole-4-carboxylic acid, imidazole-2-carboxylic acid, oxazole-2-carboxylic acid, thiazole-2-carboxylic acid, pyrrole-2-carboxylic acid, isoxazole-5-carboxylic acid, isoxazole-3-carboxylic acid, alanine, valine, leucine, isoleucine, 2-dimethylaminobenzoic acid, glycolamide, formic acid, propionic acid, butyric acid, oxalic acid, maleic acid, trifluoroacetic acid, malonic ester, acetoacetic ester, ethylene glycol dimethyl ether, 2-methoxyethanol, glycolic acid, glycolic ester, 1,3-propanediol, 1,4-butanediol, 1,5-pentanediol, diethylene glycol, catechol, 2-hydroxymethyl-1,3-propanediol, N,N-dimethylurea, N,N-diphenylurea or N,N-dimethylglycinamide.

23. The process according to claim 9, characterized in that the process is carried out in the presence of N,N-dimethylglycine, picolinic acid, L-proline, 2-hydroxy-N,N-diethylbenzamide, ethylene glycol, ethyl 2-oxocyclohexanecarboxylate, 2-acetylcyclohexanone, 2-hydroxybenzoic acid, 2-furoic acid, diethyl malonate, N,N-dimethylethylenediamine, acetic acid, copper(I) 2-thiophenecarboxylate, glycine, N-methylglycine, D-proline, N-methylproline, imidazole-4-carboxylic acid, oxazole-4-carboxylic acid, thiazole-4-carboxylic acid, imidazole-2-carboxylic acid, oxazole-2-carboxylic acid, thiazole-2-carboxylic acid, pyrrole-2-carboxylic acid, isoxazole-5-carboxylic acid, isoxazole-3-carboxylic acid, alanine, valine, leucine, isoleucine, 2-dimethylaminobenzoic acid, glycolamide, formic acid, propionic acid, butyric acid, oxalic acid, maleic acid, trifluoroacetic acid, malonic ester, acetoacetic ester, ethylene glycol dimethyl ether, 2-methoxyethanol, glycolic acid, glycolic ester, 1,3-propanediol, 1,4-butanediol, 1,5-pentanediol, diethylene glycol, catechol, 2-hydroxymethyl-1,3-propanediol, N,N-dimethylurea, N,N-diphenylurea or N,N-dimethylglycinamide.

24. A process for producing a compound represented by Formula (V):

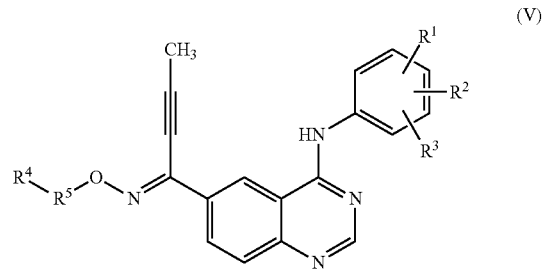

(V)

wherein $R^1$ is a hydrogen atom, halogen, substituted or unsubstituted alkyloxy, substituted or unsubstituted alkenyloxy, substituted or unsubstituted alkynyloxy or a group represented by formula: —Y—$R^y$, wherein —Y— is —O—, —S—, —$SO_2$—, or alkylene which may be intervened with —O—, —S— or —N($R^z$)—, $R^y$ is substituted or unsubstituted aromatic carbocyclyl or substituted or unsubstituted aromatic heterocyclyl, and $R^z$ is a hydrogen atom, substituted or unsubstituted alkyl, substituted or unsubstituted acyl, substituted or unsubstituted alkyloxycarbonyl, substituted or unsubstituted alkenyloxycarbonyl or substituted or unsubstituted aromatic carbocyclyl alkyloxycarbonyl;

$R^2$ and $R^3$ are each independently a hydrogen atom, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, halogen, hydroxy, mercapto, cyano or substituted or unsubstituted amino, $R^4$ is substituted or unsubstituted aromatic carbocyclyl, substituted or unsubstituted aromatic heterocyclyl, substituted or unsubstituted non-aromatic heterocyclyl or substituted or unsubstituted amino, and $R^5$ is substituted or unsubstituted C1 to 3 alkylene, characterized in that the compound represented by Formula (II') which is prepared by the process according to claim 7, is reacted with a compound represented by Formula (IV): $R^4$—$R^5$—O—$NH_2$, wherein $R^4$ and $R^5$ are as defined above.

25. A process for producing a compound represented by Formula (V'):

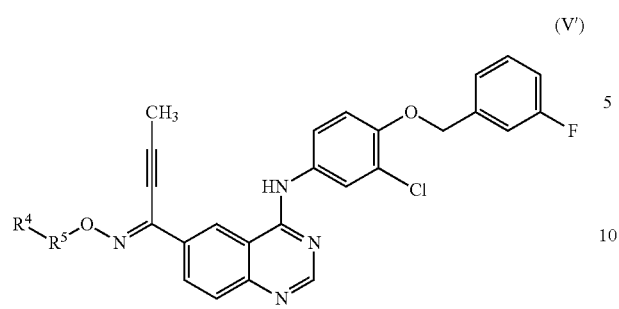

wherein R⁴ is substituted or unsubstituted aromatic carbocyclyl, substituted or unsubstituted aromatic heterocyclyl, substituted or unsubstituted non-aromatic heterocyclyl or substituted or unsubstituted amino, and R⁵ is substituted or unsubstituted C1 to 3 alkylene, characterized in that the compound represented by Formula (II″) which is prepared by the process according to claim 9, is reacted with the compound represented by Formula (IV): R⁴—R⁵—O—NH₂, wherein R⁴ and R⁵ are as defined above.

* * * * *